(12) United States Patent
Elghazaly et al.

(10) Patent No.: US 9,308,031 B2
(45) Date of Patent: Apr. 12, 2016

(54) LOCKABLE INTRAMEDULLARY FIXATION DEVICE

(75) Inventors: Timothy M. Elghazaly, Piscataway, NJ (US); Joseph M. O'Reilly, Granger, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 193 days.

(21) Appl. No.: 13/415,336

(22) Filed: Mar. 8, 2012

(65) Prior Publication Data

US 2012/0197255 A1     Aug. 2, 2012

Related U.S. Application Data

(63) Continuation-in-part of application No. 12/183,142, filed on Jul. 31, 2008, which is a continuation-in-part of application No. 11/627,575, filed on Jan. 26, 2007, now Pat. No. 8,303,590, and a continuation-in-part of application No. 12/117,765, filed on May 9, 2008, now Pat. No. 8,157,802.

(51) Int. Cl.
   *A61B 17/72*            (2006.01)
   *A61B 17/74*            (2006.01)
   *A61B 17/17*            (2006.01)

(52) U.S. Cl.
CPC ........... *A61B 17/725* (2013.01); *A61B 17/7241* (2013.01); *A61B 17/744* (2013.01); *A61B 17/1725* (2013.01); *A61B 17/7225* (2013.01); (Continued)

(58) Field of Classification Search
CPC .. A61B 17/72; A61B 17/7241; A61B 17/725; A61B 17/8047
USPC .............................................. 606/62–68, 290
See application file for complete search history.

(56) References Cited

U.S. PATENT DOCUMENTS 1,007,107 A     10/1911     Hulsmann
2,068,152 A      1/1937     Rowe (Continued)

FOREIGN PATENT DOCUMENTS

DE          69511549 T2     3/2000
EP           0764006 A1     3/1997

(Continued)

OTHER PUBLICATIONS

Graziani et al., WO 2005053550 A1, Jun. 2005, World Intellectual Property Organization (WIPO), English machine translation.*

(Continued)

*Primary Examiner* — Jerry Cumberledge
(74) *Attorney, Agent, or Firm* — Schwegman Lundberg & Woessner, P.A.

(57) ABSTRACT

An orthopedic device is provided. The orthopedic device can include an intramedullary implant defining a longitudinal bore along a longitudinal axis. The intramedullary implant can define at least one bore formed along an axis for receipt of a fastener. The orthopedic device can include a fixation device receivable within the longitudinal bore. The fixation device can have at least one guiding bore formed along a guiding axis transverse to the longitudinal axis. The orthopedic device can include at least one collet received within the at least one guiding bore for positioning and locking the fastener at a variable angle relative to the guiding axis of the fixation device and the axis of the intramedullary implant.

16 Claims, 56 Drawing Sheets

(52) U.S. Cl.
CPC ..... *A61B 17/7233* (2013.01); *A61B 2017/1775* (2013.01)

(56) References Cited

U.S. PATENT DOCUMENTS

| | | |
|---|---|---|
| 2,201,674 A | 5/1940 | Rowe et al. |
| 2,222,156 A | 11/1940 | Rowe |
| 2,725,915 A | 12/1955 | Johnson |
| 2,789,276 A | 4/1957 | Hummel |
| 2,913,031 A | 11/1959 | McKay et al. |
| 3,308,865 A | 3/1967 | Raichelson et al. |
| 3,501,993 A | 3/1970 | Swenson |
| 3,709,218 A | 1/1973 | Halloran |
| 3,836,941 A | 9/1974 | Izraeli |
| 3,990,438 A | 11/1976 | Pritchard |
| 4,354,399 A | 10/1982 | Katayama |
| 4,429,600 A | 2/1984 | Gulistan |
| 4,450,835 A | 5/1984 | Asnis et al. |
| 4,466,314 A | 8/1984 | Rich |
| 4,622,959 A | 11/1986 | Marcus |
| 4,710,075 A | 12/1987 | Davison |
| 4,733,661 A | 3/1988 | Palestrant |
| 4,756,307 A | 7/1988 | Crowninshield |
| 4,776,330 A | 10/1988 | Chapman et al. |
| 4,827,917 A | 5/1989 | Brumfield |
| 4,828,562 A | 5/1989 | Kenna |
| 4,858,602 A | 8/1989 | Seidel et al. |
| 4,875,475 A | 10/1989 | Comte et al. |
| 4,895,572 A | 1/1990 | Chernoff |
| 5,034,013 A | 7/1991 | Kyle et al. |
| 5,041,114 A | 8/1991 | Chapman et al. |
| 5,041,115 A | 8/1991 | Frigg et al. |
| 5,066,296 A | 11/1991 | Chapman et al. |
| 5,112,333 A | 5/1992 | Fixel |
| 5,190,544 A | 3/1993 | Chapman et al. |
| 5,295,991 A | 3/1994 | Frigg |
| 5,383,525 A | 1/1995 | Daly et al. |
| 5,505,734 A | 4/1996 | Caniggia et al. |
| 5,549,610 A | 8/1996 | Russell et al. |
| 5,653,709 A | 8/1997 | Frigg |
| 5,658,287 A | 8/1997 | Hofmann et al. |
| 5,690,515 A | 11/1997 | Cipolla |
| 5,697,930 A | 12/1997 | Itoman et al. |
| 5,704,939 A | 1/1998 | Justin |
| 5,728,128 A | 3/1998 | Crickenberger et al. |
| 5,779,705 A | 7/1998 | Matthews |
| 5,935,127 A | 8/1999 | Border |
| 6,004,324 A * | 12/1999 | Gahr et al. ............ 606/67 |
| 6,010,506 A | 1/2000 | Gosney et al. |
| 6,019,761 A | 2/2000 | Gustilo |
| 6,036,696 A | 3/2000 | Lambrecht et al. |
| 6,077,267 A | 6/2000 | Huene |
| 6,080,024 A | 6/2000 | Miller et al. |
| 6,106,528 A * | 8/2000 | Durham et al. ............ 606/64 |
| 6,120,504 A | 9/2000 | Brumback et al. |
| 6,168,595 B1 | 1/2001 | Durham et al. |
| 6,214,013 B1 | 4/2001 | Lambrecht et al. |
| 6,221,074 B1 | 4/2001 | Cole et al. |
| 6,228,086 B1 | 5/2001 | Wahl et al. |
| 6,296,645 B1 | 10/2001 | Hover et al. |
| 6,402,753 B1 | 6/2002 | Cole et al. |
| 6,406,477 B1 | 6/2002 | Fujiwara |
| 6,461,360 B1 | 10/2002 | Adam |
| 6,520,969 B2 | 2/2003 | Lambrecht et al. |
| 6,547,791 B1 | 4/2003 | Buhren et al. |
| 6,562,042 B2 | 5/2003 | Nelson |
| 6,565,573 B1 | 5/2003 | Ferrante et al. |
| 6,569,165 B2 | 5/2003 | Wahl et al. |
| 6,579,294 B2 | 6/2003 | Robioneck |
| 6,648,889 B2 | 11/2003 | Bramlet et al. |
| 6,702,816 B2 | 3/2004 | Buhler |
| 6,709,436 B1 | 3/2004 | Hover et al. |
| 6,786,908 B2 | 9/2004 | Hover et al. |
| 6,808,527 B2 | 10/2004 | Lower et al. |
| 6,835,197 B2 | 12/2004 | Roth et al. |
| 6,921,400 B2 | 7/2005 | Sohngen |
| 6,926,719 B2 | 8/2005 | Sohngen et al. |
| 6,932,819 B2 | 8/2005 | Wahl et al. |
| 6,960,212 B2 | 11/2005 | Richelsoph et al. |
| 7,018,380 B2 | 3/2006 | Cole |
| 7,041,104 B1 | 5/2006 | Cole et al. |
| 7,112,063 B2 | 9/2006 | Bulard et al. |
| 7,182,765 B2 | 2/2007 | Roth et al. |
| 7,247,157 B2 * | 7/2007 | Prager et al. ............ 606/64 |
| 7,249,949 B2 | 7/2007 | Carter |
| 7,306,600 B2 | 12/2007 | Roth et al. |
| 7,311,712 B2 * | 12/2007 | Dalton ............ 606/71 |
| 7,325,470 B2 | 2/2008 | Kay et al. |
| 7,455,673 B2 | 11/2008 | Gotfried |
| 7,527,627 B2 | 5/2009 | Ferrante et al. |
| 7,763,021 B2 | 7/2010 | Cole et al. |
| 8,109,930 B2 * | 2/2012 | Schlienger et al. ............ 606/62 |
| 8,197,517 B1 * | 6/2012 | Lab et al. ............ 606/268 |
| 8,226,692 B2 * | 7/2012 | Mathieu et al. ............ 606/280 |
| 8,241,287 B2 * | 8/2012 | Prager et al. ............ 606/64 |
| 2002/0133156 A1 | 9/2002 | Cole |
| 2002/0156473 A1 | 10/2002 | Bramlet et al. |
| 2003/0114855 A1 | 6/2003 | Wahl et al. |
| 2003/0195515 A1 | 10/2003 | Sohngen |
| 2004/0138663 A1 | 7/2004 | Kosashvili et al. |
| 2004/0158252 A1 | 8/2004 | Prager et al. |
| 2004/0260307 A1 | 12/2004 | Zander |
| 2005/0010223 A1 | 1/2005 | Gotfried |
| 2005/0015131 A1 * | 1/2005 | Fourcault et al. ............ 607/116 |
| 2005/0069397 A1 | 3/2005 | Shavit et al. |
| 2005/0070903 A1 | 3/2005 | Roth et al. |
| 2005/0101958 A1 | 5/2005 | Adam |
| 2005/0107790 A1 | 5/2005 | Qian |
| 2005/0143739 A1 | 6/2005 | Shinjo et al. |
| 2005/0203510 A1 | 9/2005 | Sohngen |
| 2005/0273103 A1 | 12/2005 | Wahl et al. |
| 2006/0095040 A1 * | 5/2006 | Schlienger et al. ............ 606/73 |
| 2006/0111716 A1 | 5/2006 | Schlienger et al. |
| 2006/0111717 A1 | 5/2006 | Saueressig et al. |
| 2006/0122600 A1 | 6/2006 | Cole |
| 2006/0149264 A1 | 7/2006 | Castaneda et al. |
| 2006/0173457 A1 | 8/2006 | Tornier |
| 2006/0200141 A1 | 9/2006 | Janna et al. |
| 2006/0200160 A1 | 9/2006 | Border et al. |
| 2006/0235395 A1 | 10/2006 | Frigg et al. |
| 2007/0100343 A1 | 5/2007 | Cole et al. |
| 2007/0233100 A1 | 10/2007 | Metzinger |
| 2008/0114359 A1 * | 5/2008 | Murner et al. ............ 606/66 |
| 2008/0183171 A1 | 7/2008 | Elghazaly et al. |
| 2008/0221577 A1 | 9/2008 | Elghazaly |
| 2008/0294164 A1 | 11/2008 | Frank et al. |
| 2008/0300637 A1 | 12/2008 | Austin et al. |
| 2008/0306550 A1 * | 12/2008 | Matityahu ............ 606/290 |
| 2009/0048600 A1 | 2/2009 | Matityahu et al. |
| 2009/0062862 A1 * | 3/2009 | Perrow et al. ............ 606/280 |
| 2009/0192549 A1 * | 7/2009 | Sanders et al. ............ 606/280 |
| 2009/0318926 A1 | 12/2009 | Christie |
| 2010/0152787 A1 * | 6/2010 | Walsh et al. ............ 606/308 |

FOREIGN PATENT DOCUMENTS

| | | |
|---|---|---|
| EP | 1557131 | 7/2005 |
| ES | 2134479 T3 | 10/1999 |
| GB | 2290478 A | 1/1996 |
| WO | 9534248 A1 | 12/1995 |
| WO | 0143652 A | 6/2001 |
| WO | 0143652 A1 | 6/2001 |
| WO | 03061495 A2 | 7/2003 |
| WO | 03094763 A1 | 11/2003 |
| WO | 2004082493 A1 | 9/2004 |
| WO | 2004100810 A1 | 11/2004 |
| WO | WO 2005053550 A1 * | 6/2005 |
| WO | 2006107222 A2 | 10/2006 |
| WO | 2007038560 A1 | 4/2007 |

OTHER PUBLICATIONS

Halder, S.C., The Gamma Nail for Peritrochanteric Fractures, The Journal of Bone and Joint Surgery, May 1992, pp. 340-344, vol. 74-B, No. 3, 1992 British Editorial Society of Bone and Joint Surgery.

(56) References Cited

OTHER PUBLICATIONS

Damron, Timothy A., et al., Long Gamma Nail Stabilization of Pathologic and Impending Pathologic Femur Fractures, the University of Pennsylvania Orthopaedic Journal, 1999, pp. 13-20, vol. 12.
Synthesò, The Titanium Femoral Nail System, Solid and Cannulated Nails, Technique Guide, Ó1996 Synthes (USA).
Strykerò Trauma, One ShotÔ Device, GammaÒ Locking Nail Instruments, Opera Tive Technique, Ó2000 Stryker Corporation.
Strykerò Trauma, Gamma3Ô The Compact Version of the GammaÔ Nail System, Operative Technique, Hip Fracture System, Trochanteric and Long Nails, Brochure, Ó2004 Stryker, Printed in USA.
PCT International Search Report and The Written Opinion of the International Searching Authority for PCT/US2008/000568 mailed Jun. 2, 2008.
PCT International Preliminary Report on Patentability (Chapter I of the Patent Cooperation Treaty) with PCT Written Opinion of the International Searching Authority for PCT/US2008/000568 mailed Aug. 6, 2009.
Non-Final Office Action for U.S. Appl. No. 12/117,765, mailed Mar. 17, 2011.
Non-Final Office Action for U.S. Appl. No. 12/183,142, mailed Mar. 16, 2011.
Office Action regarding European Patent Application No. 08 724 539.5-2310, dated Apr. 19, 2011.
First Office Action regarding Chinese Patent Application No. 200910137547.5, dated Jan. 26, 2011. English translation provided by Unitalen Attorneys at Law.
First Office Action regarding Chinese Patent Application No. 200880006581.2, dated Jan. 30, 2011. English translation provided by Unitalen Attorenys at Law.
Final Office Action for U.S. Appl. No. 11/627,575 Mailed Sep. 24, 2010.
Non-Final Office Action for U.S. Appl. No. 11/627,575 Mailed Mar. 25, 2010.
Final Office Action for U.S. Appl. No. 12/117,765 Mailed Sep. 13, 2011.
Final Office Action for U.S. Appl. No. 12/183,142 Mailed Sep. 6, 2011.
Chinese First Office Action Dated Aug. 17, 2011; Machine Translation provided by Unitalen.
Non-Final Office Action for U.S. Appl. No. 11/627,575 Mailed Dec. 21, 2011.
Second Chinese Office Action for Patent Application No. 200910137547.5 Mailed Dec. 16, 2011 (English Translation provided by Peksung Intellectual Property Ltd.).
First Official Report for Australian Patent Application No. 2008211285, dated Jul. 4, 2012.

* cited by examiner

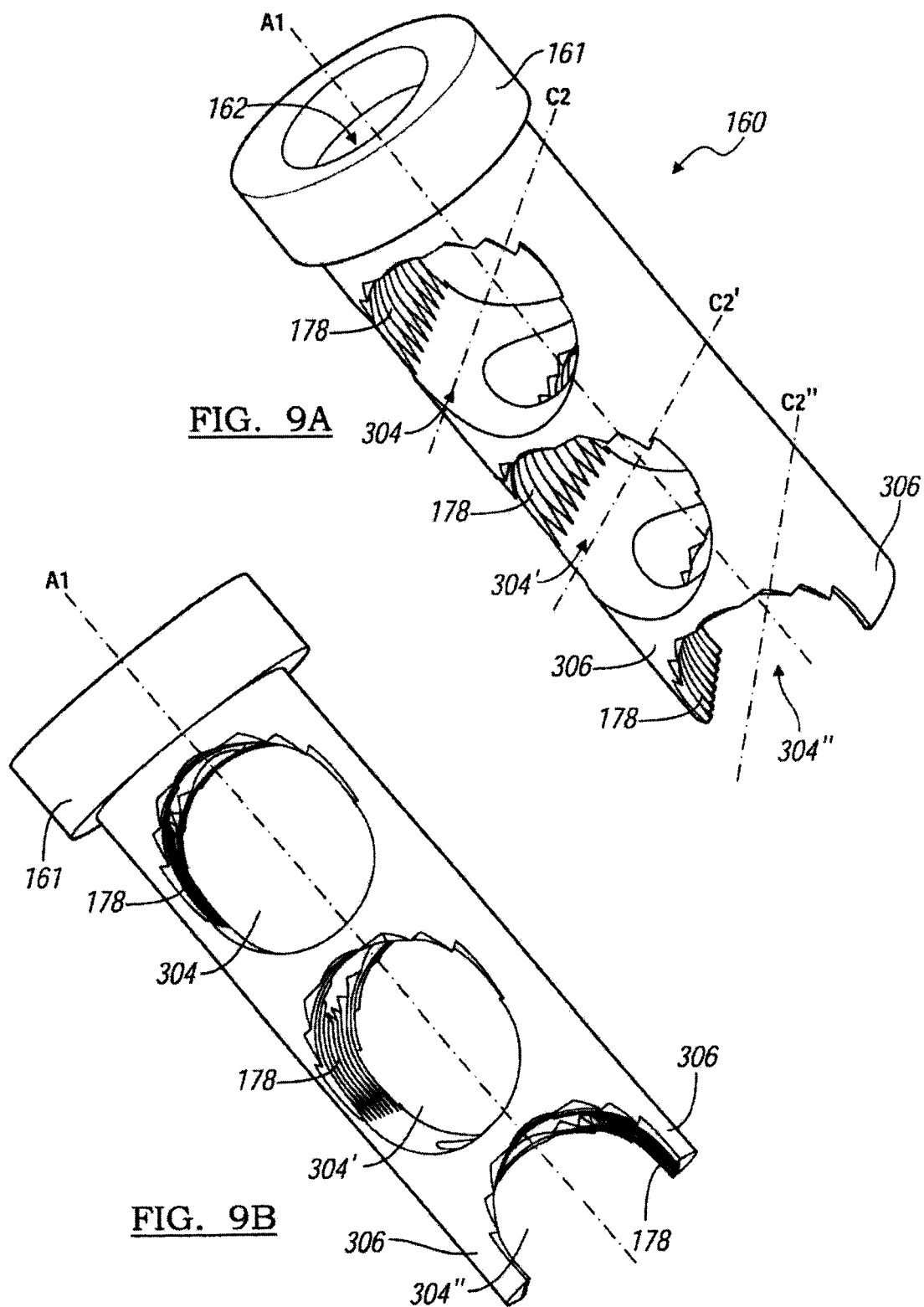

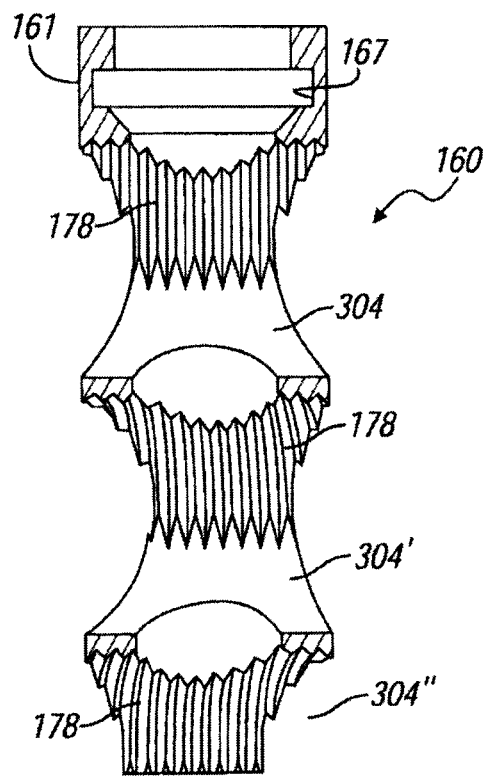
FIG. 9C
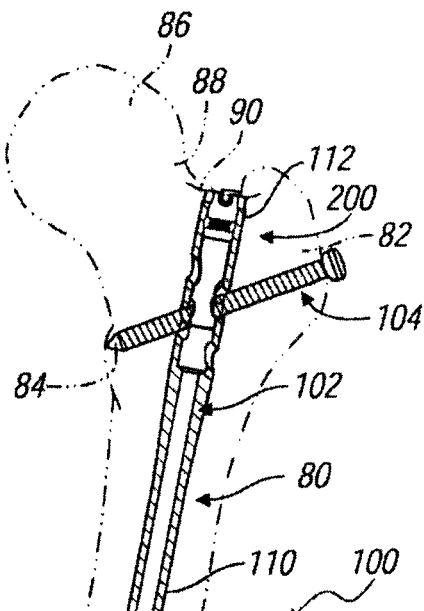
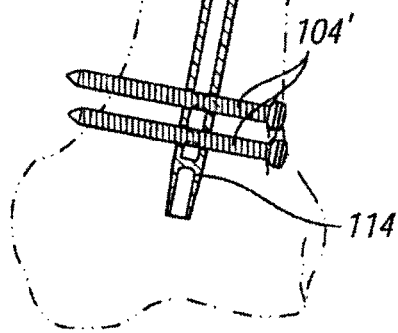
FIG. 10

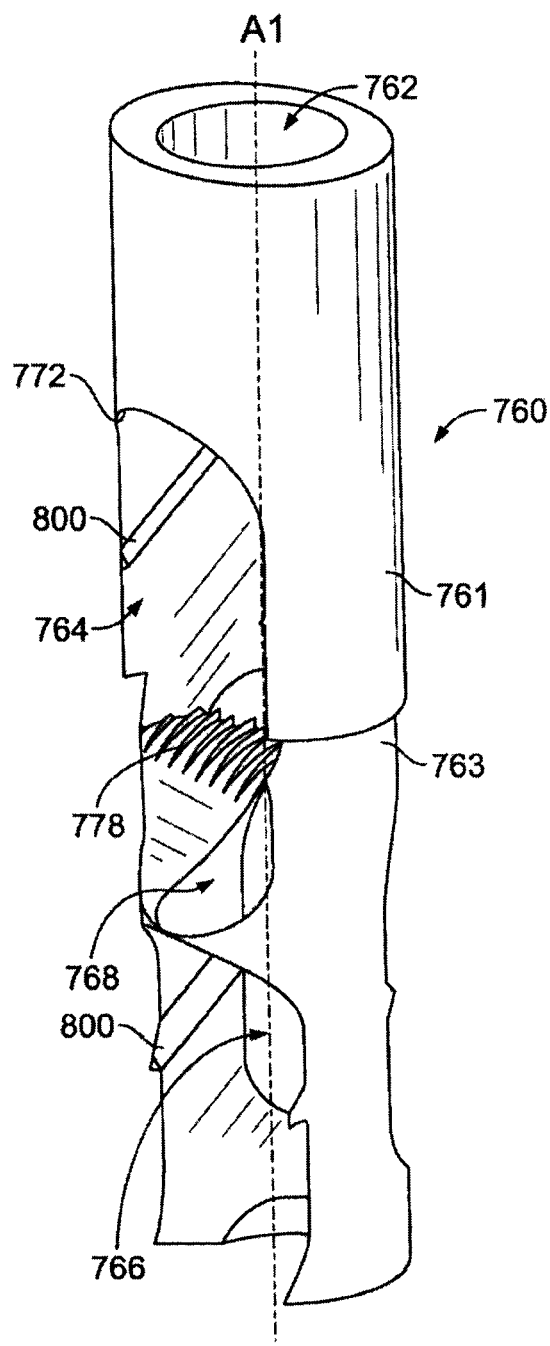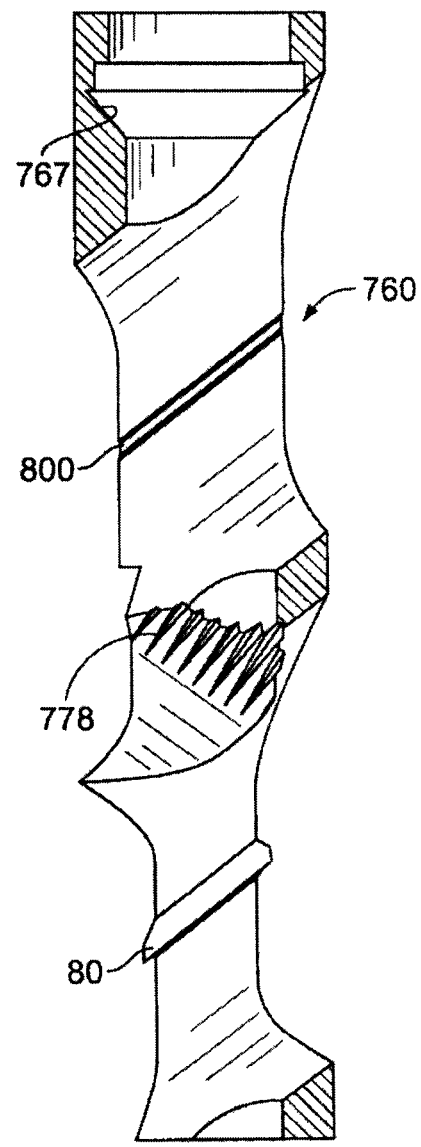
FIG. 21  FIG. 22

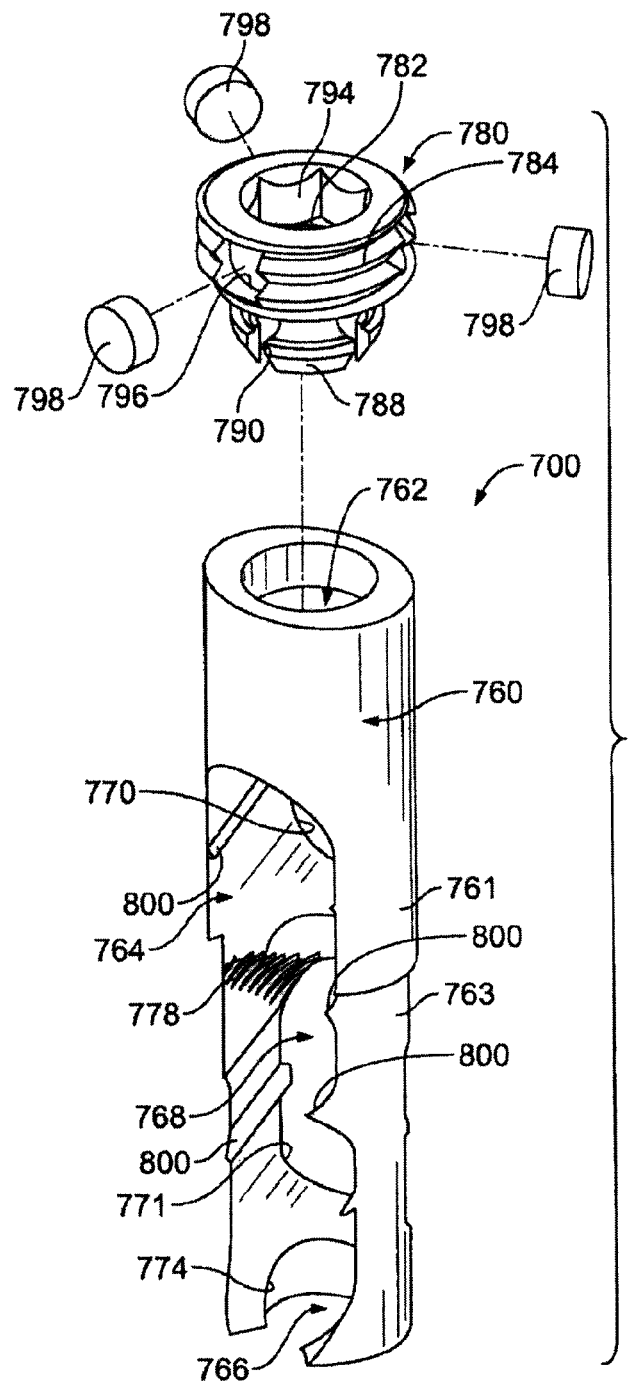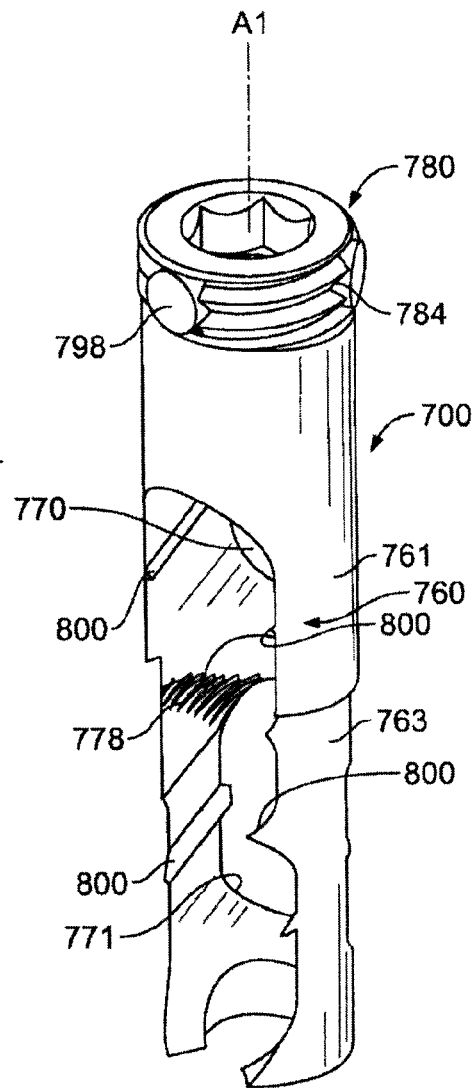
FIG. 25 FIG. 26

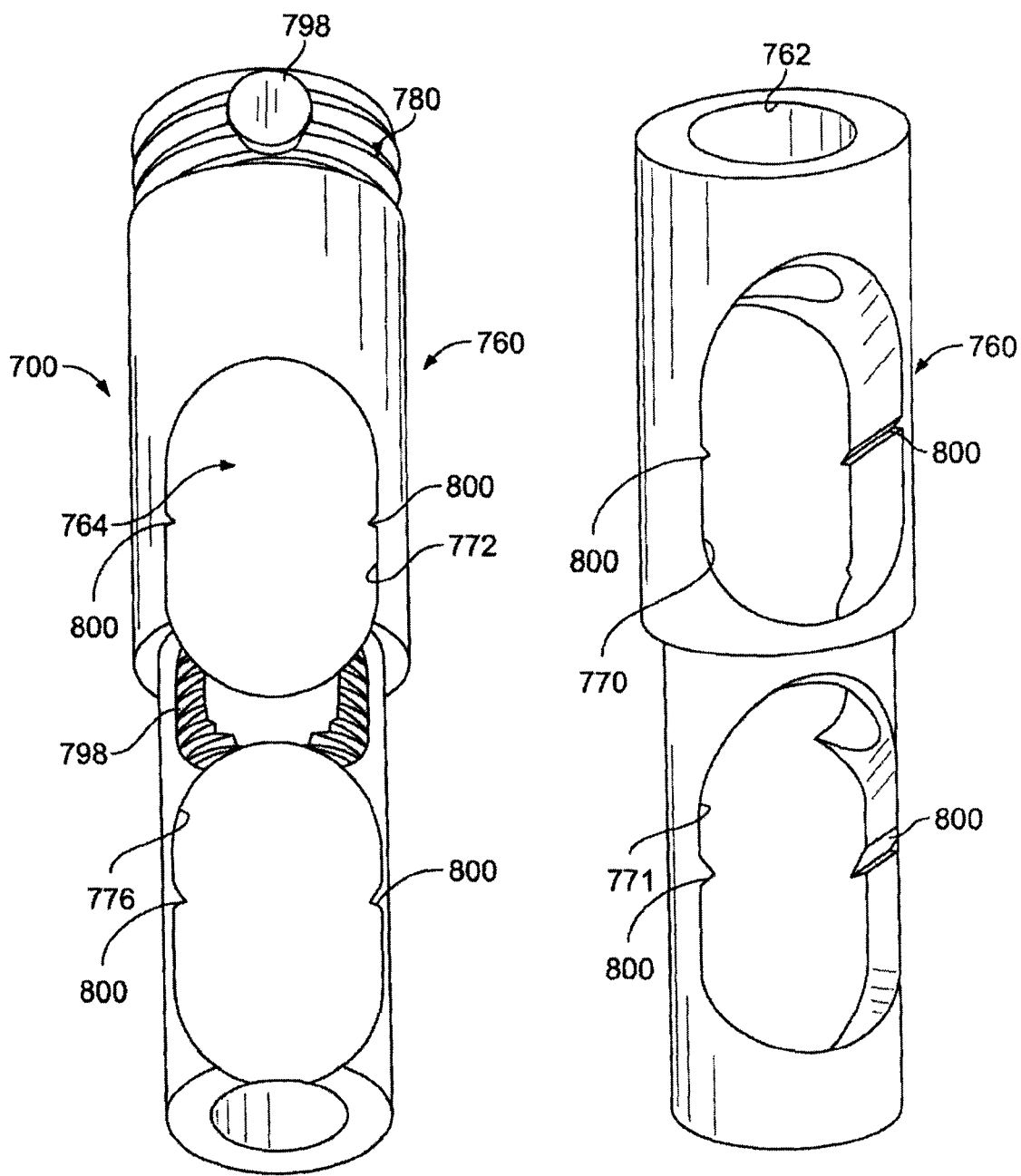
FIG. 27  FIG. 28

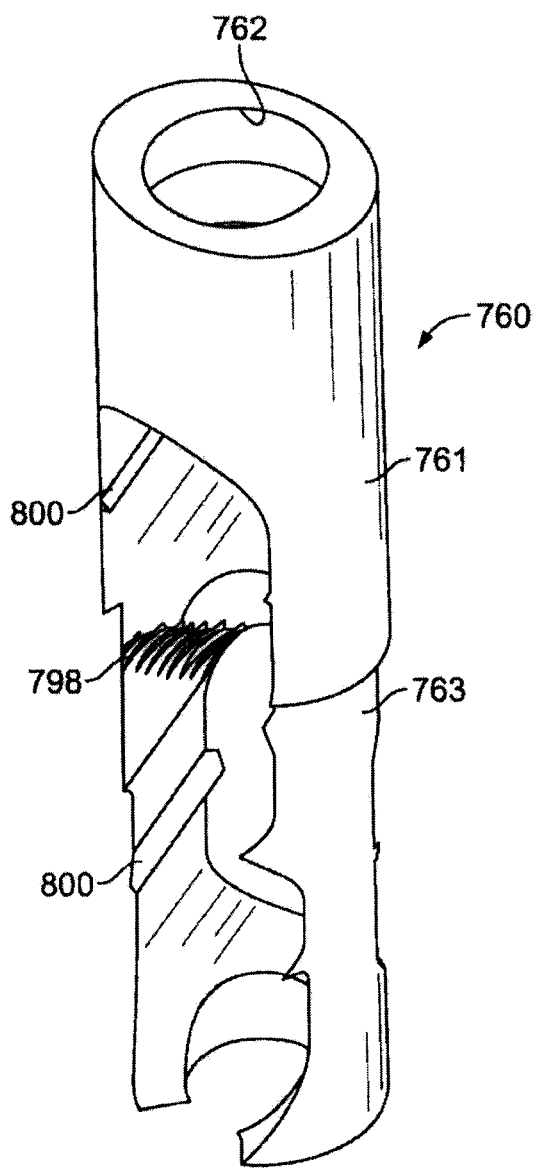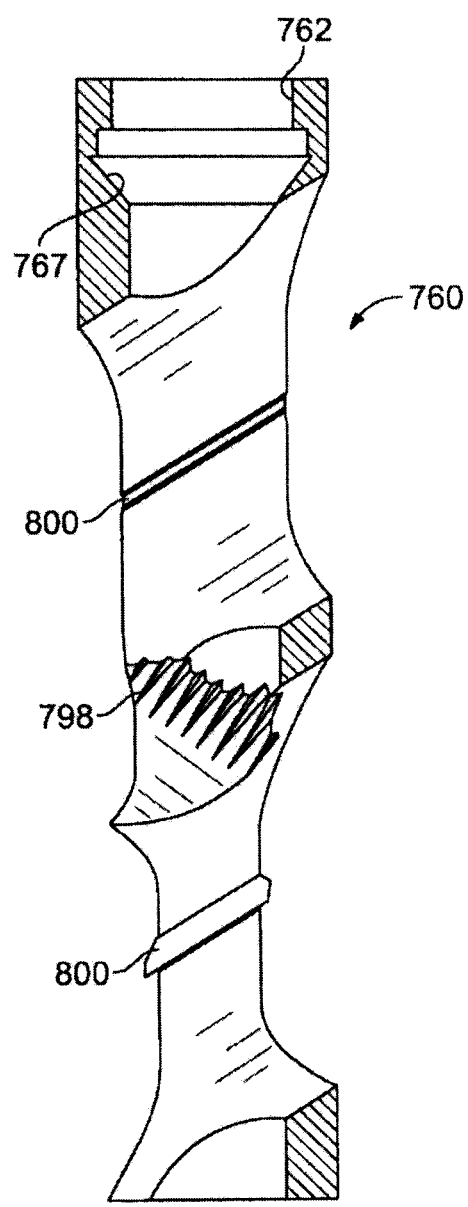
FIG. 29                    FIG. 30

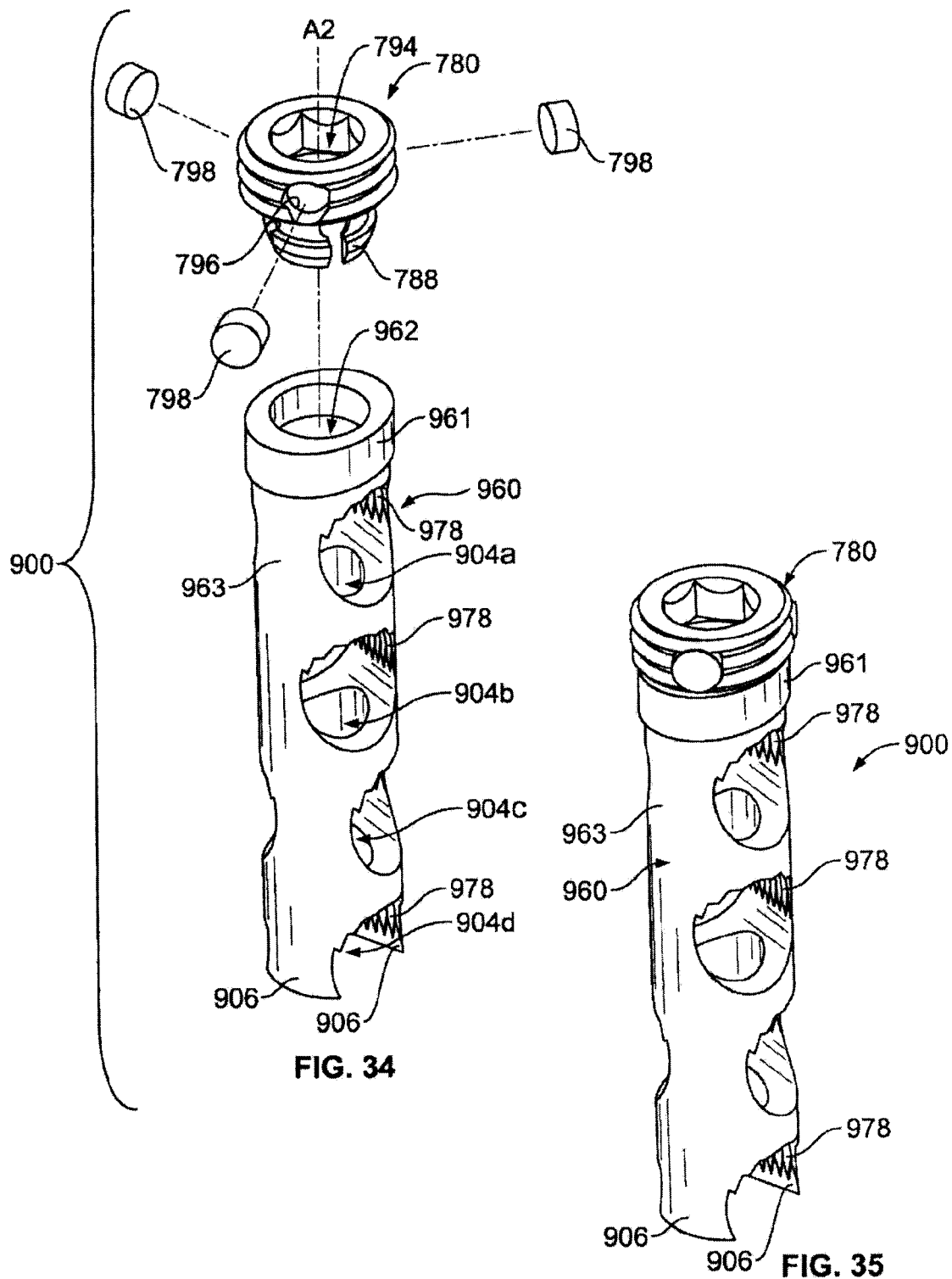

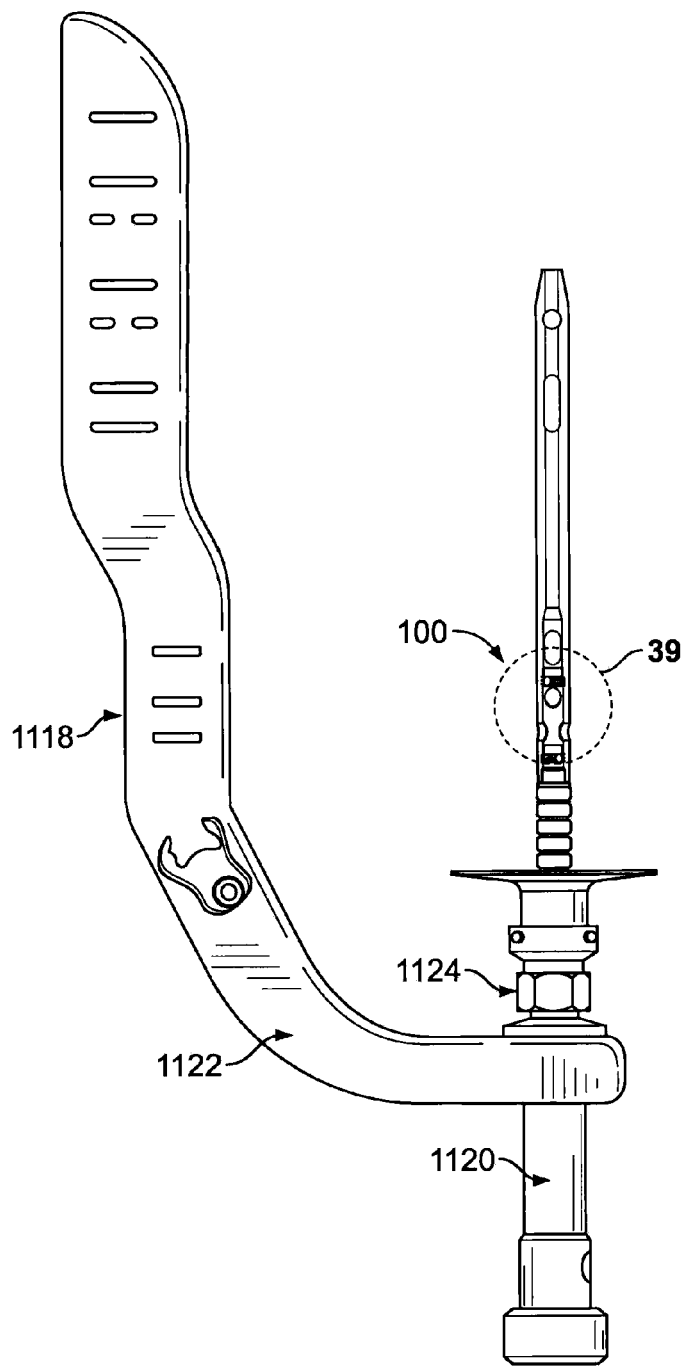
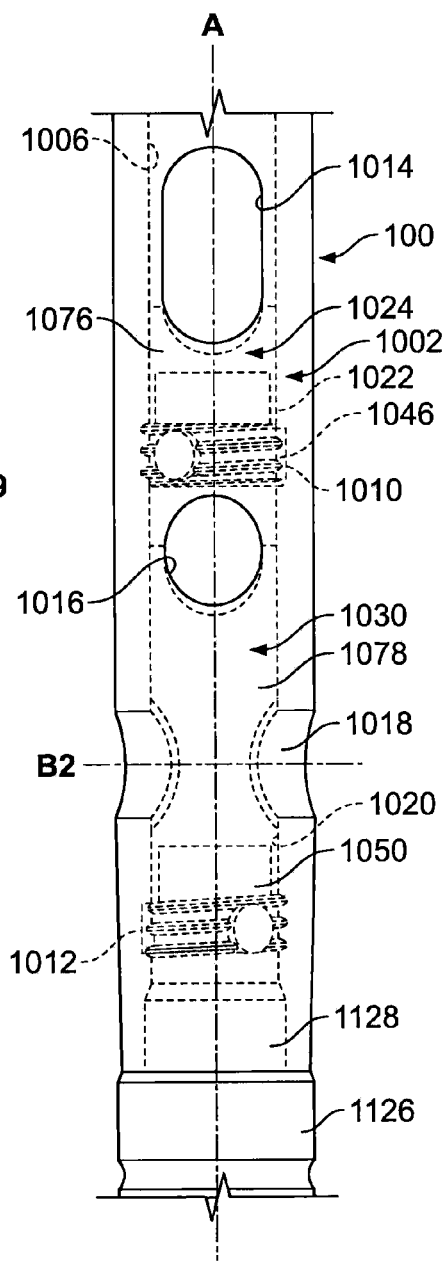
FIG. 38
FIG. 39

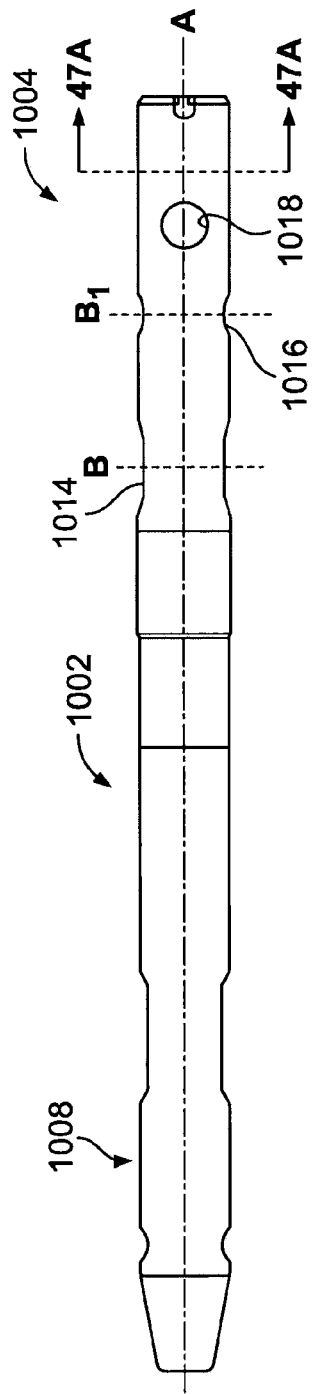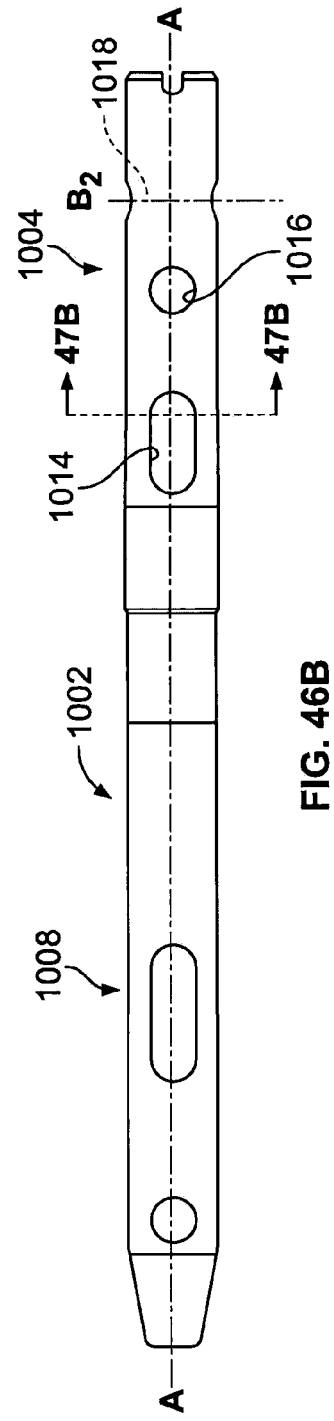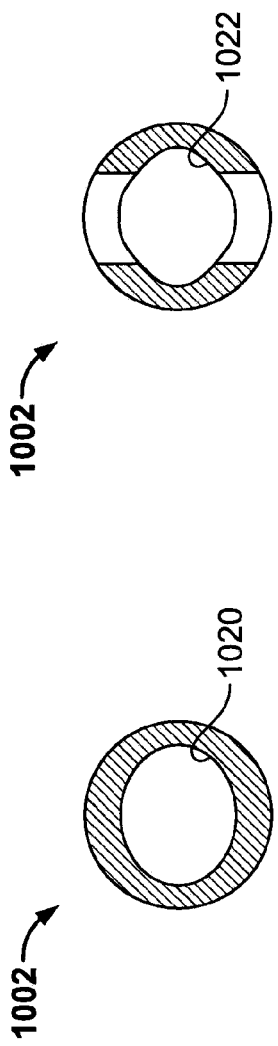

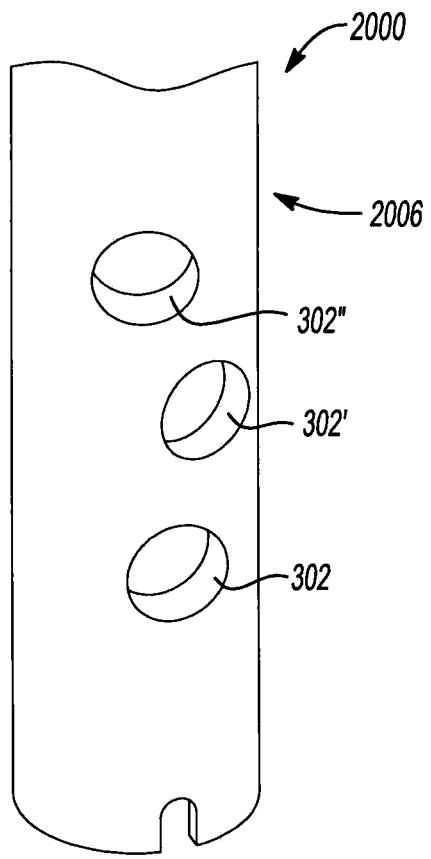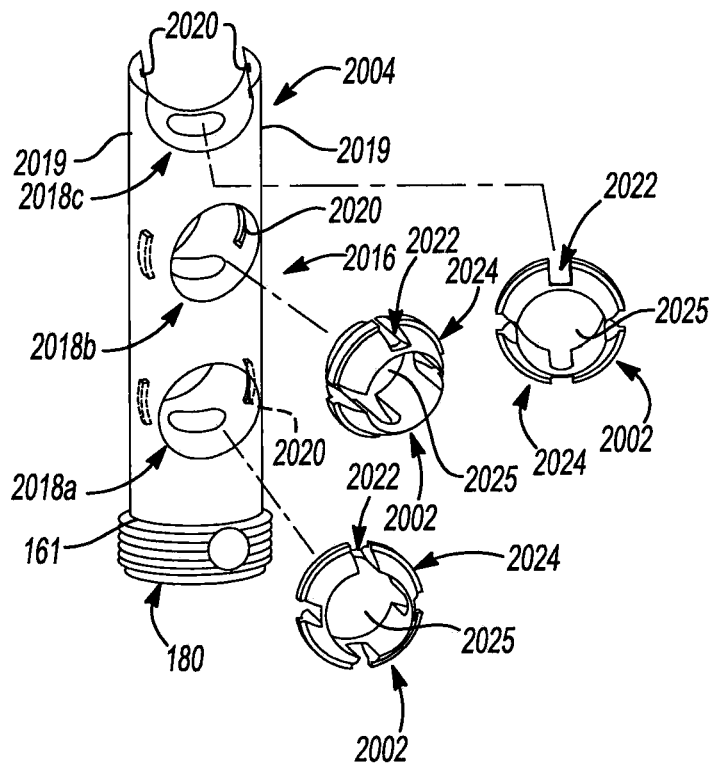
Fig-49

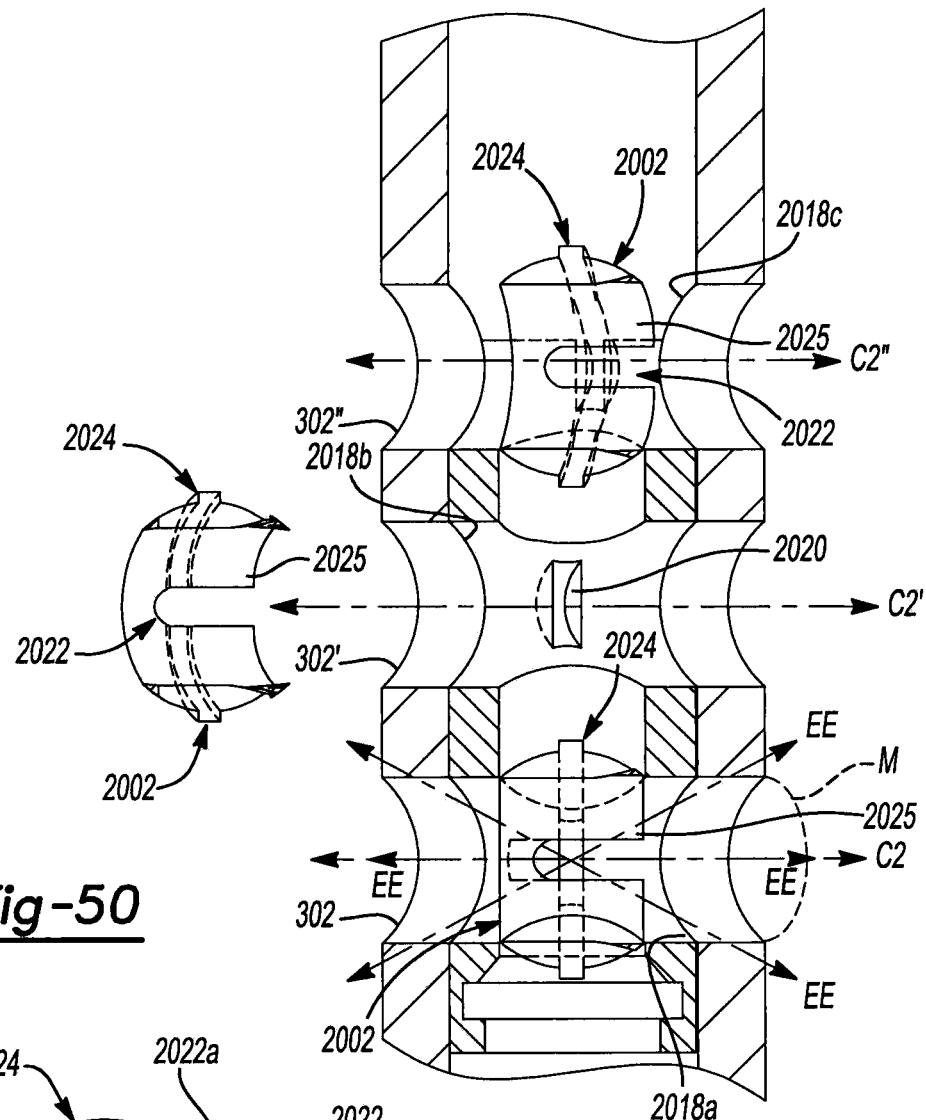
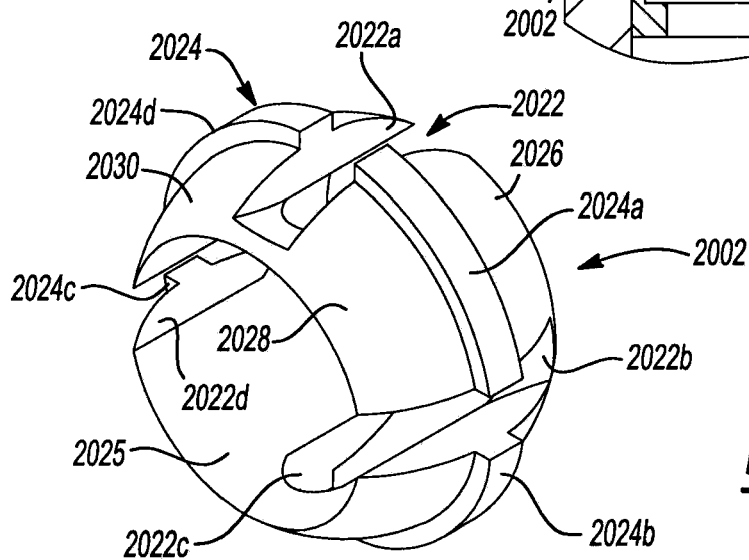
Fig-50
Fig-51

LOCKABLE INTRAMEDULLARY FIXATION DEVICE

CROSS-REFERENCE TO RELATED APPLICATIONS

This application is a continuation-in-part of U.S. Pat. application No. 12/183,142, filed on Jul. 31, 2008. U.S. Pat. application No. 12/183,142 is a continuation-in-part of U.S. Pat. application No. 11/627,575, filed on Jan. 26, 2007, now U.S. Pat. No. 8,303,590, and is also a continuation-in-part of U.S. Pat. application No. 12/117,765, filed on May 9, 2008. The disclosures of the above applications are incorporated herein by reference.

INTRODUCTION

Different nailing systems and associated instruments are known for the fixation of fractures of the femur, such as shaft fractures, subtrochanteric fractures, intertrochanteric fractures, neck fractures and combinations thereof, as well as for reconstruction of the femur following tumor resection or other surgery.

The present teachings provide for versatile and effective internal fixation devices that can be used for internal fixation of long bones.

SUMMARY

The present teachings provide an orthopedic device that includes an intramedullary implant defining a longitudinal bore, and a cannulated movable member receivable within the longitudinal bore and telescopically movable relative to the longitudinal bore. The movable member defines a plurality of guiding bores for bone fasteners, and is movable between a fastener engagement position and a fastener disengagement position. The guiding bores can be at an angle relative to the longitudinal bore of the intramedullary implant.

In another aspect, the present teachings provide an orthopedic device that includes an intramedullary implant defining a longitudinal bore and a plurality of fastener bores inclined relative to the longitudinal bore, a plurality of bone fasteners receivable in corresponding fastener bores, and a securing device. The securing device can move telescopically within the longitudinal bore between a first position that engages at least two bone fasteners to the intramedullary implant, and a second position that disengages the two bone fasteners from to the intramedullary implant.

In yet another aspect, the present teachings provide an intramedullary implant defining a longitudinal bore and at least first and second fastener bores inclined relative to the longitudinal bore. The orthopedic device can further include at least first and second of bone fasteners receivable in the corresponding first and second fastener bores, a movable member and a locking member. The movable member defines at least first and second guiding bores for receiving the first and second fasteners, and can telescopically move within the longitudinal bore between a first position that engages the first and second bone fasteners to the intramedullary implant, and a second position that disengages the first and second bone fasteners from to the intramedullary implant, the movable member. The locking member can have an externally threaded portion threadably engageable to a threaded portion of the longitudinal bore, and a resilient portion couplable to the movable member.

The present teachings further provide an orthopedic device that includes an intramedullary implant defining a longitudinal bore, at least one bone fastener, and a securing device. The securing device is movable within the longitudinal bore between a locked position that engages the at least one bone fastener to the intramedullary implant, and an unlocked position that disengages the at least one bone fastener from to the intramedullary implant. The securing device includes at least one guiding bore threadably engageable or threadably disengageable with the at least one bone fastener while the securing device is in the locked position.

In another aspect, the present teachings provide an orthopedic device including an intramedullary implant defining a longitudinal bore, first and second fasteners, each fastener including a threaded shaft and a substantially cylindrical unthreaded sleeve, and a cannulated movable member receivable within the longitudinal bore and telescopically movable relative to the longitudinal bore. The movable member defines first and second guiding bores for respectively receiving the first and second fasteners. Each of the first and second guiding bores is at an angle relative to the longitudinal bore. Each of the first and second guiding bores includes a pair of opposing deformable elongated strips engageable with the respective sleeve. The movable member can move between a fastener engagement position and a fastener disengagement position.

In another aspect, the orthopedic device includes an intramedullary implant defining a longitudinal bore, and first and second fasteners, each of the first and second fasteners including a threaded shaft telescopically received in a corresponding substantially cylindrical unthreaded sleeve. The orthopedic device also includes a third fastener including a threaded shaft, and a cannulated movable member receivable within the longitudinal bore and telescopically movable relative to the longitudinal bore. The movable member defines first, second and third guiding bores for selectively receiving respectively the first, second and third fasteners. The first, second and third guiding bores are at variable angles relative to the longitudinal bore and at variable angles relative to one another. Each of the first and second guiding bores includes a pair of opposing deformable elongated strips engageable with the respective sleeve. The third guiding bore includes a threaded formation engageable with the threaded shaft of the third fastener. The movable member moves between a fastener engagement position and a fastener disengagement position.

In a further aspect, the orthopedic device includes an intramedullary implant defining a longitudinal bore and first, second, third and fourth bone fasteners passing at variable angles and positions through the longitudinal bore of the intramedullary implant. The orthopedic device also includes a movable member defining first, second, third and fourth guiding bores for receiving the first, second, third and fourth fasteners. The movable member can move telescopically within the longitudinal bore between a first position that engages the first, second, third and fourth bone fasteners to the intramedullary implant, and a second position that disengages the first, second, third and fourth bone fasteners from the intramedullary implant.

Also provided according to various aspects is an orthopedic device. The orthopedic device can include an intramedullary implant defining a longitudinal bore along a longitudinal axis. The intramedullary implant can define at least one bore formed along an axis for receipt of a fastener. The orthopedic device can include a fixation device receivable within the longitudinal bore. The fixation device can have at least one guiding bore formed along a guiding axis transverse to the longitudinal axis. The orthopedic device can include at least one collet received within the at least one guiding bore for positioning the fastener at a variable angle relative to the guiding axis of the fixation device and the axis of the intramedullary implant.

Further provided is an orthopedic device, which can comprise a fixation device. The fixation device can have a longitudinal axis and can define at least a first guiding bore along a first guiding axis transverse to the longitudinal axis and second guiding bore along a second guiding axis transverse to the longitudinal axis. The first guiding bore and the second guiding bore can each include a retaining feature formed along a portion of each of the first guiding bore and the second guiding bore. The orthopedic device can also include a collet coupled to the retaining feature of each of the first guiding bore and the second guiding bore so that each collet is movable relative to each of the first guiding bore and the second guiding bore for positioning a fastener at a variable angle relative to the respective one of the first guiding axis and second guiding axis.

An orthopedic device is also provided. The orthopedic device can include an intramedullary implant defining a longitudinal bore along a longitudinal axis and at least one bore formed along an axis transverse to the longitudinal axis for receipt of a fastener. The orthopedic device can also include a movable fixation device receivable within the longitudinal bore. The fixation device can have at least one guiding bore formed along a guiding axis transverse to the longitudinal axis. The at least one guiding bore can include a retaining feature formed along at least a portion of the guiding bore. The at least one guiding bore can be coaxially aligned with the at least one bore when the fixation device is in a first position. The orthopedic device can include at least one deformable collet having a rib coupled to the retaining feature of the at least one guiding bore for positioning the fastener at a variable angle relative to the guiding axis of the fixation device and the axis of the intramedullary nail. The movement of the fixation device from the first position to a second position within the longitudinal bore can deform the at least one collet to couple the fastener to the intramedullary implant.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present invention will become more fully understood from the detailed description and the accompanying drawings, wherein:

FIGS. 9A and 9B are perspective views of an insert for the fixation device of FIG. 7;

FIG. 9C is a sectional view of the insert of FIG. 9A;

FIG. 10 is an environmental view of a fixation device according to the present teachings, illustrating a piriformis procedure with interlocking fixation fasteners;

FIG. 21 is a perspective view of an insert for the intramedullary implant of FIG. 20;

FIG. 22 is a sectional view of the insert of FIG. 21;

FIG. 25 is an exploded view of a securing device for the intramedullary implant of FIG. 24;

FIGS. 26 and 27 are perspective views of the securing device of FIG. 25;

FIGS. 28 and 29 are perspective views of an insert of the securing device of FIG. 25;

FIG. 30 is a sectional elevated view of the insert of FIG. 28;

FIG. 34 is an exploded view of a securing device for the intramedullary implant of FIG. 33;

FIG. 35 is a perspective view of the securing device of FIG. 34;

FIG. 38 is an elevation view of an intramedullary fixation device according to the present teachings, the fixation device shown mounted on a targeting instrument;

FIG. 39 is an elevated view of Detail 39 of FIG. 38;

FIG. 46A is a first side view of an intramedullary implant according to the present teachings;

FIG. 46B is a second side view of an intramedullary implant according to the present teachings;

FIG. 47A is a sectional view of the intramedullary implant of FIG. 46A taken along line 47A-47A;

FIG. 47B is a sectional view of the intramedullary implant of FIG. 46B taken along line 47B-47B;

FIG. 49 is an exploded view of the intramedullary implant of FIG. 48;

FIG. 50 is a cross-sectional view of a portion of the intramedullary implant of FIG. 48, taken along line 50-50 of FIG. 48;

FIG. 51 is a perspective view of the variable angle positioning member of FIG. 48;

DESCRIPTION OF VARIOUS ASPECTS

Figure 1:
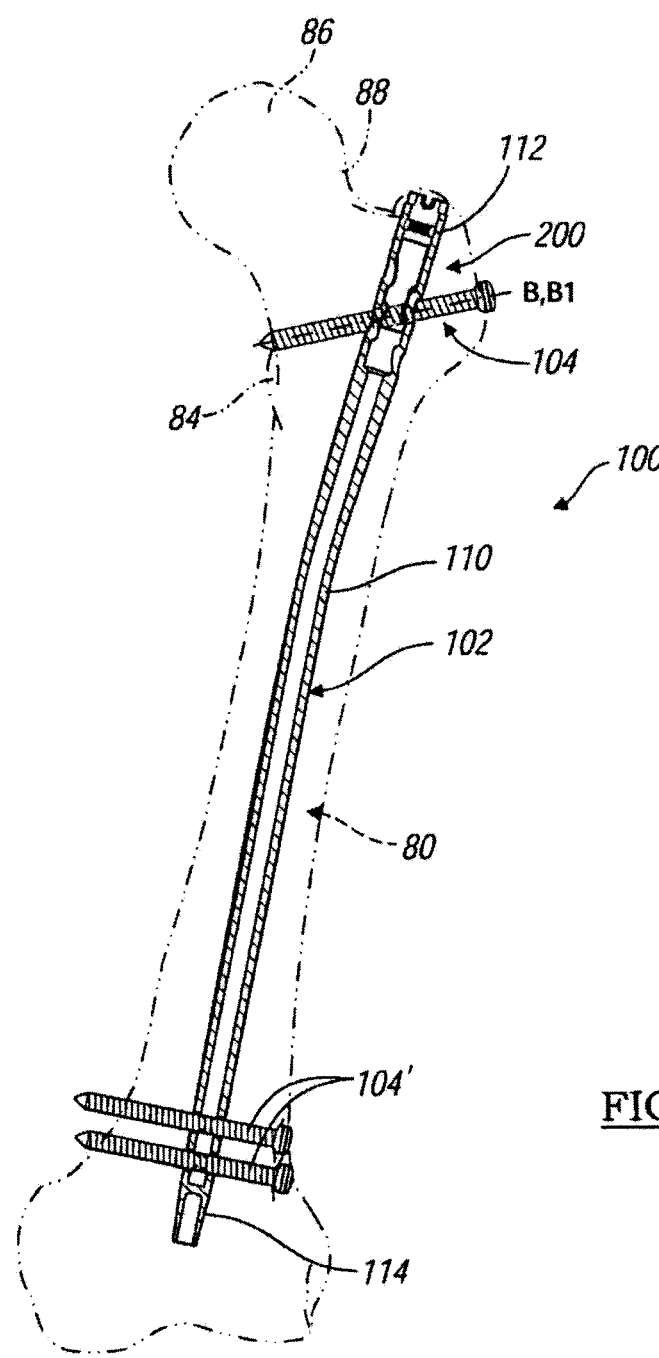
FIG. 1 is an environmental view of a fixation device according to the present teachings, illustrating a trochanteric procedure with interlocking fixation fasteners.

The following description is merely exemplary in nature and is in no way intended to limit the invention, its application, or uses. For example, although the present teachings are illustrated for exemplary trochanteric, piriformis and retrograde procedures with reconstructive or interlocking femoral fixation, and for proximal tibial fixation, the present teachings can be used for other fixation procedures involving long bones. It will be understood that general surgical procedures are outlined only as needed to illustrate the devices and methods provided by the present teachings, while detailed descriptions of standard and known procedures and instruments are omitted for simplicity.

Exemplary fixation devices 100 are illustrated and described below. FIGS. 1-6C illustrate fixation devices for trochanteric femoral fixation, FIGS. 7-9B for retrograde femoral fixation, FIGS. 10-14C for piriformis femoral fixation, and FIGS. 15-19B for cortical tibial fixation. Although some of the structural details and/or sizes of the fixation components for each procedure may differ, each fixation device 100 can include an intramedullary nail or implant 102, a telescopic clamp or securing device 200 that includes a hollow insert or similar movable member 160 and a cannulated set screw or similar locking member 180, and various bone fasteners, including single-piece interlocking bone fasteners 104 and reconstruction fasteners 140, including lag screws and telescopic screws slidable within sleeves. The movable member 160 can be cannulated and can include a plurality of openings defining guiding bores configured for guiding the orientation of corresponding bone fasteners, as is described below in reference to particular procedures. In the interest of brevity, details described with respect to one procedure will generally not be repeated in other procedures. For example, although dynamic and static engagement positions of the movable member 160 of the telescopic clamp/securing device 200 device are illustrated with respect to tibial procedures in FIGS. 18A and 18B, it will be understood that telescopic clamp/securing device 200 device can operate similarly in all the other procedures.

Figure 1A:
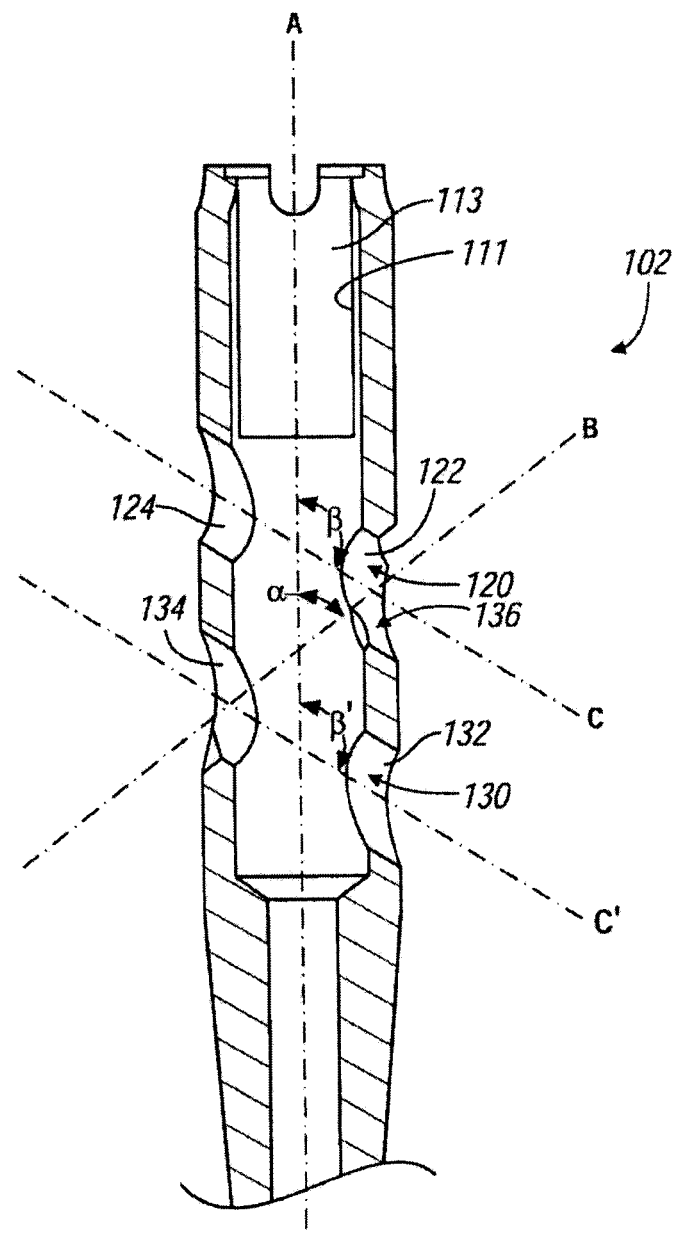
FIG. 1A is a sectional view of a proximal portion of an intramedullary implant of the fixation device of FIG. 1.
Figure 2:
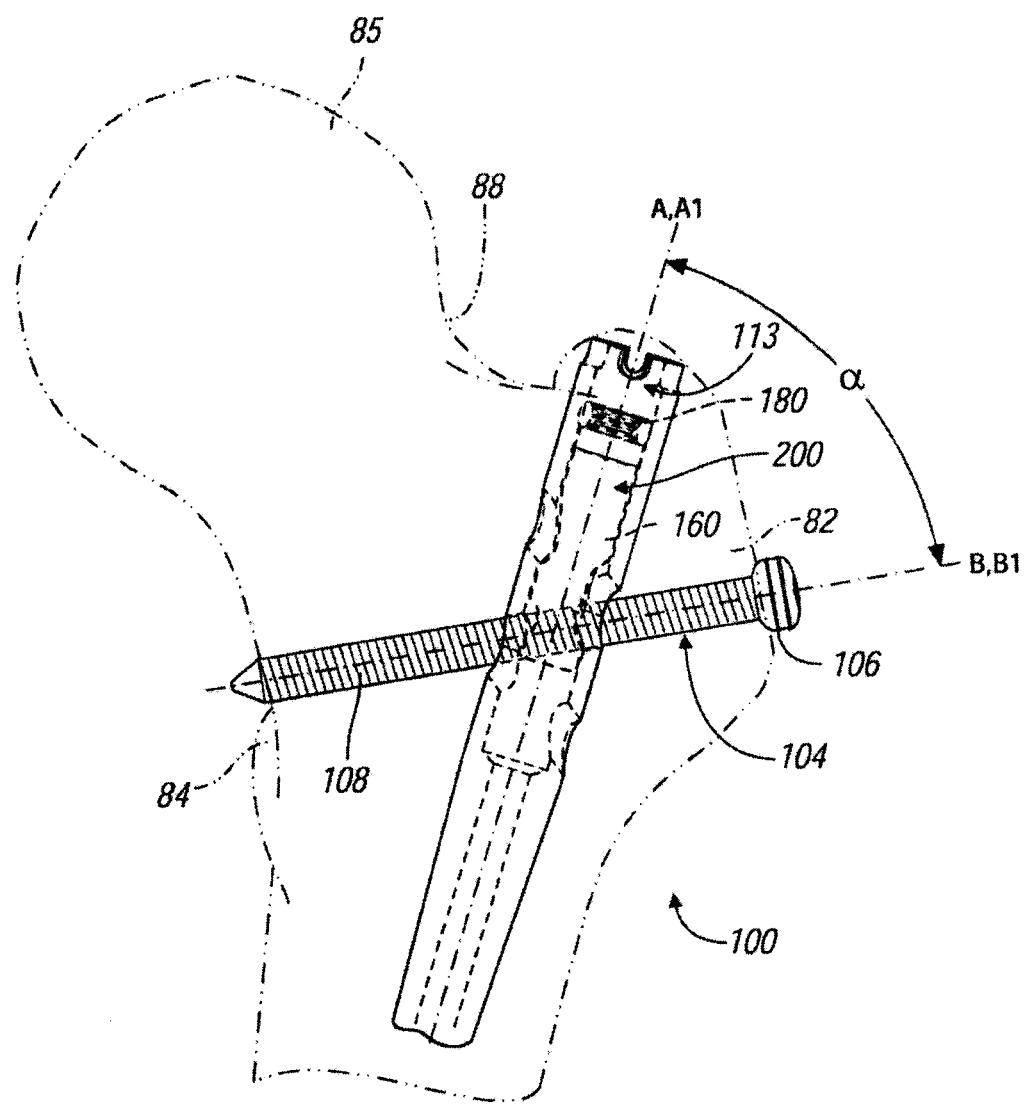
FIG. 2 is an enlarged view of a detail of FIG. 1.

Referring to FIGS. 1, 1A, and 2, an exemplary fixation device 100 according to the present teachings is shown implanted in a femur 80 for an interlocking trochanteric procedure. The fixation device 100 can include an elongated intramedullary (IM) implant 102 and an elongated interlocking bone fastener 104. The IM implant 102 can include a shaft 110 having proximal and distal portions 112, 114 and received in the intramedullary canal of the femur 80. The proximal portion 112 of the IM implant 102 can include a proximal longitudinal bore 113 defining a longitudinal axis A. A proximal inner surface 111 of the proximal longitudinal bore 113 can be of elliptical or other non-circular shape, having different major and minor diameters such that the cross-section has an elongated shape.

The proximal portion 112 of the IM implant 102 can include first and second fastener bores 120, 130 along first and second axes C and C' at first and second angles β and β' relative to the longitudinal axis A, as shown in FIG. 1A. The axes C and C' can be parallel such that the angles β and β' are substantially equal. The first bore 120 can be defined by first and second opposite-side openings 122 and 124 that can be offset along the direction of axis A, thereby defining the first axis C at an angle β relative to the axis A. The second bore 130 can be defined by third and fourth opposite-side openings 132 and 134 that can be offset along the direction of axis A, such that they define the second axis C' at an angle β' relative to the axis A. The first, second, third and fourth opening 122, 124, 132, 134 can have closed perimeters. The first and fourth openings 122, 134 can define a third fastener bore 136 along an axis B at an angle α relative to the longitudinal axis A, as shown in FIG. 1A.

The bone fastener 104 can be oriented along the axis B passing through the third fastener bore 136 of the IM implant 102. The bone fastener 104 can extend from a proximal lateral position near the greater trochanter 82 to a more distal medial position near the lesser trochanter 84 of the femur 80, as shown in FIG. 2. The bone fastener 104 can include a head 106 and a threaded shaft 108 with threads, ridges or other anchoring formations. One or more fasteners 104', generally similar in structure to the bone fastener 104, can be inserted through the distal portion 114 of the IM implant 102 for fixation to the distal femur.

Figure 3:
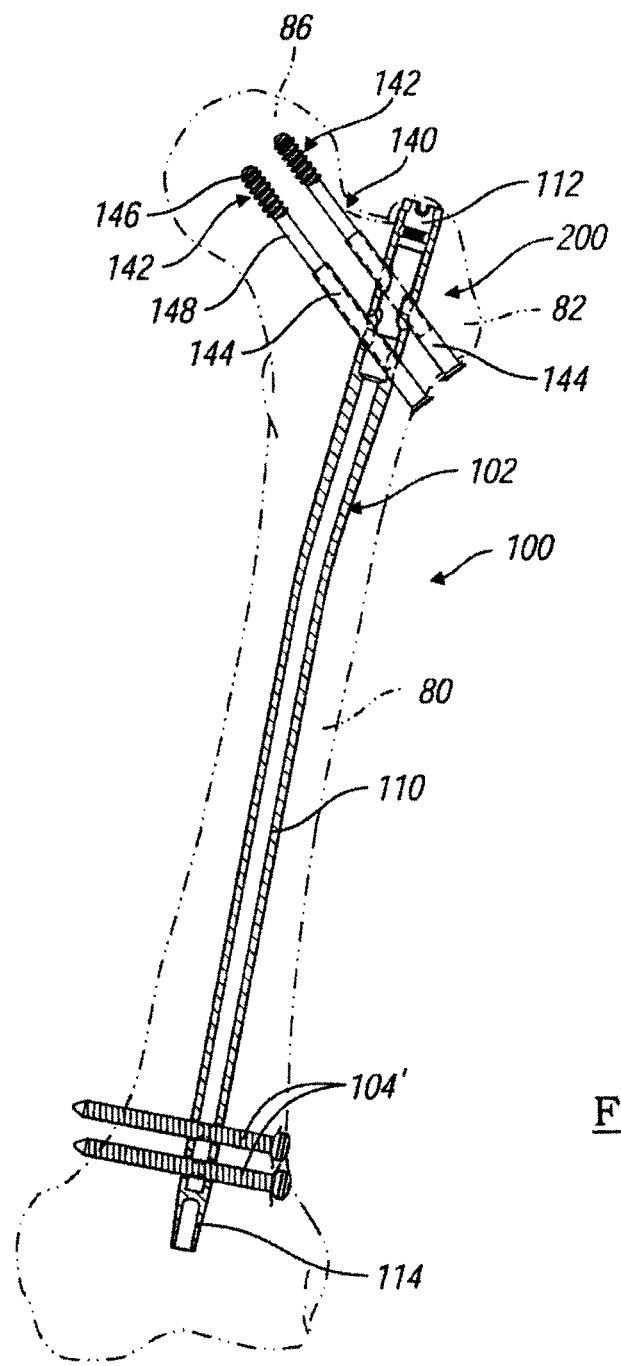
FIG. 3 is an environmental view of a fixation device according to the present teachings, illustrating a trochanteric procedure with reconstruction fixation fasteners.
Figure 4:
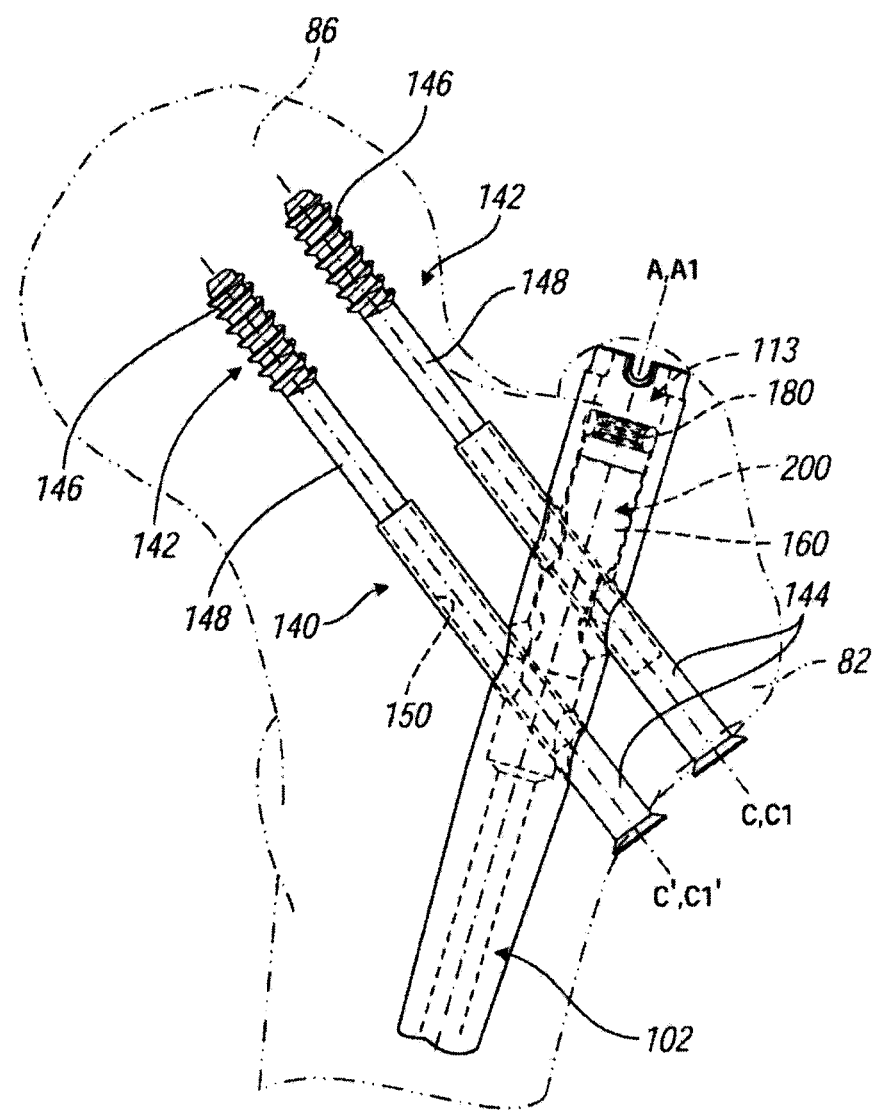
FIG. 4 is an enlarged view of a detail of the fixation device of FIG. 3.
Figure 4A:
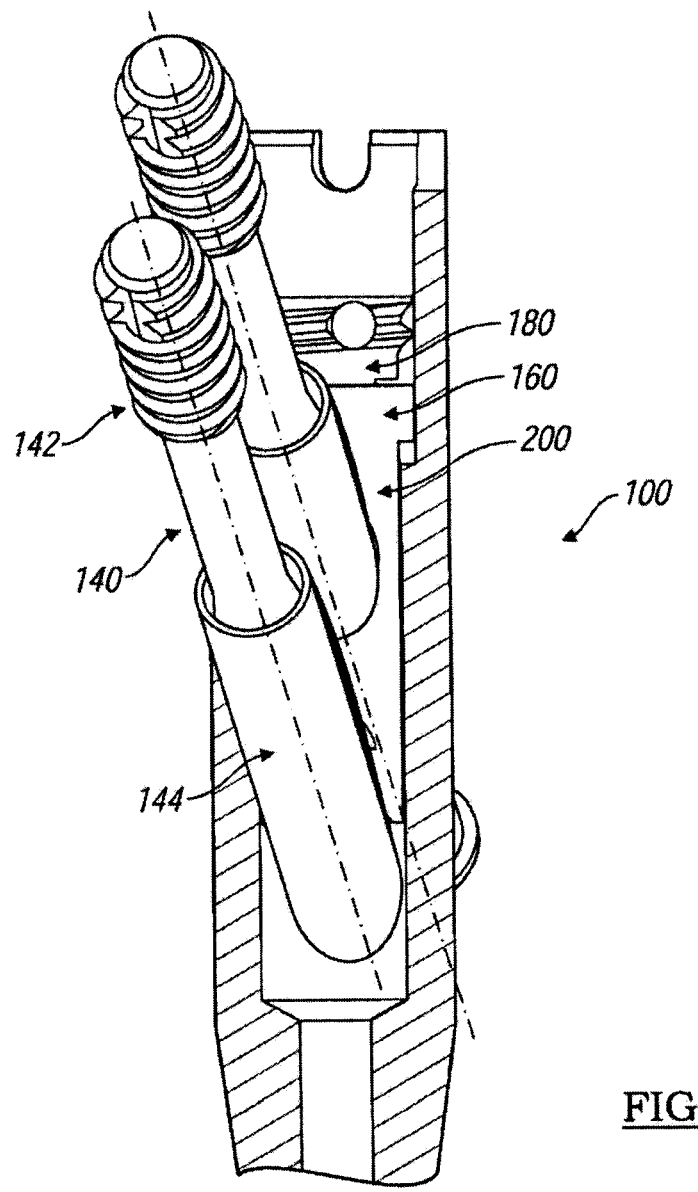
FIG. 4A is a partial cut-out view of a detail of the fixation device of FIG. 3

Referring to FIGS. 1A, 3 and 4, another exemplary fixation device 100 according to the present teachings is shown implanted in the femur 80 for a reconstructive trochanteric procedure. Two reconstruction fasteners 140 can be oriented along the directions defined by the first and second axes C and C' passing through the corresponding first and second fastener bores 120, 130 of the IM implant 102. Accordingly, the reconstruction fasteners 140 can be oriented at respective first and second angles β and β' relative to the longitudinal axis A, as described above. The reconstruction fasteners 140 can extend from the vicinity of the greater trochanter 82 through the femoral neck 88 and into the femoral head 86. Each reconstruction fastener 140 can be a two-piece telescoping component including a sleeve 144 having a longitudinal bore 150 and a lag screw 142 that can pass through the bore 150 of the sleeve 144 and can slide relative to the sleeve 144. The lag screw 142 can include an unthreaded portion 148 receivable in the bore 150 of the sleeve 144, and a bone anchoring or threaded portion 146.

Referring to FIGS. 1-6C, either the bone fastener 104 or the reconstruction fasteners 140 can be secured to the IM implant 102 using a securing device 200. The securing device 200 can include a telescopic insert or movable member 160, and a locking member 180, such as a set screw. The movable member 160 can be adapted for locking multiple fasteners to the IM implant 102, as shown in FIGS. 2 and 4. The movable member 160 can include a circular longitudinal bore 162 defining longitudinal axis "A1". When the movable member 160 is inserted into the longitudinal bore 113 of the IM implant 102, the longitudinal axes A and A1 can substantially coincide. The movable member 160 can define first and second guiding bores 164, 166 oriented along the first and second axes C1, C1', as shown in FIG. 5C. When the movable member 160 is inserted into the longitudinal bore 113 of the IM implant 102, the first and second axes C, C' of the intramedullary implant can substantially coincide with the first and second axes C1, C1' of the movable member 160.

Figure 5A:
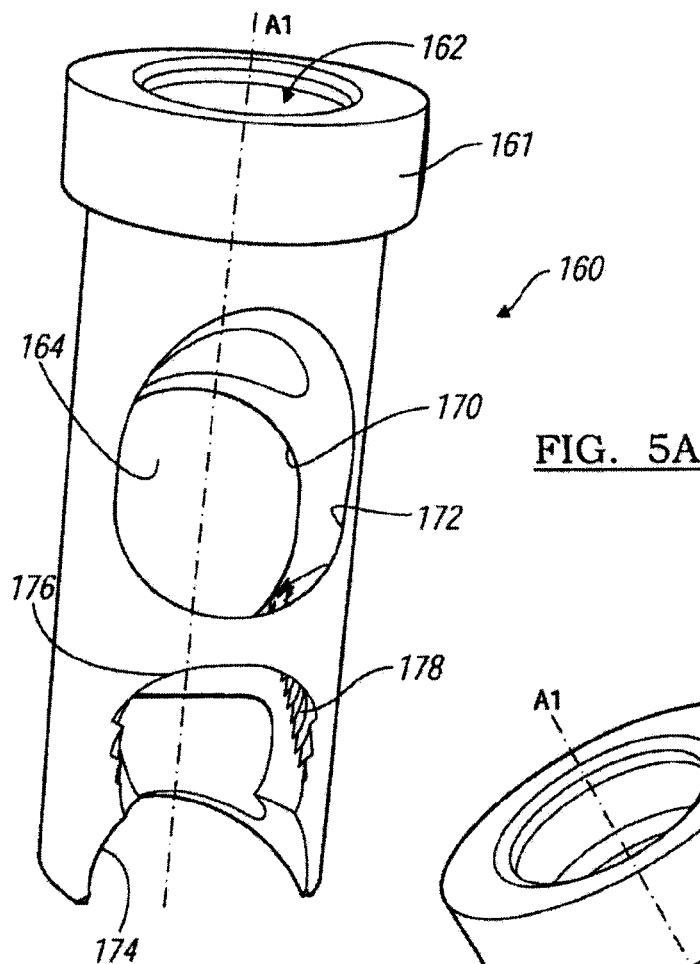
FIG. 5A-C are various perspective view of an insert for the fixation devices of FIGS. 2 and 3.
Figure 5B:
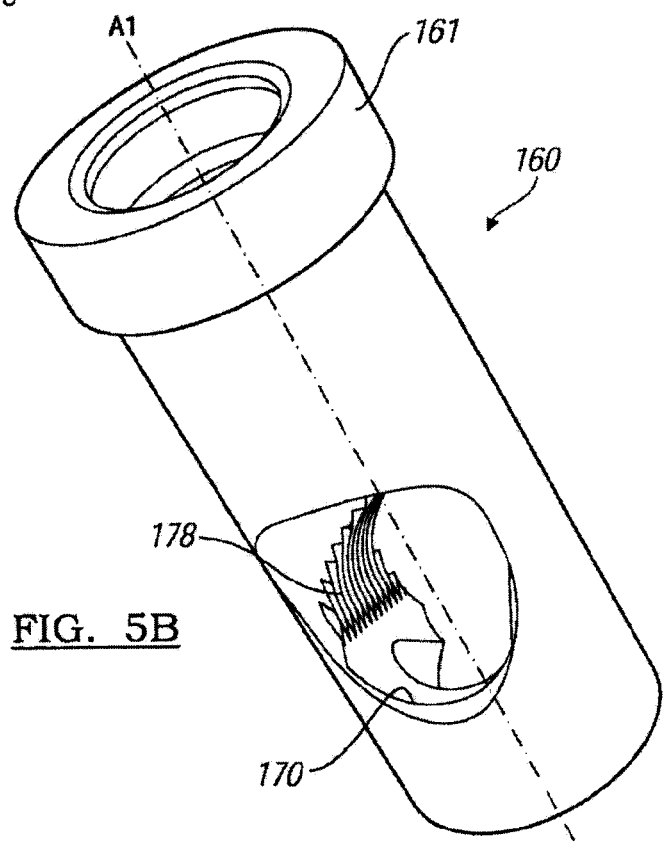
Figure 5C:
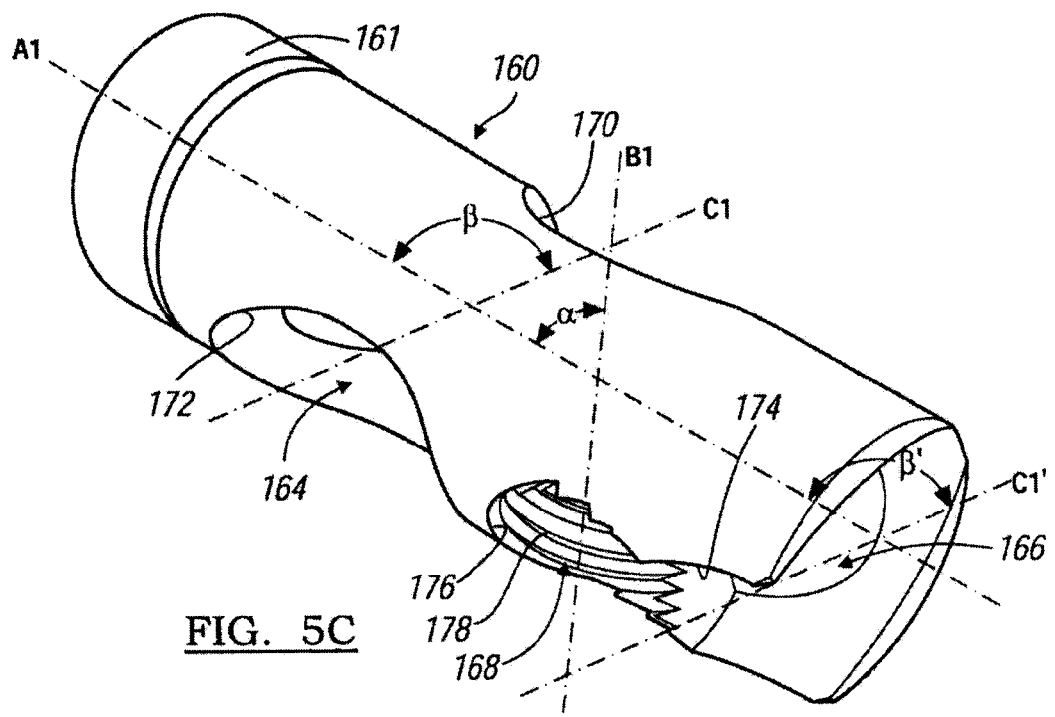

The first guiding bore 164 can be fully enclosed within the movable member 160 and defined by first and second openings 170, 172. The first and second opening 170, 172 can be axially offset, can have closed perimeters and can be formed on opposing sides of the movable member 160 along the first axis C1. The second guiding bore 166 can be partially enclosed and defined by a third opening 174 having an open perimeter, as shown in FIG. 5C. It will be appreciated, however, that the second guiding bore 166 can also be fully enclosed and defined by two opposing openings along the axis C1' of the movable member 160. The first and second reconstruction fasteners 140 can be inserted through the first and second guiding bores 164, 166 of the movable member 160 and through the corresponding first and second fastener bores 120, 130 of the IM implant 102 along the axes C, C', as shown in FIG. 4.

The movable member 160 can also include a third guiding bore 168 defined along axis B1 and at an angle α relative to the longitudinal axis A1. When the movable member 160 is inserted into the longitudinal bore 113 of the IM implant 102, the axes B and B1 can substantially coincide. The third guiding bore 168 can be defined by the first opening 170 and an opposite-side and longitudinally offset and open-perimeter fourth opening 176. The perimeter of the fourth opening 176 can intersect the perimeter of the third opening 174, such that the fourth and third openings 174, 176 can communicate, as shown in FIGS. 5A and 5C. A bone fastener 104 can be received in the third guiding bore 168 passing through the third fastener bore 136 of the IM implant 102, when reconstruction fasteners 140 are not used, as shown in FIG. 2. Ridges or other engagement formations 178 can be provided in portions of any guiding bores of the movable member 160 for engaging corresponding threads or ridges of the threaded shaft 108 of bone fasteners 104. Ridges 178 are illustrated, for example, in FIGS. 5A-5C in connection with trochanteric femoral procedures, in FIGS. 9A-9C for retrograde femoral procedures, in FIGS. 14A and 14B for piriformis femoral procedures, and in FIGS. 16, 17B, 18A and 18C for tibial procedures. The ridges 178 allow removal or backing out of an individual bone fastener 104 by rotating the head 106 of bone fastener 104 in a counterclockwise direction with a driver, for example, while the IM implant 102 and the other bone fasteners 104 remain secured in place with the securing device 200 in a locked position. Accordingly, any bone fastener 104 can be removed or backed out without accessing the top of the IM implant 102 for disengaging the bone fastener 104. Therefore, the procedure described below in connection with FIGS. 19A and 19B for unlocking the securing device 20 need not be used for backing out or completely removing one of the bone fasteners 104.

Figure 5D:
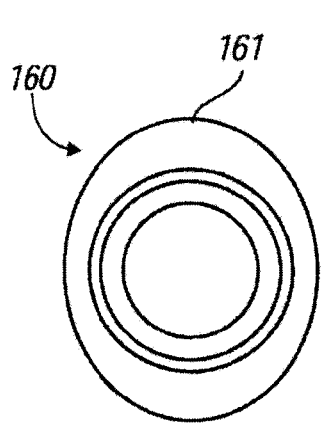
FIG. 5D is a top view of the insert if FIG. 5A.
Figure 5E:
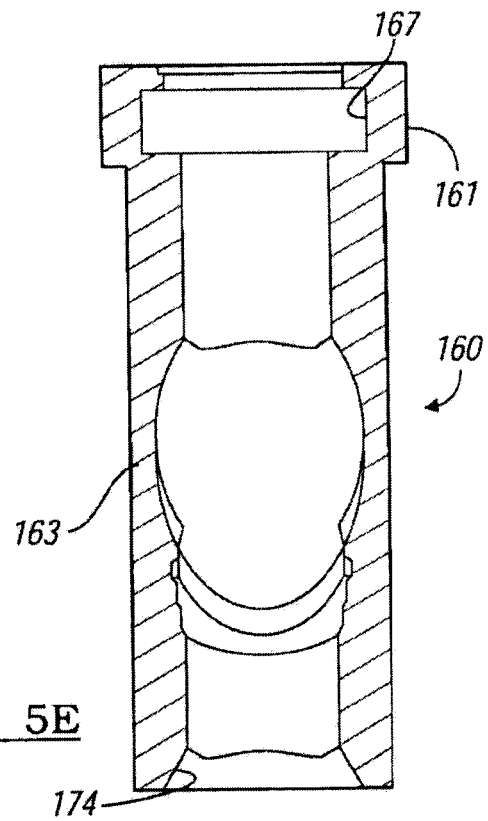
FIG. 5E is a sectional view of the insert of FIG. 5A.
Figure 15:
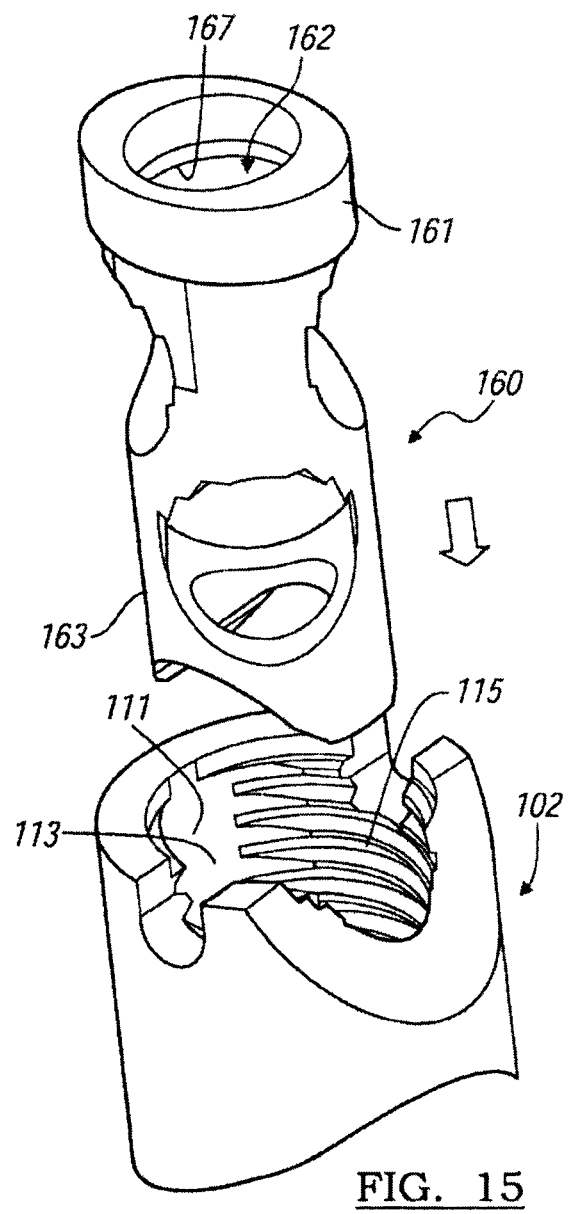
FIG. 15 is a partially exploded perspective view of a portion of a fixation device according to the present teachings.

Referring to FIGS. 5D and 5E, the movable member 160 can include a proximal end portion having an outer surface 161 with elliptical or elongated cross-section, and a body with a circular cylindrical surface 163, as shown in FIGS. 5D and 5E. The outer surface 161 of the movable member 160 can mate with the proximal inner surface 111 of the proximal longitudinal bore 113 providing a keyed insertion, such that the movable member 160 can be inserted in the proximal longitudinal bore 113 in either one of two directions that are 180 degrees apart, as illustrated in FIG. 15 in connection with a movable member 160 and an IM implant 102 for a tibial procedure described below. The longitudinal inner bore 162 of the movable member 160 can be circular.

Figure 6A:
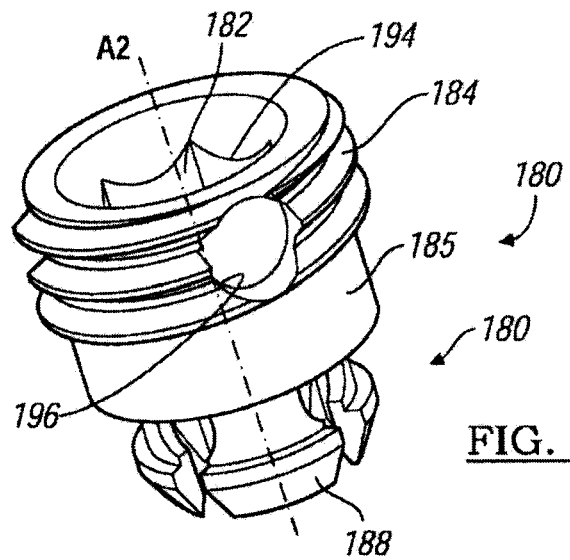
FIG. 6A is a perspective view of a locking member according to the present teachings.
Figure 6B:
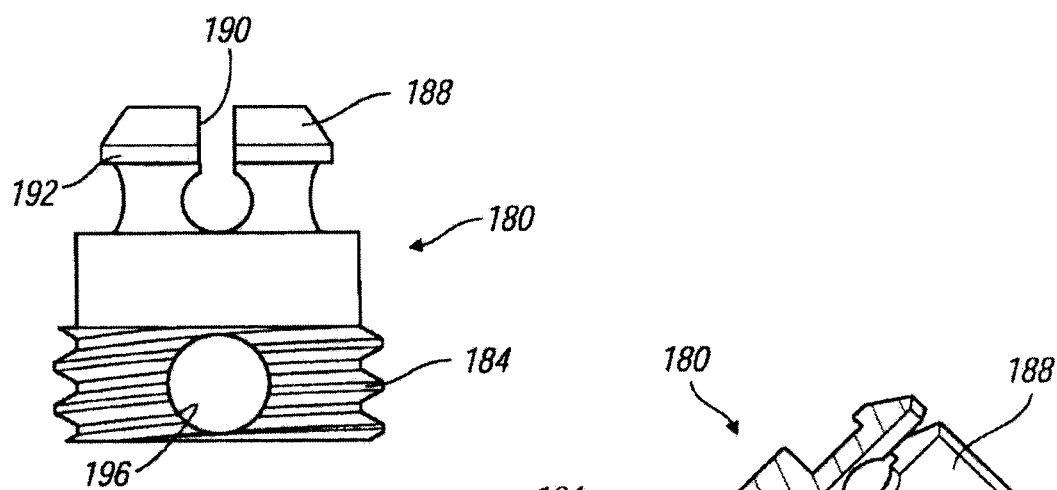
FIG. 6B is a side view of the locking member of FIG. 6A.
Figure 6C:
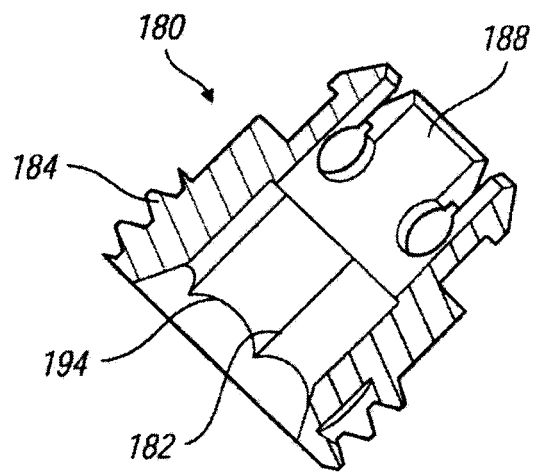
FIG. 6C is a sectional view of the locking member of FIG. 6A.
Figure 7:
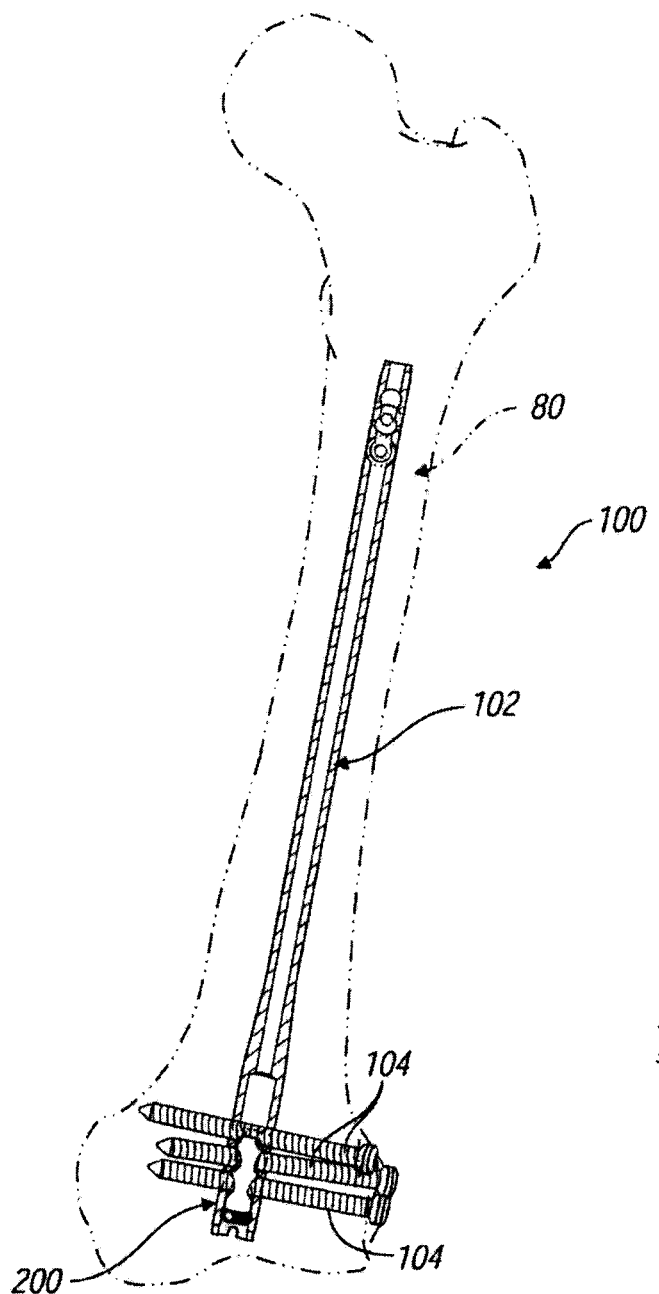
FIG. 7 is an environmental view of a fixation device according to the present teachings, illustrating a retrograde femoral procedure.
Figure 16:
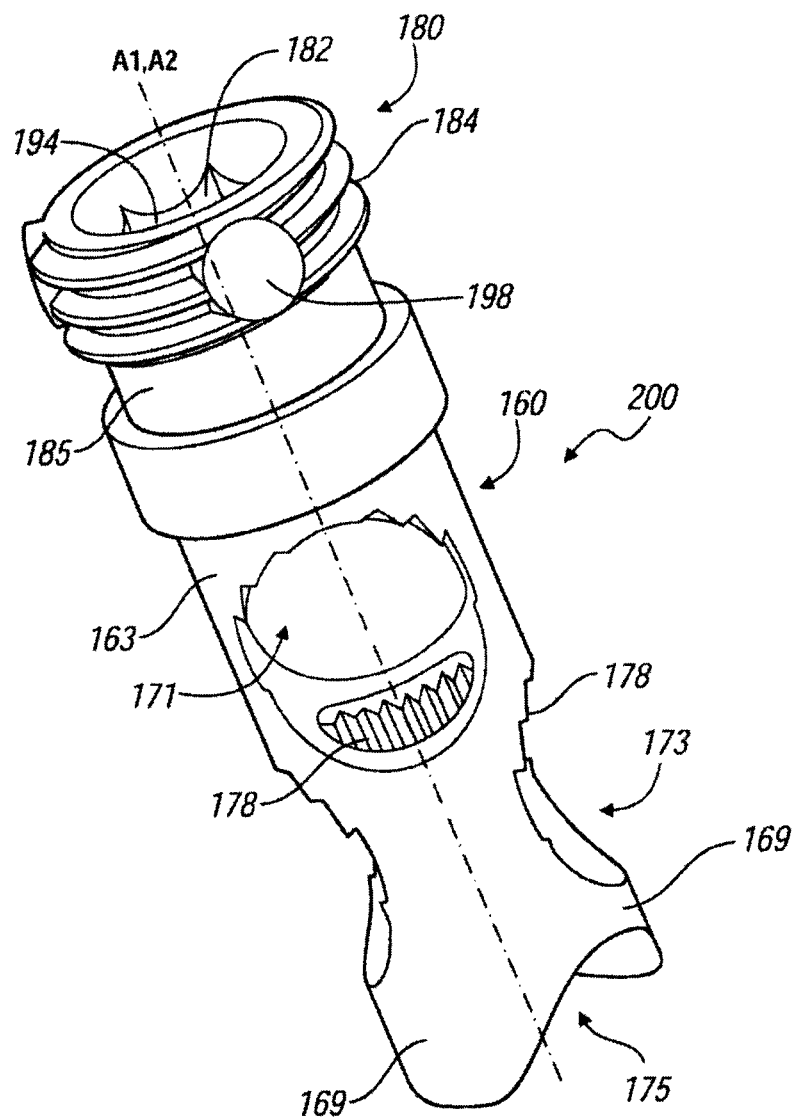
FIG. 16 is a perspective view illustrating an insert assembled with a locking member for an intramedullary nail according to the present teachings.

Referring to FIGS. 6A-6C, various views of a locking member 180 are illustrated. The locking member 180 can include a longitudinal bore 182 along a longitudinal axis A2. The locking member 180 can include a threaded portion 184 and an unthreaded cylindrical portion 185. The threaded portion 184 can threadably engage a threaded inner surface 115 of the proximal longitudinal bore 113 of the IM implant 102, as shown in FIGS. 15 and 16 in connection with a movable member 160 and IM implant 102 for a tibial procedure described below. The locking member 180 can also include a distal flexible or resilient portion 186 defined by a plurality of legs 188 extending from the unthreaded portion 185 of the locking member 180 and separated by slots 190. The resilient portion 186 can define a step or flange 192 that can be retained into a groove 167 of the movable member 160, shown in FIG. 5E, for example, when the resilient portion 186 is snap-fitted into the longitudinal bore 162 of the movable member 160, as shown in FIGS. 15 and 16.

The locking member 180 can also include a driver engagement formation 194 in a proximal portion of the bore 182 for engaging a driver 500. The driver 500 can be rotated for threadably engaging the locking member 180 with the IM implant 102, such that advancement of locking member 180 and corresponding advancement of the movable member distally or proximally can engage or disengage the movable member 160 from corresponding bone fasteners, such as bone fasteners 104, as shown in FIGS. 19A, 19B, 18A and 18B, in connection with a tibial procedure, as described in further detail below. The locking member 180 can also include holes or other openings 196 that interrupt the threads of the threaded portion 184. The openings 196 can be plugged with thread locks 198 that prevent further engaging or disengaging movement between the locking member 180 and the IM implant 102, thereby securing the corresponding position of the movable member 160 relative to the IM implant 102 and the bone fasteners 104 or reconstructive fasteners 140. The thread locks 198 can be made of polyethylene, for example.

Figure 8:
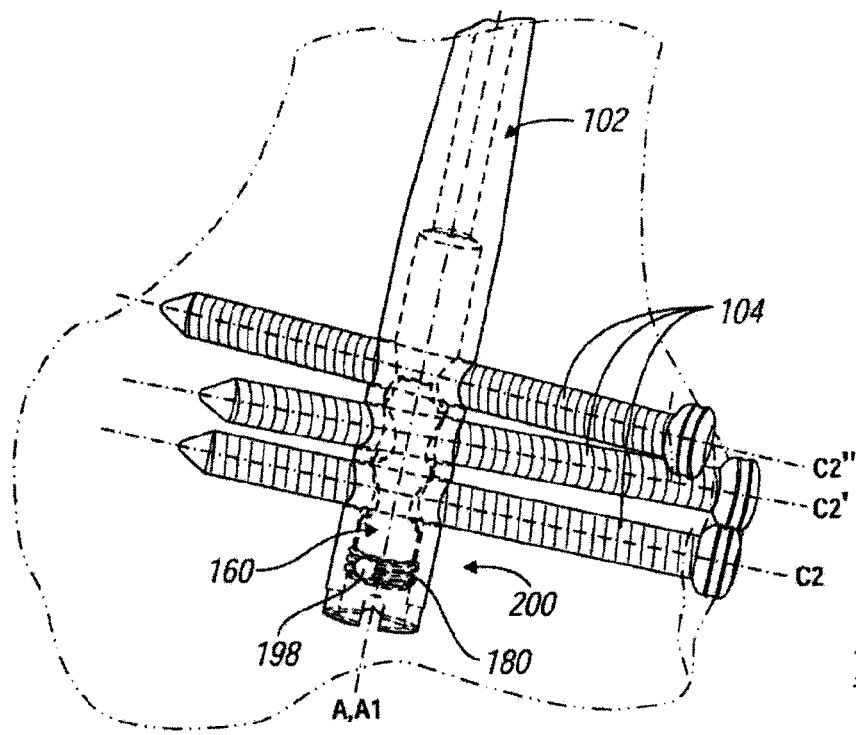
FIG. 8 is an enlarged view of a detail of FIG. 7.
Figure 8A:
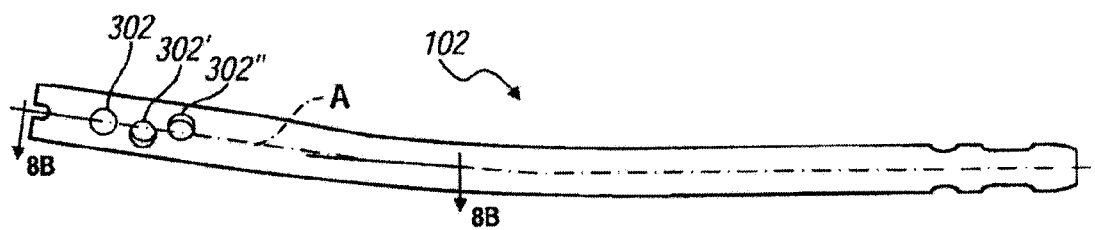
FIG. 8A is a side view of an intramedullary implant of the fixation device of FIG. 7.
Figure 8B:
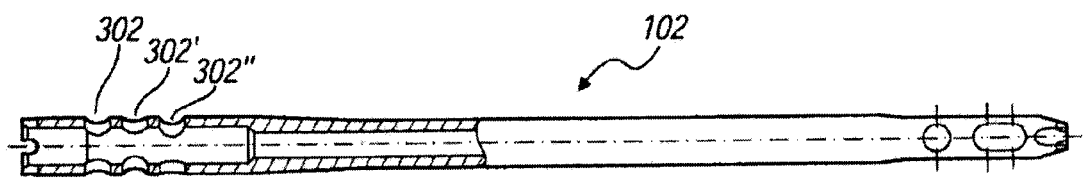
FIG. 8B is another side view of an intramedullary implant of the fixation device of FIG. 7, shown partially in section.

Referring to FIGS. 7-9B, an exemplary fixation device 100 is illustrated for a retrograde interlocking femoral fixation procedure. The retrograde IM implant 102 can be inserted in the distal portion of the femur 80 in a retrograde direction and can interlock at least up to three bone fasteners 104 using the movable member 160 and the locking member 180 of the securing device 200. The retrograde IM implant 102 can define a plurality of through-bores, for example first, second and third bores 302, 302', 302" oriented transversely or at other different angles relative to longitudinal axis A of the retrograde IM implant 102. Some of the bores 302, 302', 302" can circumferentially offset relative to the longitudinal axis A, or can be aligned along the longitudinal axis A, as shown in FIG. 8A. The movable member 160 can include corresponding first, second and third guiding bores 304, 304', 304" oriented along first, second and third axes C2, C2', and C2", as shown in FIGS. 8 and 9A. The first and second guiding bores 304, 304' can have closed perimeters, while the third guiding bore 304" can have an open perimeter defining a pair of opposing legs 306. Some of the first, second and third guiding bores 304, 304', 304" can be aligned or circumferentially offset relative to one another or relative to the longitudinal axis A1, and can be parallel or non-parallel. The structure and function of the locking member 180 and other features of the securing device 200 and retrograde IM implant 102 are similar to those described above in connection with trochanteric procedure illustrated in FIGS. 1-6C and are not repeated.

Figure 11:
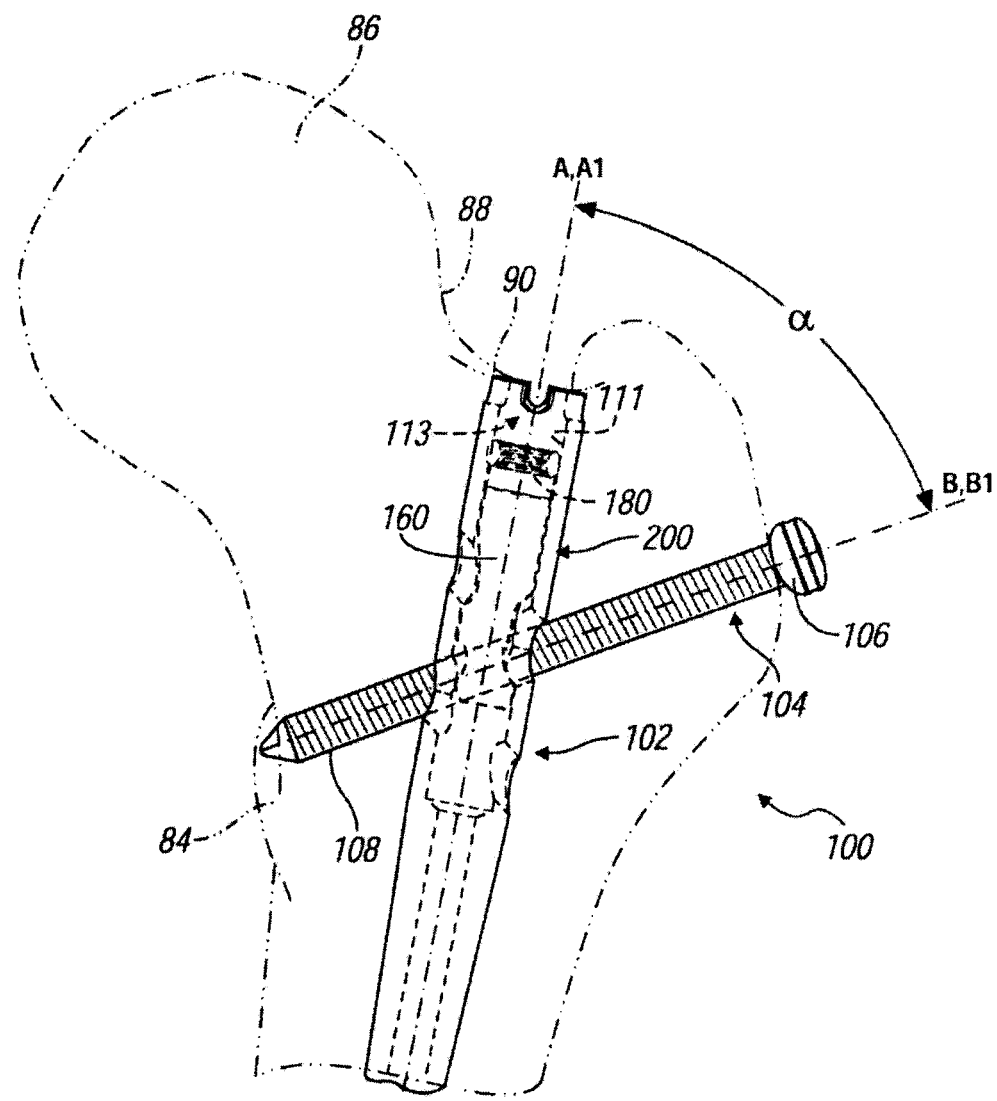
FIG. 11 is an enlarged view of a detail of FIG. 10.
Figure 12:
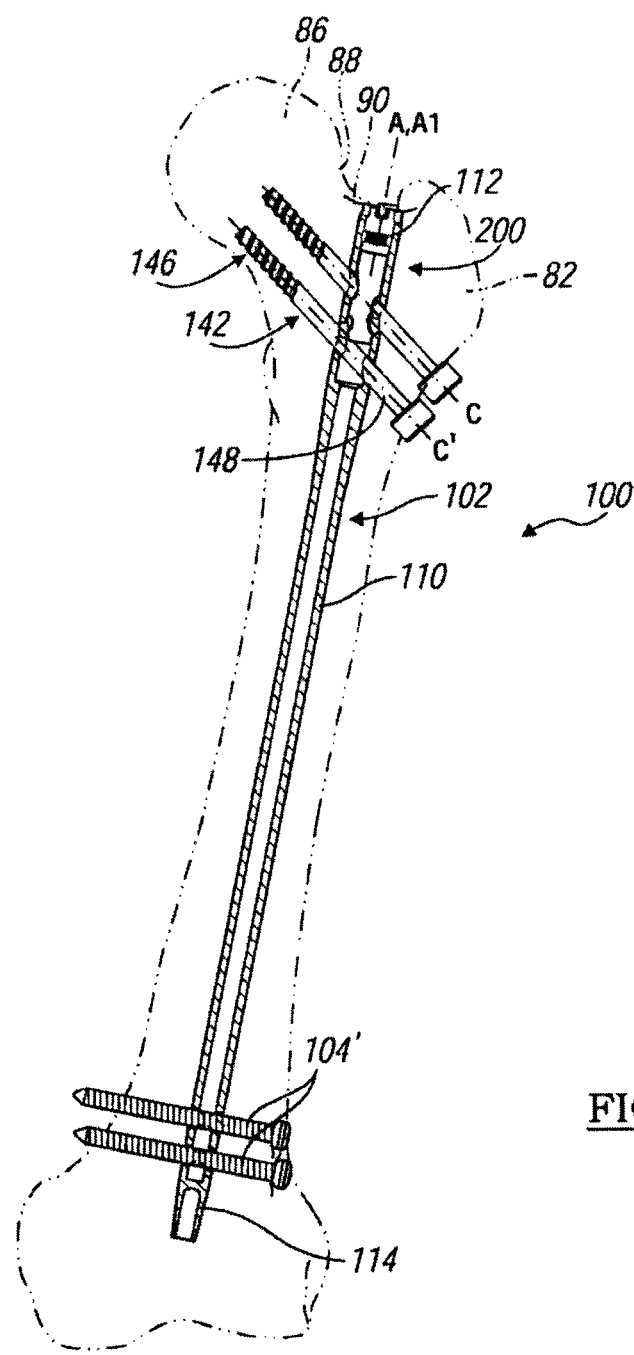
FIG. 12 is an environmental view of a fixation device according to the present teachings, illustrating a piriformis procedure with reconstruction fixation fasteners.
Figure 13:
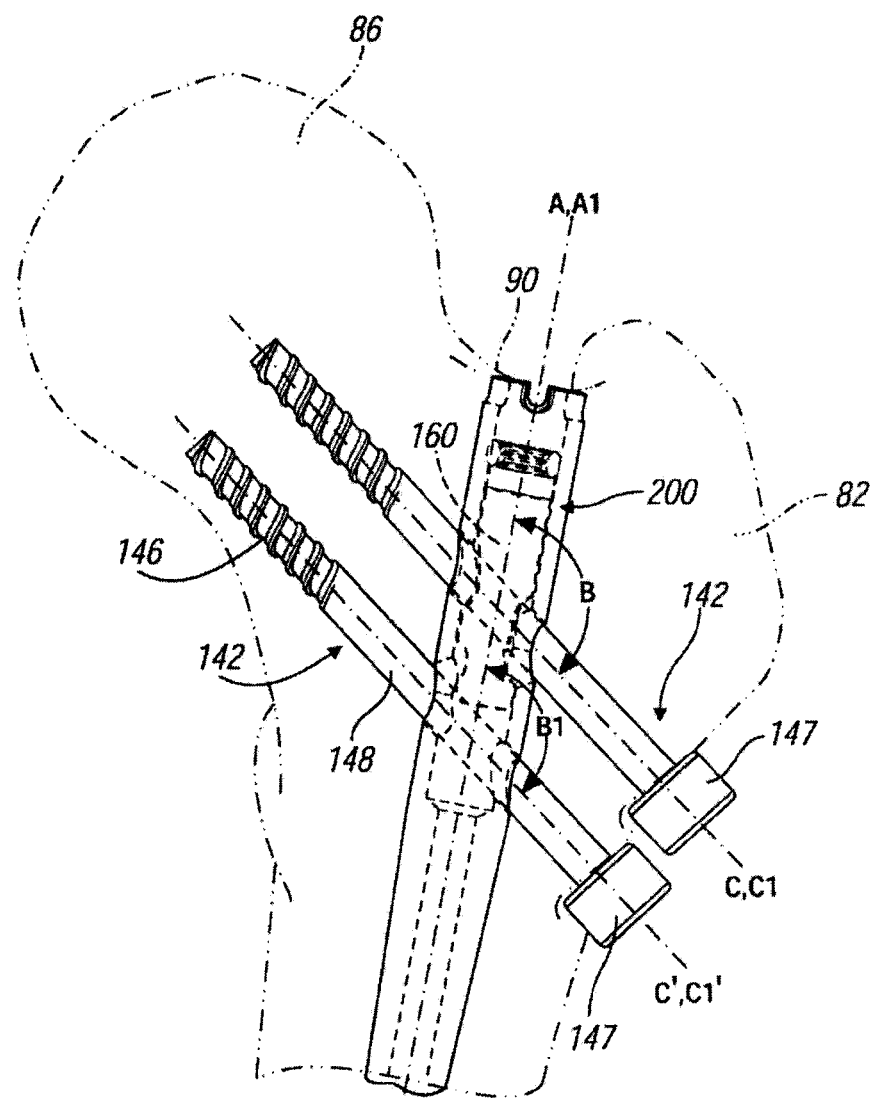
FIG. 13 is an enlarged view of a detail of FIG. 12.
Figures 14A, 14B:
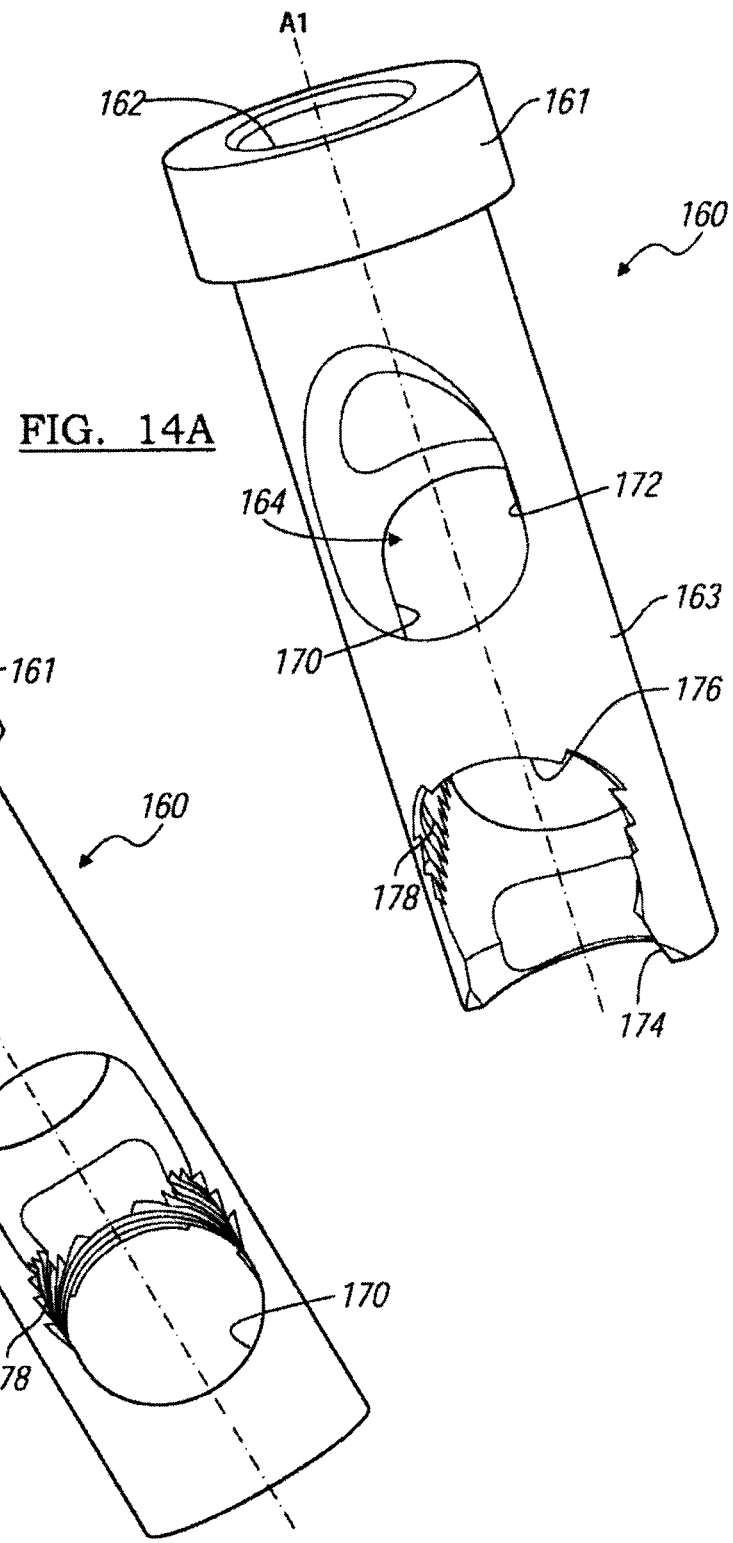
FIGS. 14A and 14B are perspective views of an insert for the fixation devices of FIGS. 10 and 12.
Figure 14C:
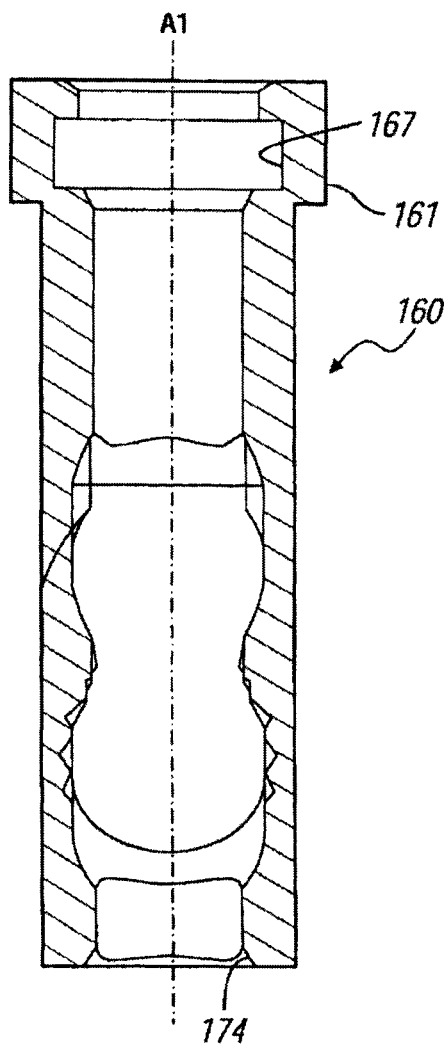
FIG. 14C is a sectional view of the insert of FIG. 14A.

Referring to FIGS. 10-14B, an exemplary fixation device 100 according to the present teachings is illustrated for piriformis femoral procedures. FIGS. 10 and 11 illustrate an interlocking piriformis fixation procedure, and FIGS. 12 and 13 illustrate a reconstruction piriformis fixation procedure. The piriformis IM implant 102, the piriformis bone fastener 104 and the piriformis securing device 200 are similar to the corresponding components described in connection with the trochanteric procedures illustrated in FIGS. 1-6C and their description is not repeated, except to note different or additional elements. The piriformis IM implant 102 can be configured for entry through the piriformis fossa 90 near the greater trochanter 82, as shown in FIG. 11. The reconstruction fasteners 140 can include single-piece piriformis lag screws 142 having the threaded portion 146, the unthreaded portion 148 and a head 147, as shown in FIG. 13. The piriformis lag screws 142 can pass through the piriformis IM implant 102 along axes C, C', and through the piriformis movable member 160 of piriformis securing device 200 along corresponding axes C1, C1' at angles β and β', which can be equal or different. The piriformis lag screws 142 can be also be used with sleeves 144 in a telescopic manner, as described in connection with the trochanteric procedure illustrated in FIG. 4. Various views of the piriformis movable member 160 are illustrated in FIGS. 14A-14C using the same reference characters as used in FIGS. 5A-5E to describe similar elements.

Figure 17A:
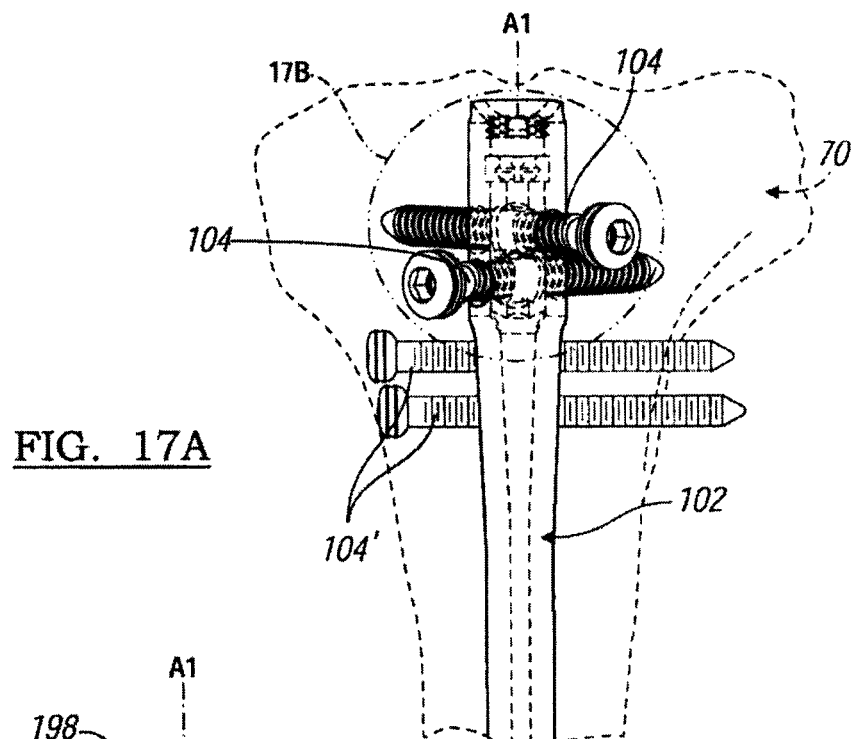
FIG. 17A is an environmental perspective view of a fixation device according to the present teachings, illustrating a femoral procedure with transverse fixation fasteners.
Figure 17B:
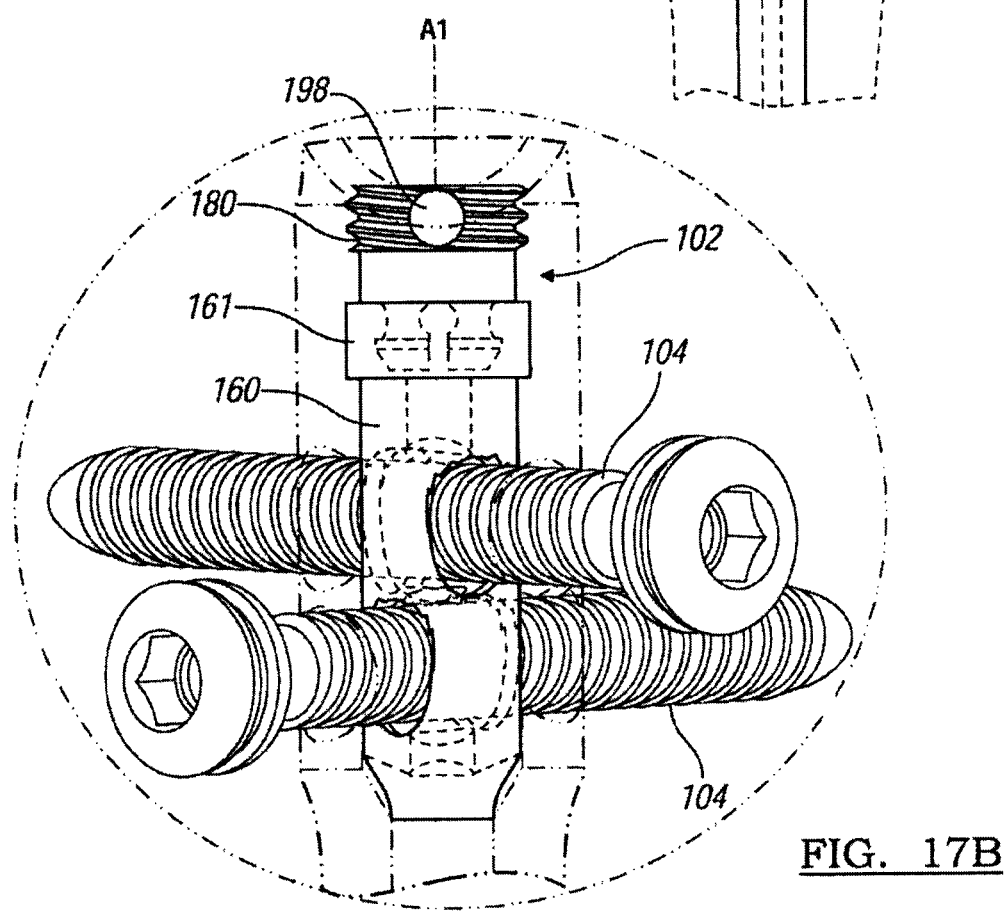
FIG. 17B is an enlarged detail of FIG. 17A.

Referring to FIGS. 15-16, aspects of a tibial securing device 200 and its insertion into a tibial IM implant 102, as discussed above, are illustrated for tibial procedures. The tibial movable member 160 can include first, second and third bores 171, 173, 175 transversely oriented relative to the longitudinal axis A1 of the movable member 160, and circumferentially offset relative to one another, as shown in FIGS. 16, 17A, and 17B. The first and second bores 171, 173 can have closed perimeters and receive corresponding bone fasteners 104, such as cortical screws that pass through corresponding bores of the tibial IM implant 102 for fixation into the tibia 70, as shown in FIGS. 17A and 17B. The third bore 175 can have an open perimeter defining two opposing legs 169.

Figures 18A, 18B:
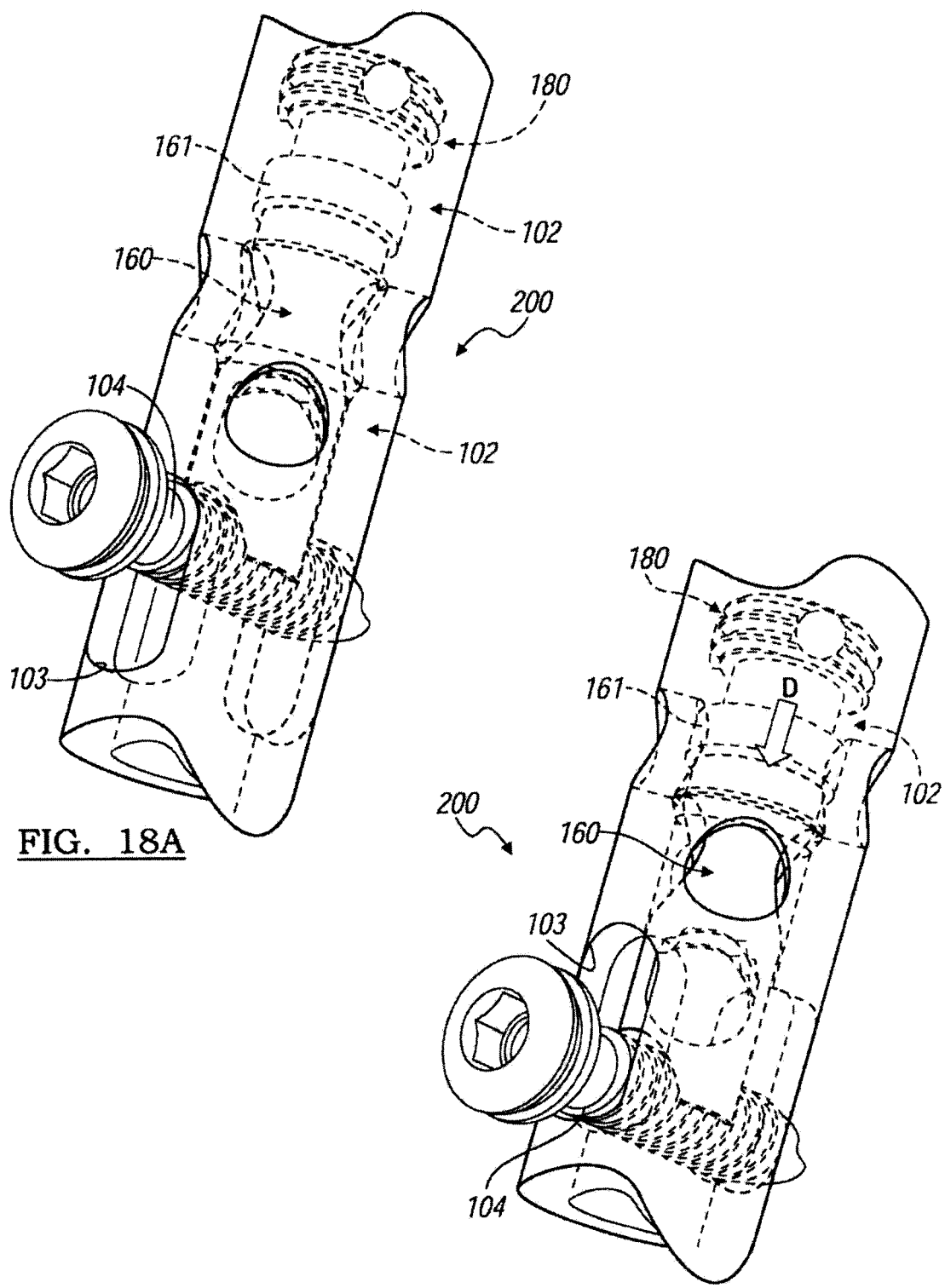
FIG. 18A is a perspective view illustrating a first position of an insert for an intramedullary nail according to the present teachings.
FIG. 18B is a perspective view illustrating a second position of the insert of FIG. 18A.

Referring to FIGS. 18A and 18B, use of the securing device 200 for active compression of fractures is illustrated. A bone fastener 104 can pass through the third bore 175 of the movable member 160 and through an elongated slot 103 of the IM implant 102. FIG. 18A illustrates the securing device 200 in a first position that allows dynamic movement along the slot 103. FIG. 18B illustrates the securing device 200 in a second position, in which the bone fastener 104 engages the distal wall of the slot 103. The movable member 160 can be moved from the first to the second position by rotation of the locking member 180, such that the locking member 180 threadably moves relative to the IM implant 102 and forces the movable member 160 to move distally in the direction of arrow D relative to the IM implant 102.

Figure 19A:
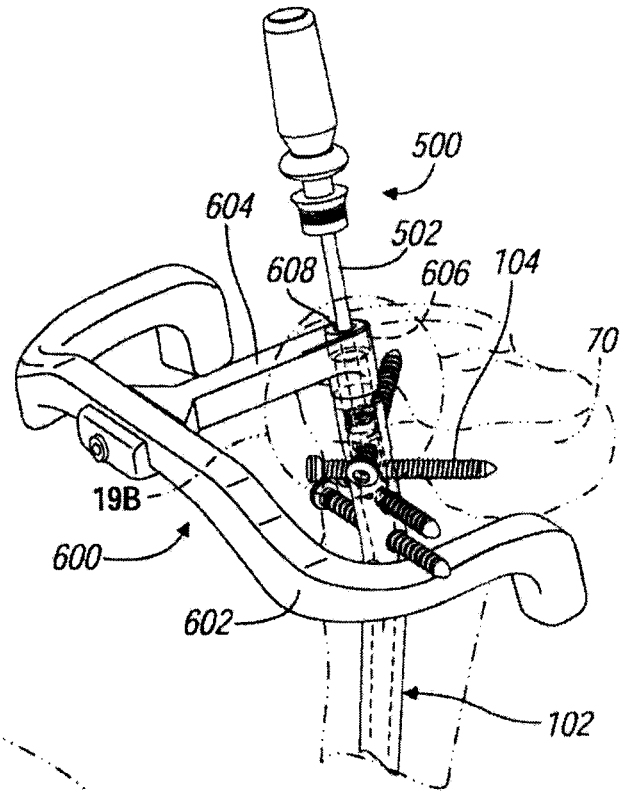
FIG. 19A is a perspective view illustrating instruments for engaging and disengaging an insert for an intramedullary implant according to the present teachings.
Figure 19B:
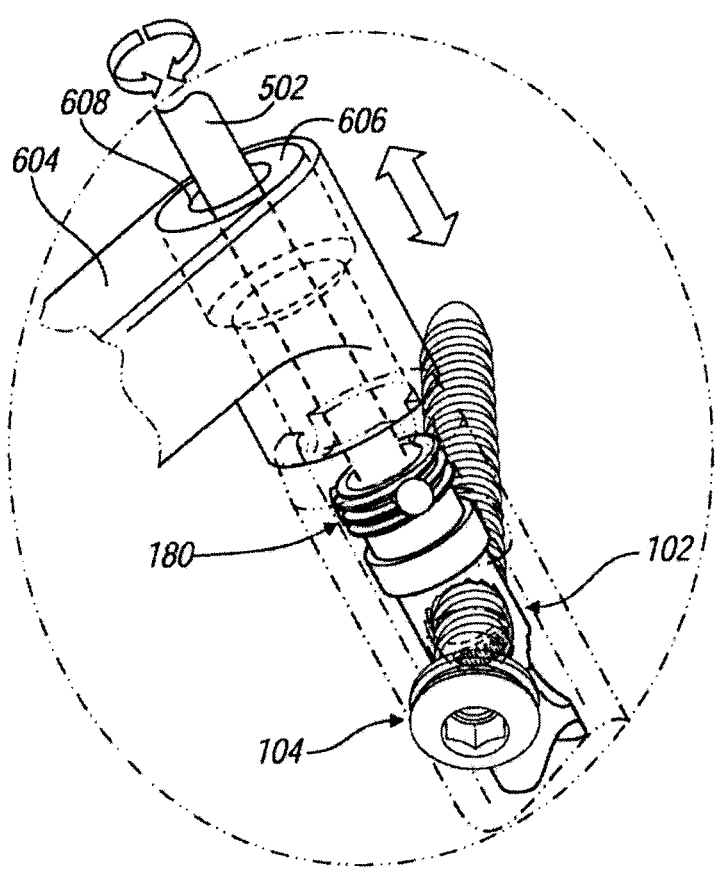
FIG. 19B is an enlarged detail of FIG. 19A.

Referring to FIGS. 19A and 19B, a targeting device 600 for engagement/disengagement of the securing device 200 is illustrated. The targeting device 600 can include a radiolucent targeting arm 602, a driving handle 604 and a cannulated connecting bolt 606 that connects the targeting device 600 to the IM implant 102. A driver 500 with a flexible driving shaft 502 can pass through the bore 608 of the connecting bolt 606 and engage the driver engagement formations 194 of the locking member 180. Rotating the driver shaft 502 clockwise or counterclockwise rotates the locking member 180 correspondingly, and correspondingly urges the movable member 160 distally to a position of engagement with the bone fasteners 104, or proximally to a position of disengagement. It will be appreciated, however, that any bone fastener 104 can be removed by rotating the bone fastener 104, such that the threaded shaft 108 of the bone fastener 104 moves relative to the ridges 178 of the corresponding bore of the movable member 160, while the securing device 200 remains in its locked position relative to the IM implant 102.

Referring to FIGS. 20-37, additional aspects of a fixation device 100 according to the present teachings are illustrated. As illustrated, FIGS. 20-23 may particularly pertain to piriformis procedures, FIGS. 24-32 may particularly pertain to trochanteric procedures, and FIGS. 33-37 may particularly pertain to retrograde procedures. In the following, similar elements are referenced with the same reference characters as those used in FIGS. 1-19B, and their corresponding description is not repeated. Additional or changed elements are described with new reference characters.

Figure 20:
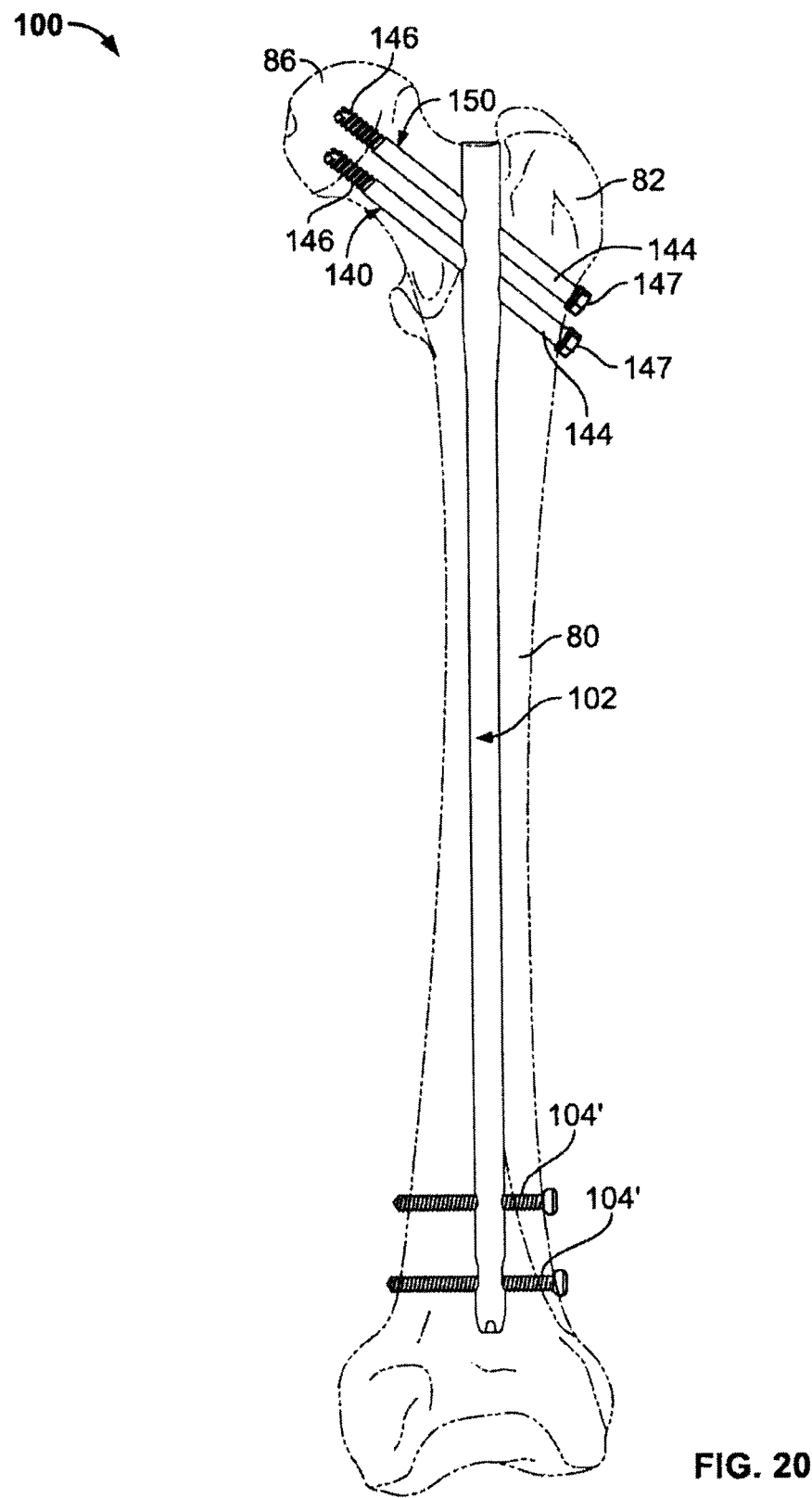
FIG. 20 is an environmental view of a fixation device according to the present teachings, illustrating a piriformis procedure with an intramedullary implant and reconstructive fixation fasteners in the proximal femur.
Figure 20A:
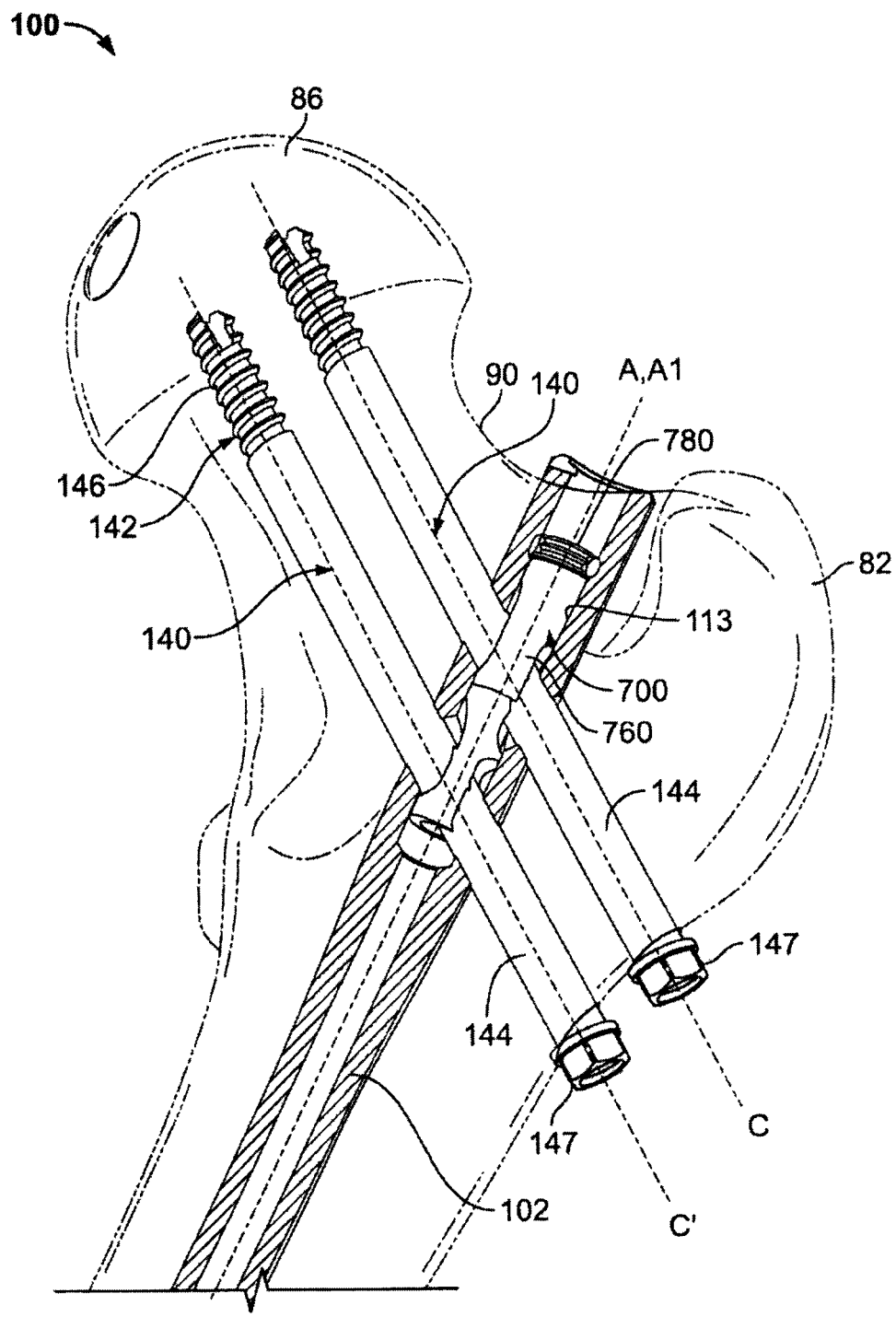
FIG. 20A is an enlarged view of a detail of FIG. 20.
Figure 23:
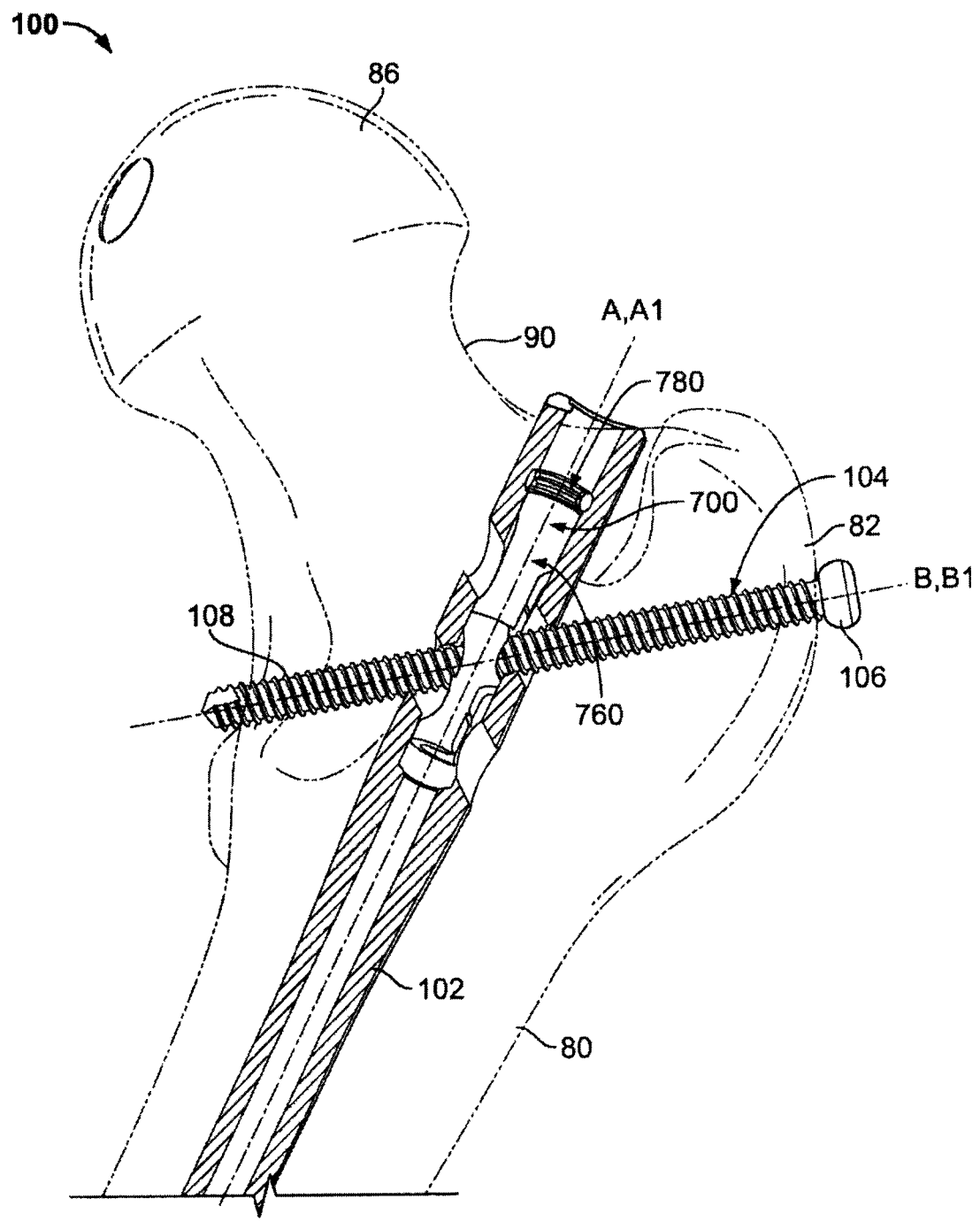
FIG. 23 is an environmental view of a fixation device according to the present teachings, illustrating a piriformis procedure with an intramedullary implant and an interlocking fixation fastener in the proximal femur.
Figure 24:
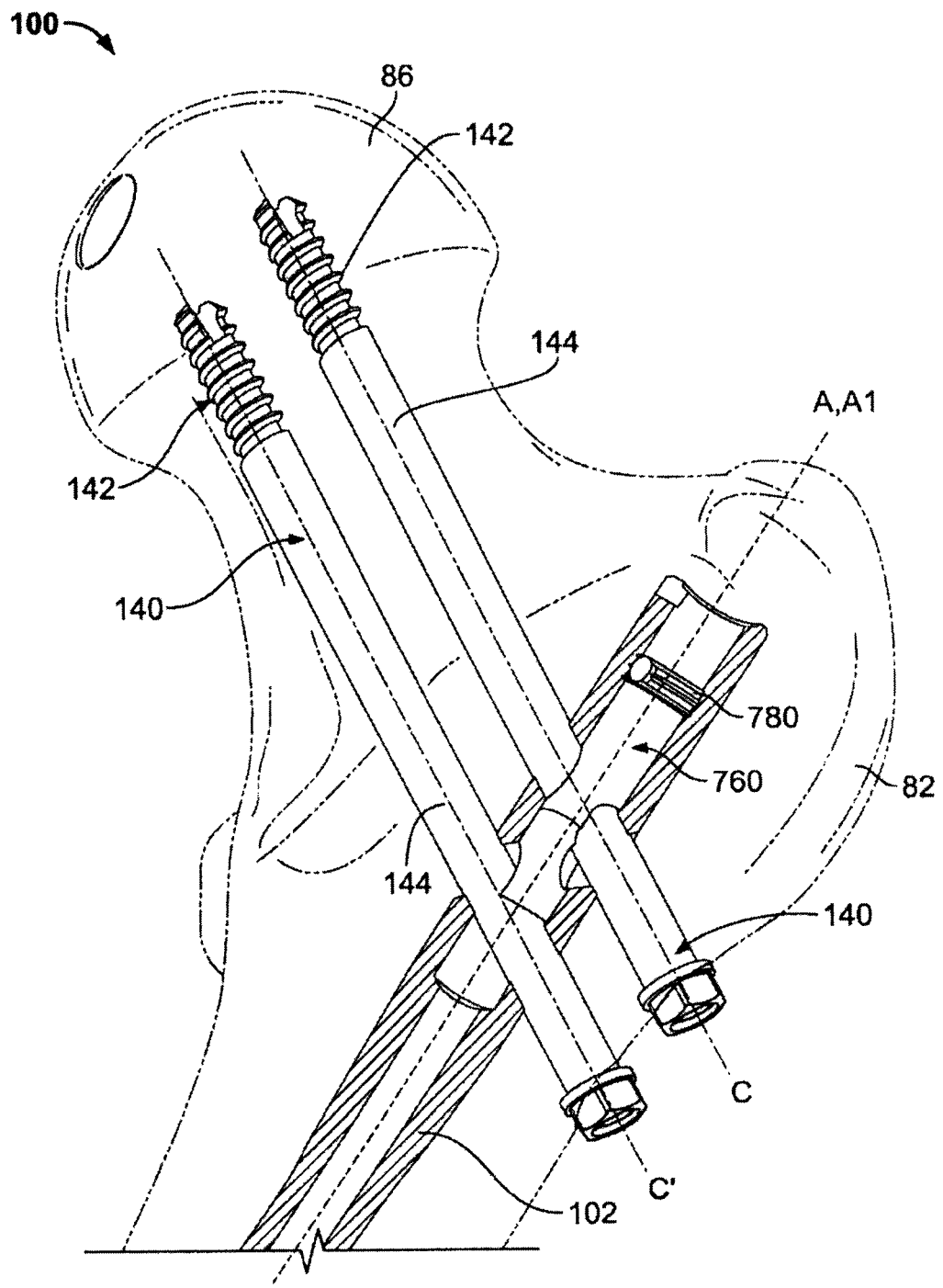
FIG. 24 is an environmental view of a fixation device according to the present teachings, illustrating a trochanteric procedure with an intramedullary implant and reconstructive fixation fasteners in the proximal femur.
Figure 31:
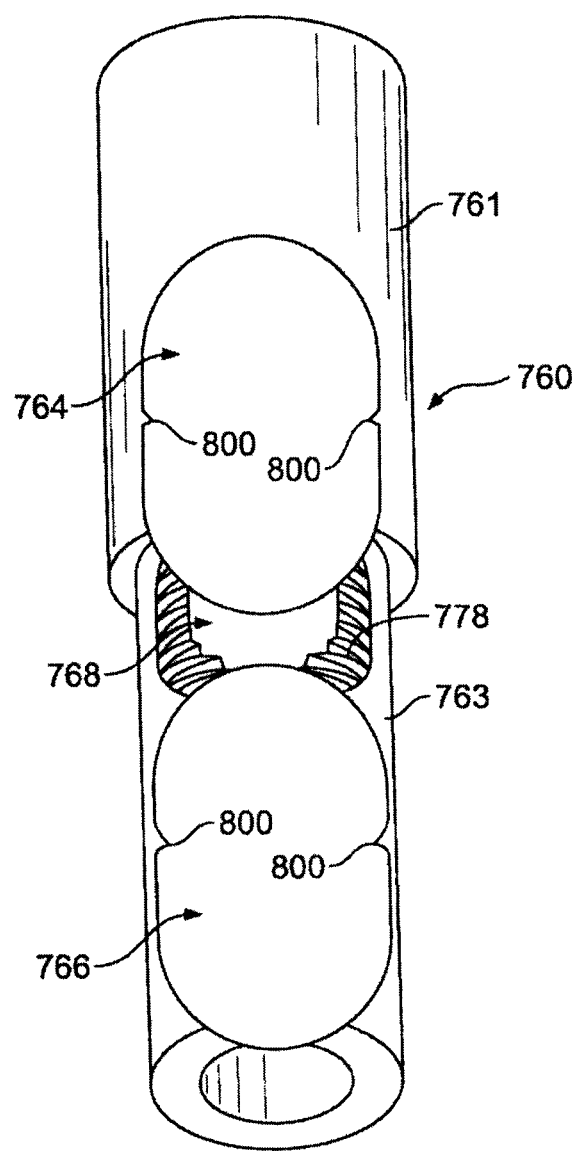
FIG. 31 is another perspective view of the insert of FIG. 26.
Figure 32:
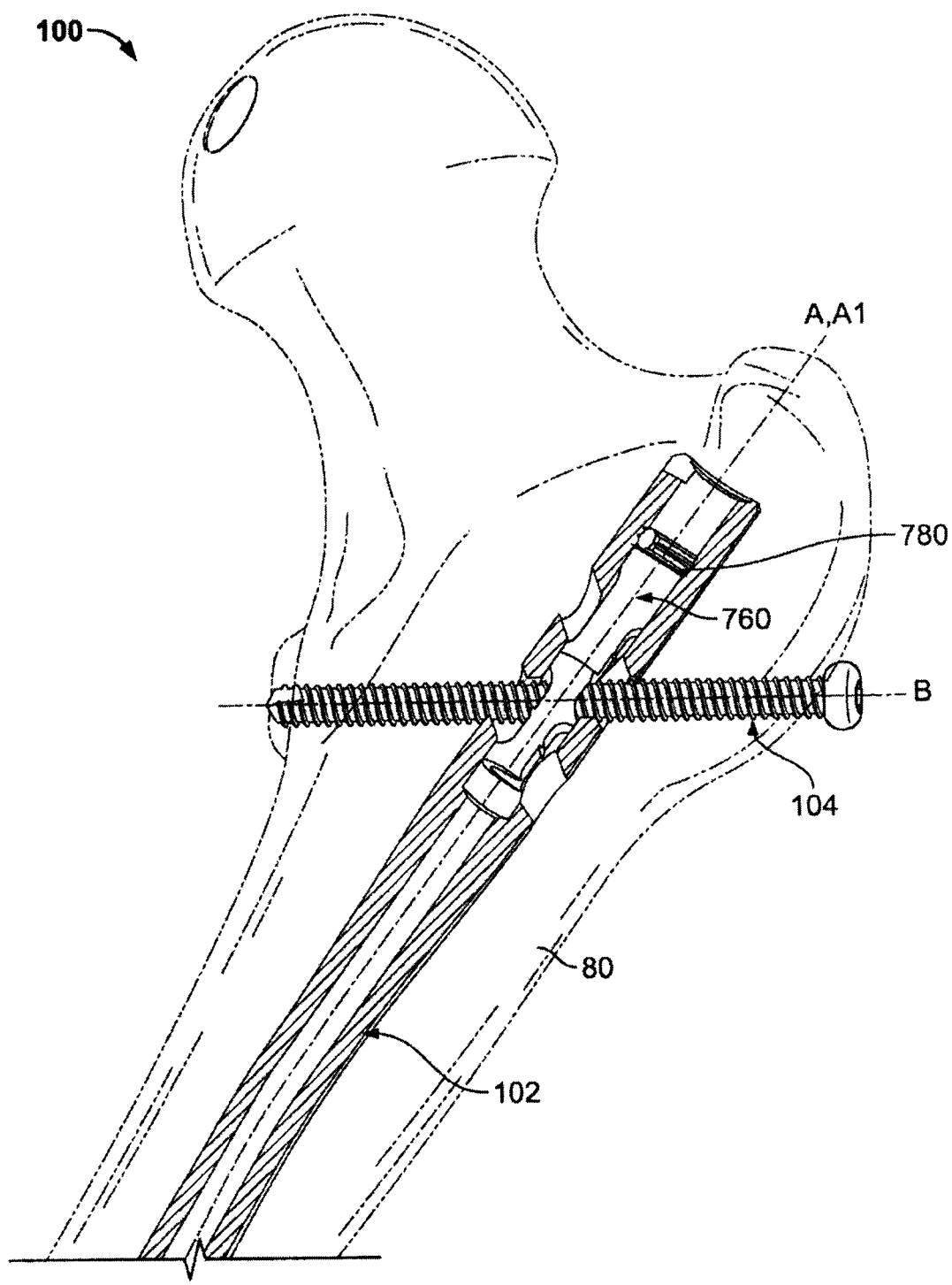
FIG. 32 an environmental view of a fixation device according to the present teachings, illustrating a trochanteric procedure with an intramedullary implant and an interlocking fixation fastener in the proximal femur.

Similarly to the fixation device 100 described in reference to FIGS. 1-19B, the fixation device 100 illustrated in FIGS. 20-32 includes an IM implant 102 and a securing device 700 received in the proximal longitudinal bore 113 of the IM implant 102 for securing two reconstructive fasteners 140, as shown in FIG. 20A (piriformis procedure) and FIG. 24 (trochanteric procedure), or a bone fastener 104, as shown in FIG. 23 (piriformis procedure) and FIG. 32 (trochanteric procedure). The securing device 700 can include a movable member or movable insert 760 and a locking member 780.

Similarly, the fixation device 100 illustrated in FIGS. 33-37 for a retrograde procedure can include an IM implant 102 and a securing device 900 received in the longitudinal bore 113 of the IM implant 102 for securing four bone fasteners 104. The securing device 900 can include a movable insert 960 and a locking member 780. Various aspects of the securing devices 700 and 900 are described below to the extent that they differ from the securing devices 200 illustrated and described above in connection with FIGS. 1-19B. The locking member 780 of the securing devices 700 and 900 is similar to the locking member 180 of the securing device 200, with elements designated 7XX in locking member 780 corresponding to elements designed 1XX in the locking member 180, as shown in FIGS. 25, 35, 6A and 16, for example.

Similarly, the movable insert 760 of the securing device 700 is similar to the movable member 160 of the securing device 200, with elements designated 7XX in movable insert 760 corresponding to elements designed 1XX in the movable member 160, as shown in FIGS. 21, 25, and 5C, for example.

The movable insert 760 of the securing device 700 can include first, second and third guiding bores 764, 766 and 768 similar to the corresponding guiding bores 164, 166, 168 of the securing device 200. Referring to FIGS. 20A, 21 and 22 for the piriformis procedure, and to FIGS. 24-31 for the trochanteric procedure, the movable insert 760 of the securing device 700 can include engagement formations in the form of first and second pairs of elongated locking tabs or strips 800. The locking strips 800 are flexible and deformable and allow retention of reconstructive fasteners 140 over a range of tolerance conditions. The first and second pairs of flexible strips 800 can be formed on opposing sides of the walls of the corresponding first and second guiding bores 764, 766, which can receive and guide the reconstructive fasteners 140 in reconstructive procedures. The flexible strips 800 can engage the substantially smooth and unthreaded outer surfaces of the cylindrical sleeves 144 of the reconstructive fasteners 140 along the orientations C, C', as shown in FIGS. 20A and 24. Engagement formations in the form of substantially rigid threads or ridges 778, similar to ridges 178 of the securing device 200 described above, are provided for engaging the threaded shaft 108 of the bone fastener 104 in the third guiding bore 768 along the axis B as shown in FIGS. 23 and 32, in non-reconstructive procedures or when reconstructive fasteners are not used.

Figure 33:
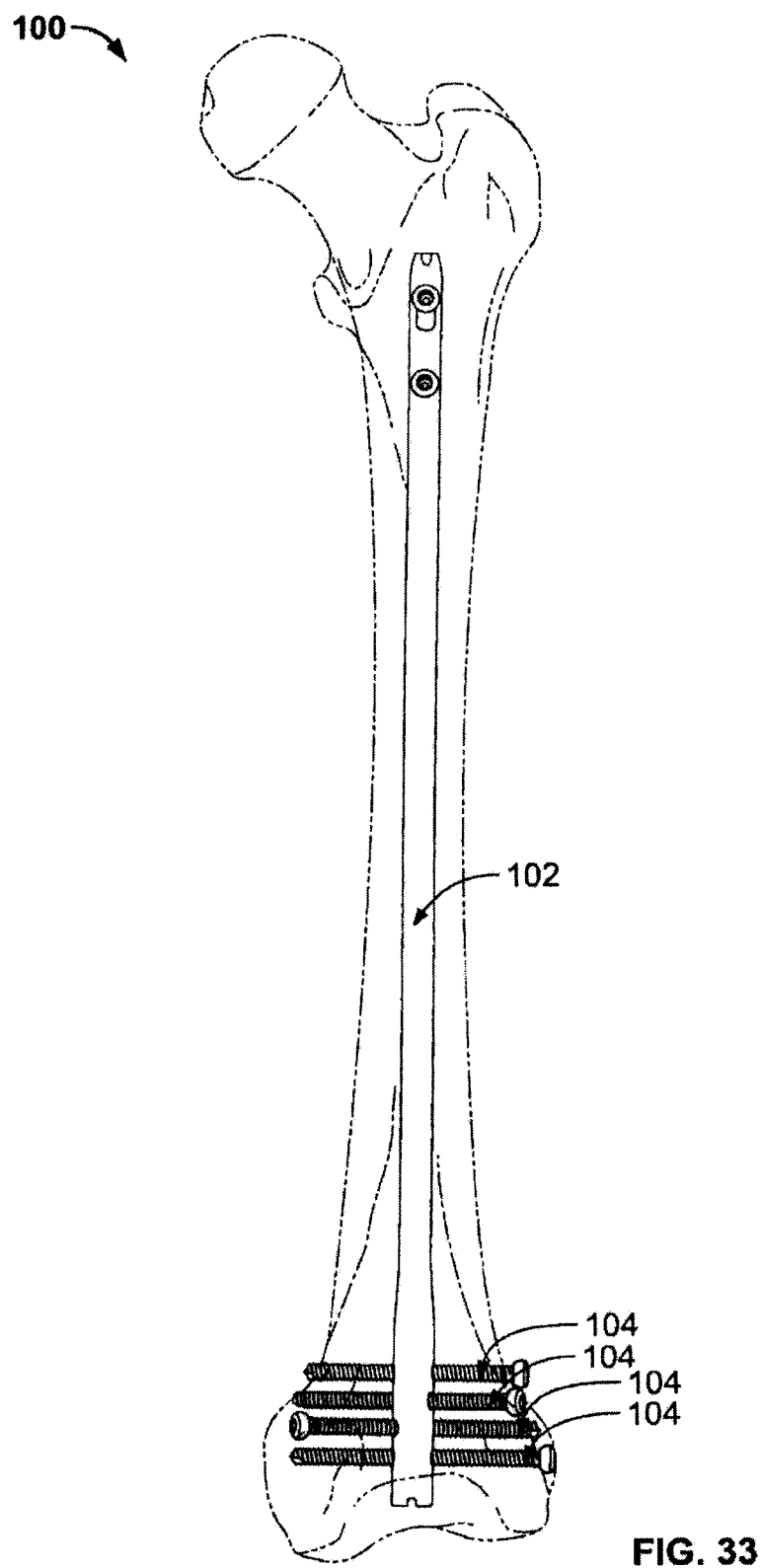
FIG. 33 is an environmental view of a fixation device according to the present teachings, illustrating a retrograde procedure with an intramedullary implant and interlocking fixation fasteners in the distal femur.
Figure 33A:
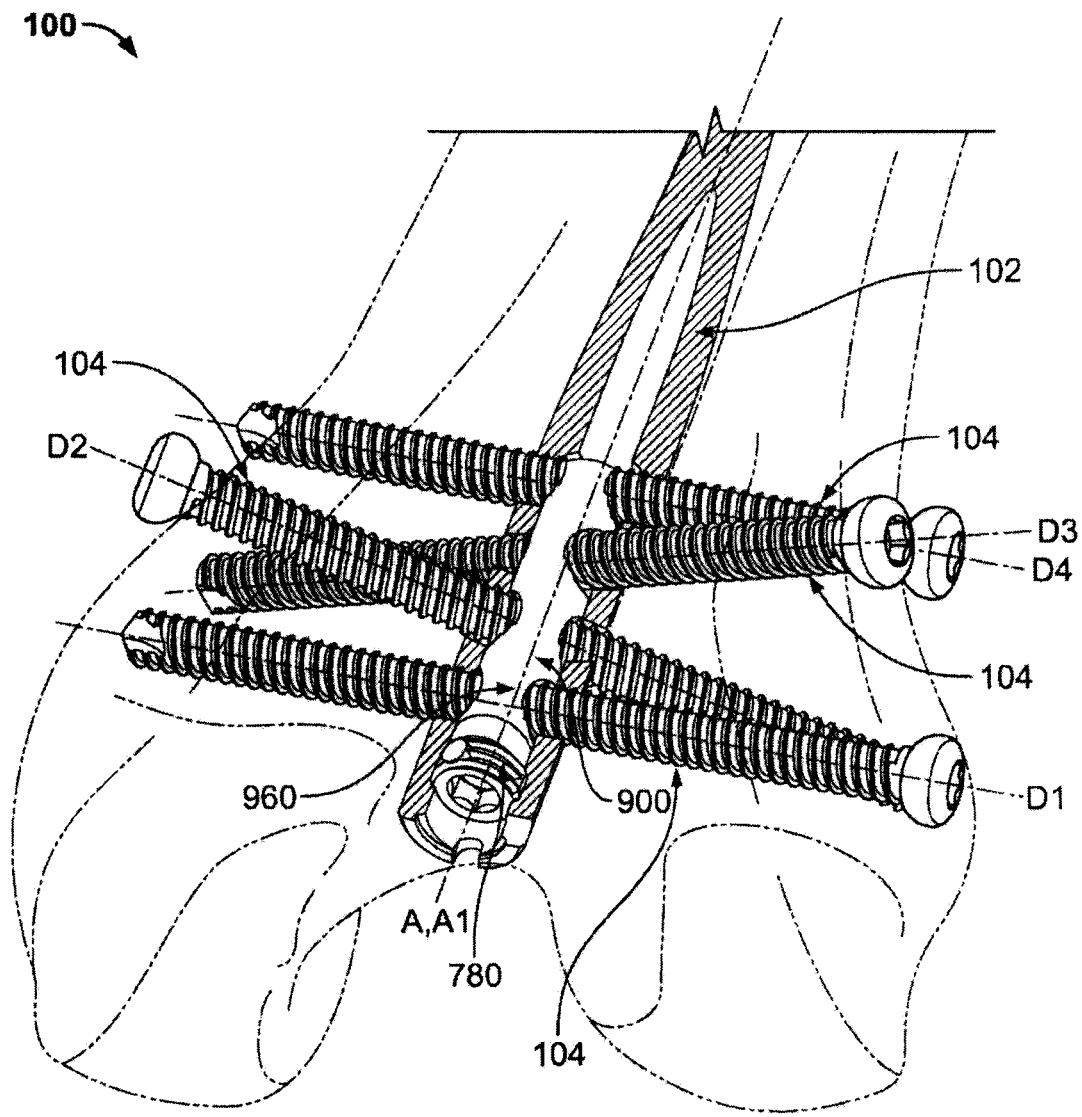
FIG. 33A is an enlarged detail of FIG. 33.
Figure 36:
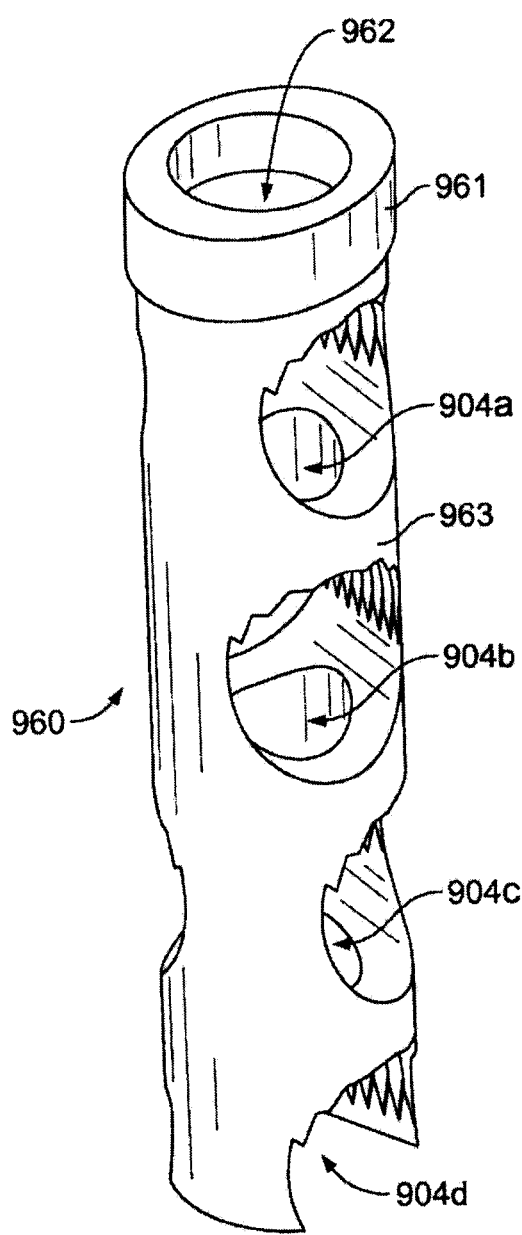
FIG. 36 is a perspective view of an insert of the securing device of FIG. 35.
Figure 37:
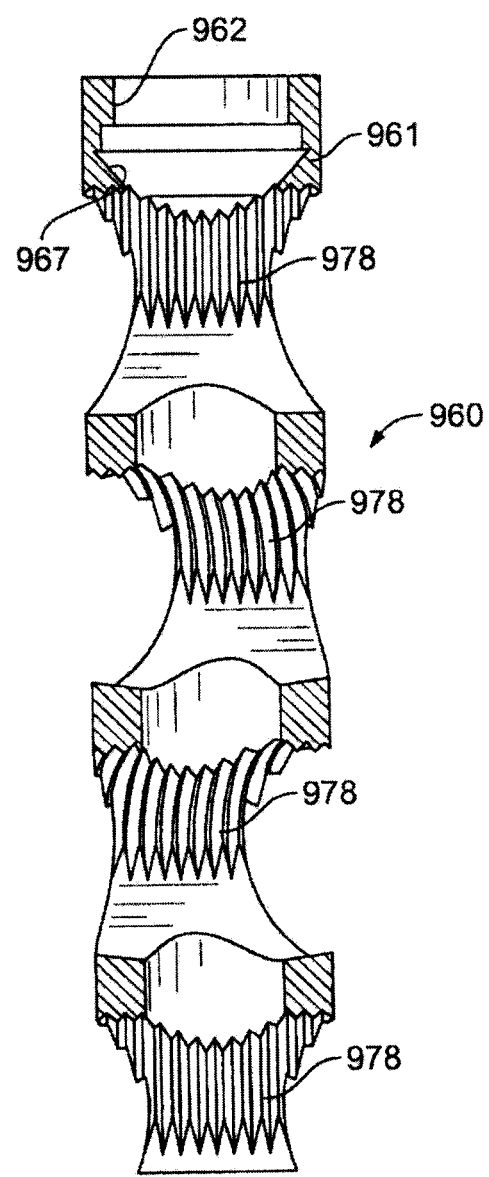
FIG. 37 is a sectional elevated view of the insert of FIG. 36.

Referring to FIGS. 33A-37, the movable insert 960 of the securing device 900 for the retrograde procedure can include first, second, third and fourth guiding bores 904a, 904b, 904c and 904d along corresponding axes D1, D2, D3 and D4 as shown in FIGS. 33A, and 34, for example. The axes D1 to D4 can be oriented at different three-dimensional orientations relative to the longitudinal axes A, A1 of IM implant 102 and the movable insert 960. Further, each bone fastener 104 can be oriented at a different angle relative to the other bone fasteners 104, as shown in FIG. 33A.

Figure 43:
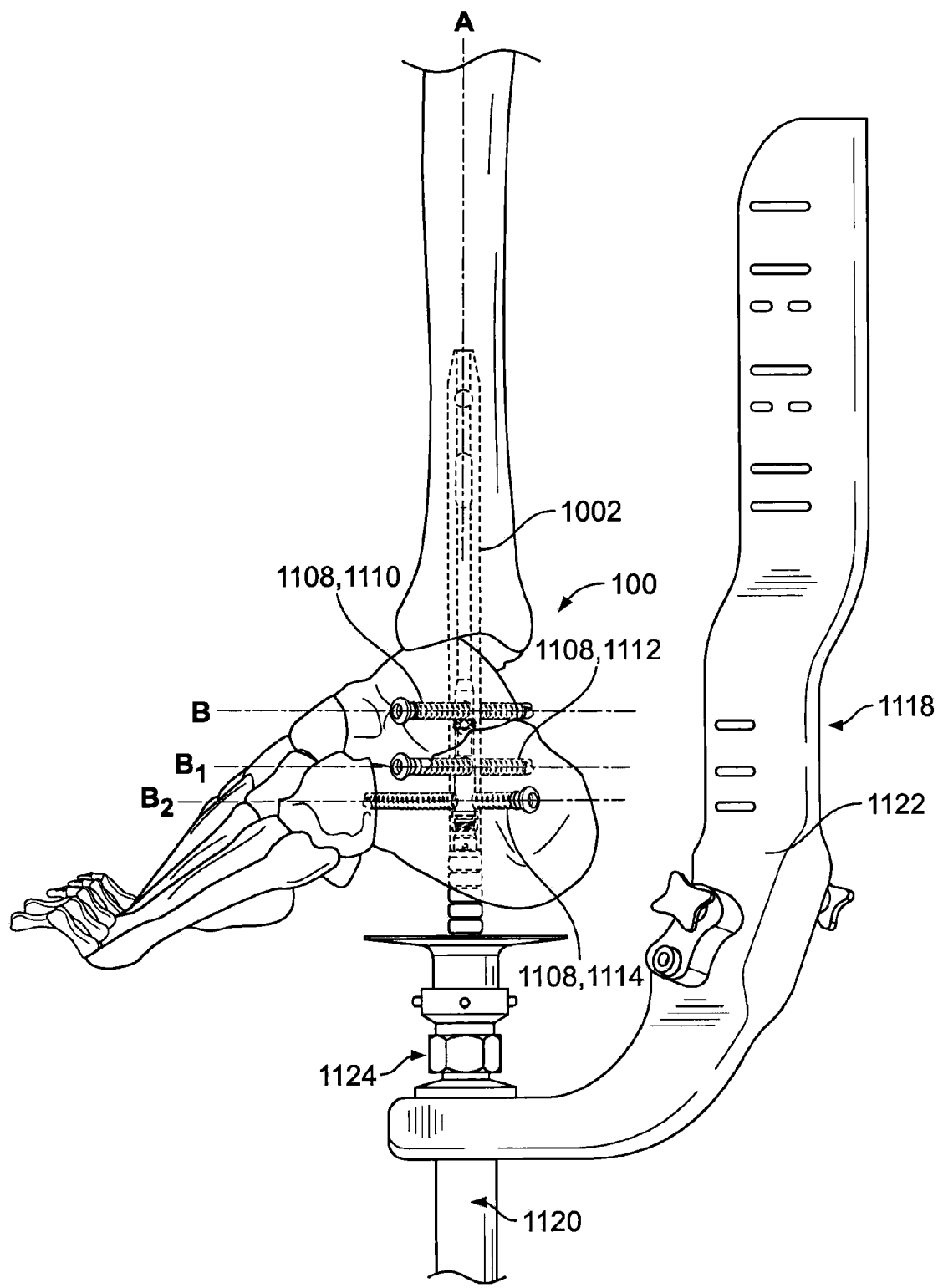
FIG. 43 is an environmental perspective view an intramedullary fixation device according to the present teachings, the fixation device shown implanted for ankle arthrodesis and coupled to a targeting instrument.

Referring to FIGS. 38 and 39, an exemplary fixation device 100 according to the present teachings is shown mounted on a targeting instrument 1118. The fixation device 100 can include an elongated intramedullary (IM) implant or nail 1002 having a longitudinal bore 1006 along a longitudinal axis A, a compression device 1024, and a locking device 1030. Both the compression device 1024 and the locking device 1030 can be pre-assembled inside the longitudinal bore 1006 of the IM implant 1002. The compression device 1024 and the locking device 1030 can operate independently of each other and can be used with various fixation fasteners 1108. The compression device 1024 can be used, for example, with a compression fixation fastener 1110 to provide compression of a fracture line and/or move bone segments toward one another. The locking device 1030 can engage one or more locking fixation fasteners 1112, 1114 and lock them to the IM implant 1002, as shown in FIG. 43 in an exemplary ankle arthrodesis procedure. As illustrated, the fixation fasteners 1108 can be threaded.

Referring to FIGS. 38, 39 and 43, the targeting instrument 1118 can include a longitudinal shaft 1120, a curved targeting arm 1122 rotatably coupled to the shaft 1120, and an external compression nut 1124 mounted on the shaft 1120. The targeting instrument 1118 can include a nose or tip 1126 lockingly coupled to the IM implant 1002 using a connecting bolt or other connecting fastener 1128. Turning the compression nut 1124 by one turn can provide talo-calcaneal compression of an amount of about 1 mm, for example.

Figure 44:
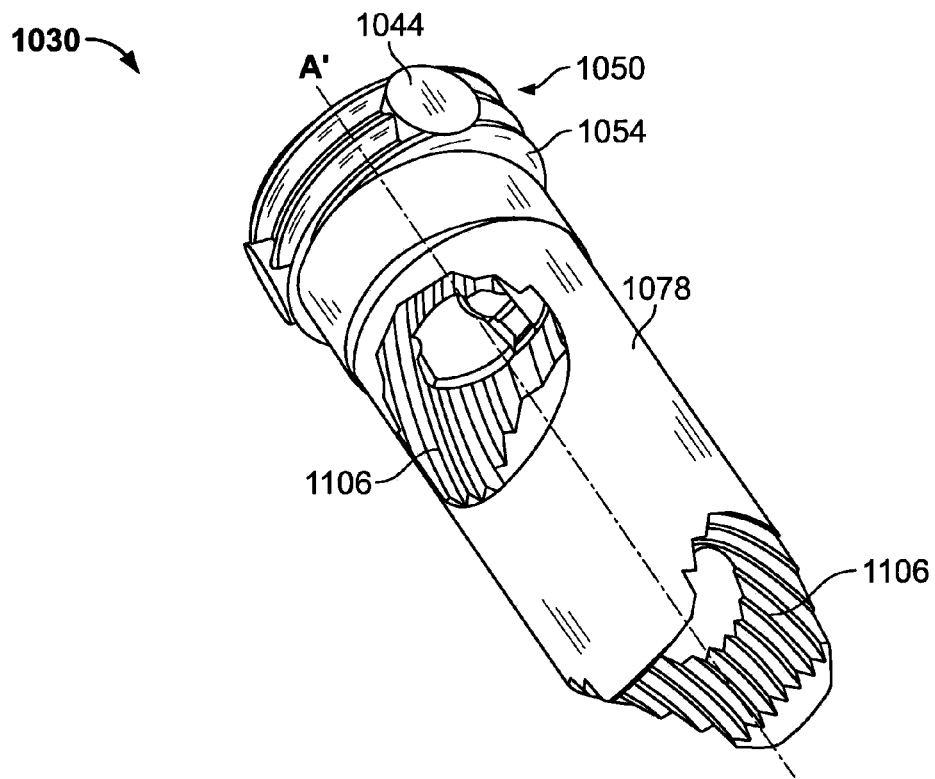
FIGS. 44 and 44A are perspective views of a locking device for an intramedullary fixation device according to the present teachings.
Figure 44A:
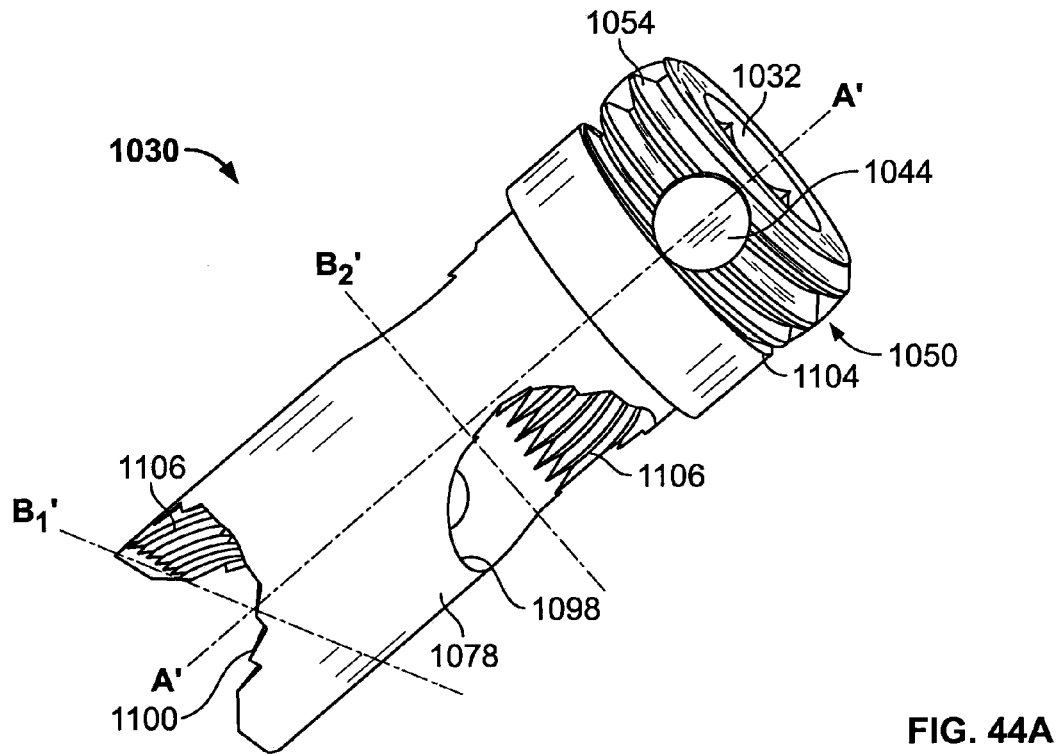
Figure 44B:
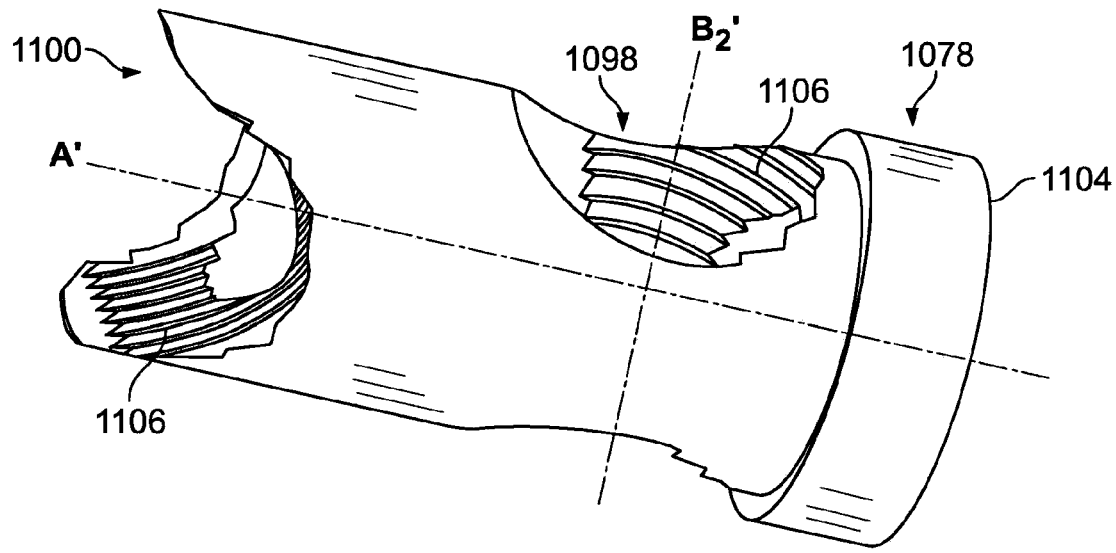
FIGS. 44B and 44C are perspective views of a first component of the locking device of FIG. 44.
Figure 44C:
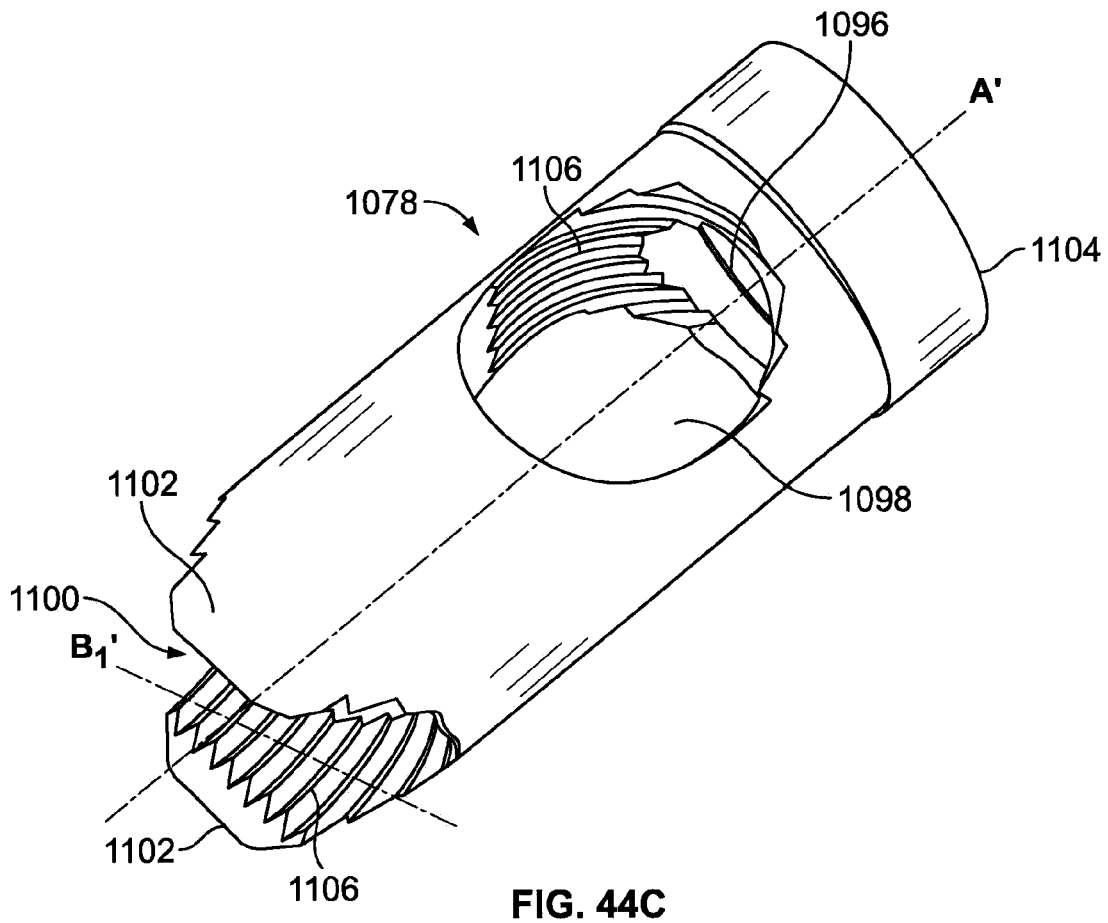
Figure 44D:
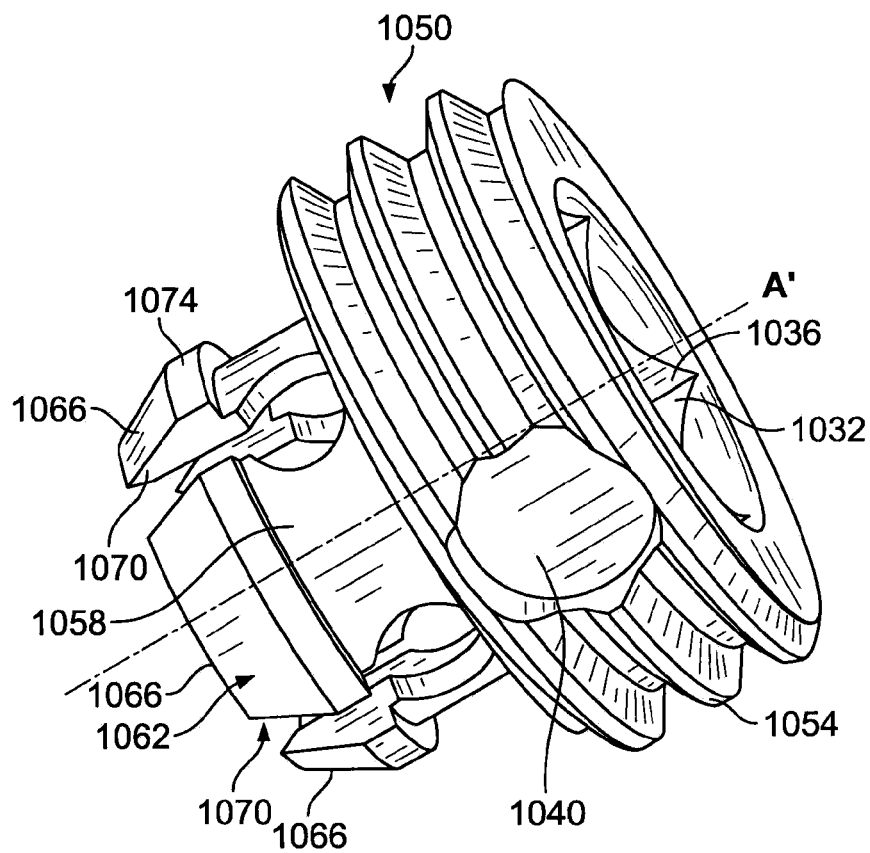
FIGS. 44D and 44E are perspective views of a second component of the locking device of FIG. 44.
Figure 44E:
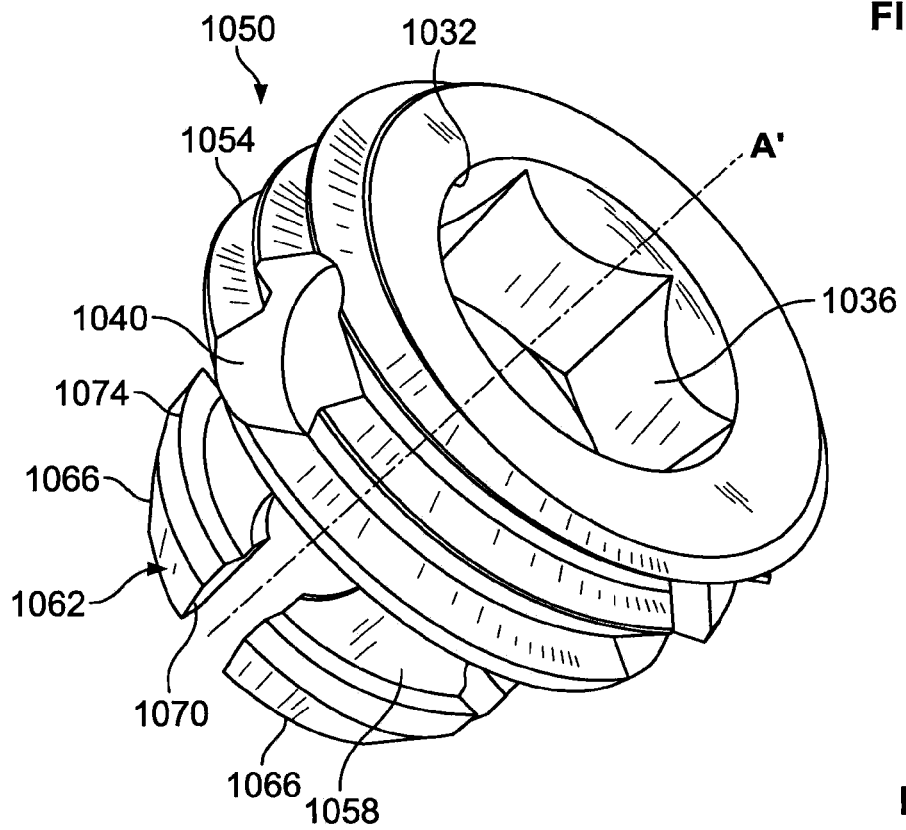
Figure 44F:
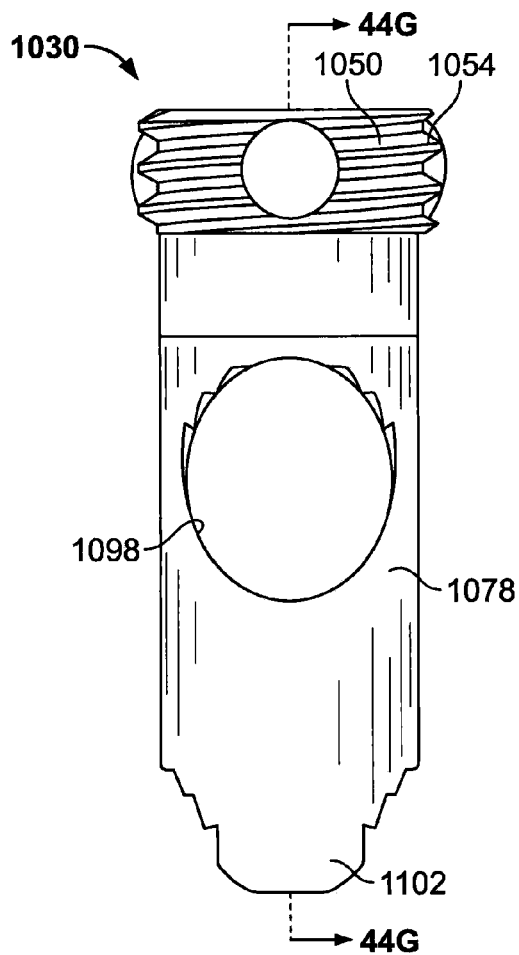
FIG. 44F is an elevated side view of the locking device of FIG. 44.
Figure 44G:
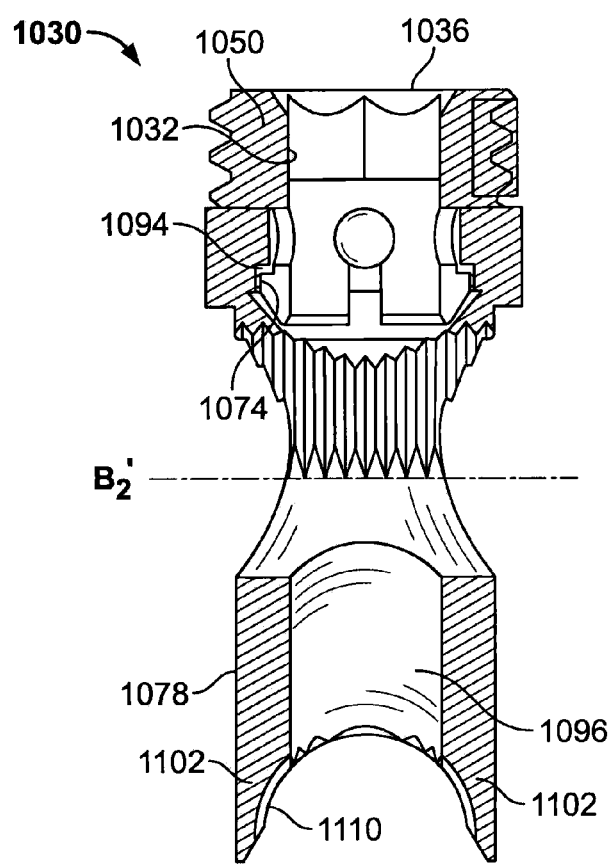
FIG. 44G is a sectional view of the longing device of FIG. 44F taken along line 44G-44G.
Figure 45:
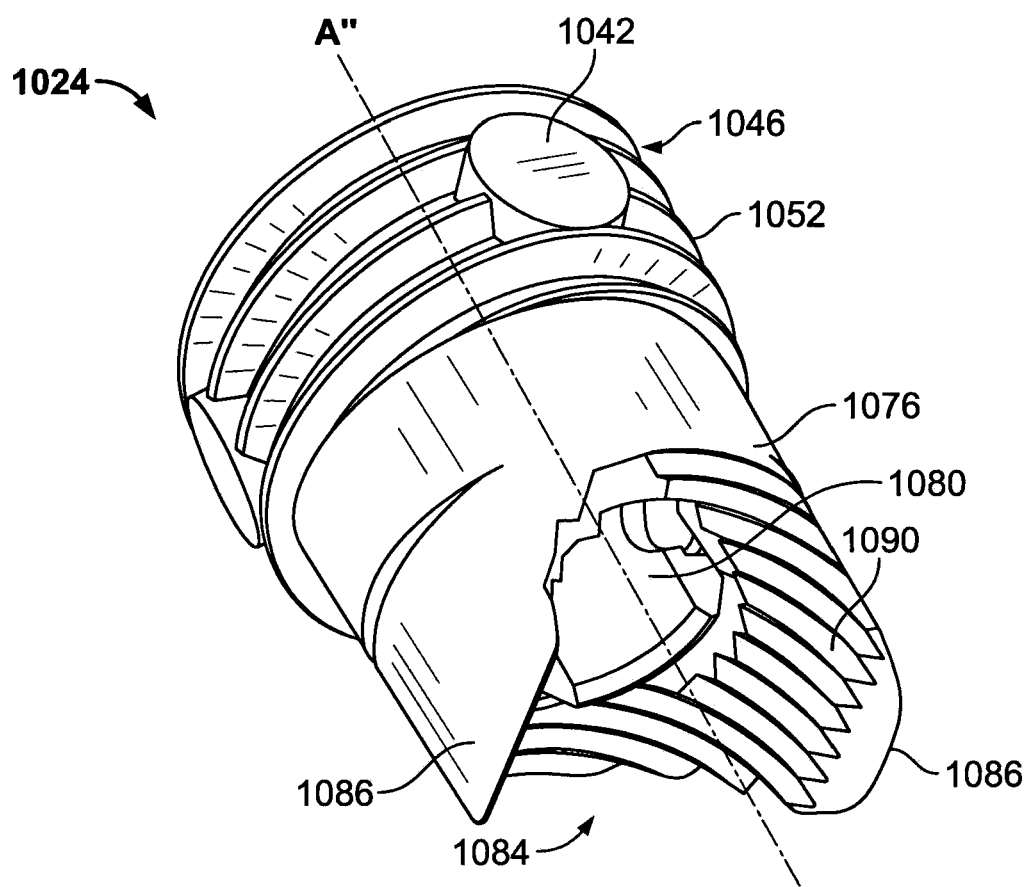
FIG. 45 is a perspective view of a compression device according to the present teachings.
Figure 45A:
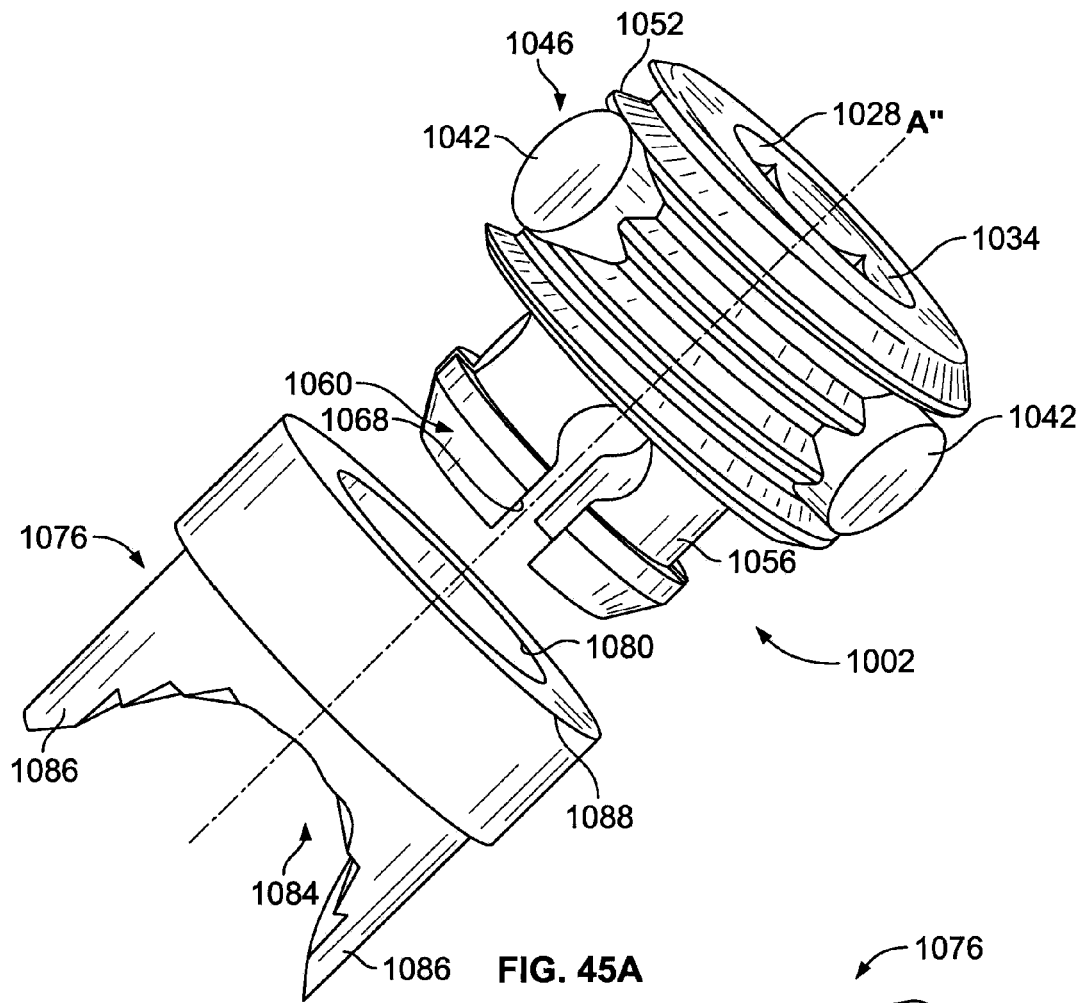
FIG. 45A is an exploded view of the compression device of FIG. 45.
Figure 45B:
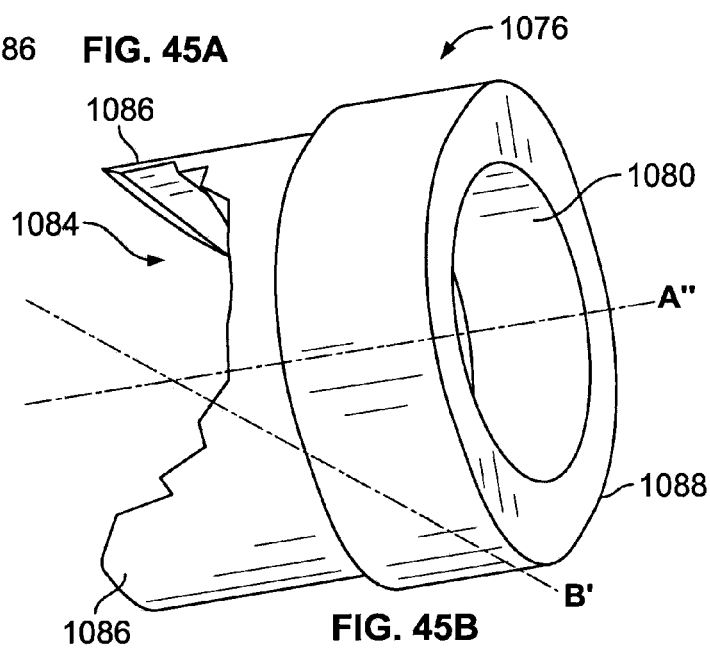
FIG. 45B is a perspective view of a first component of the compression device of FIG. 45.
Figure 45C:
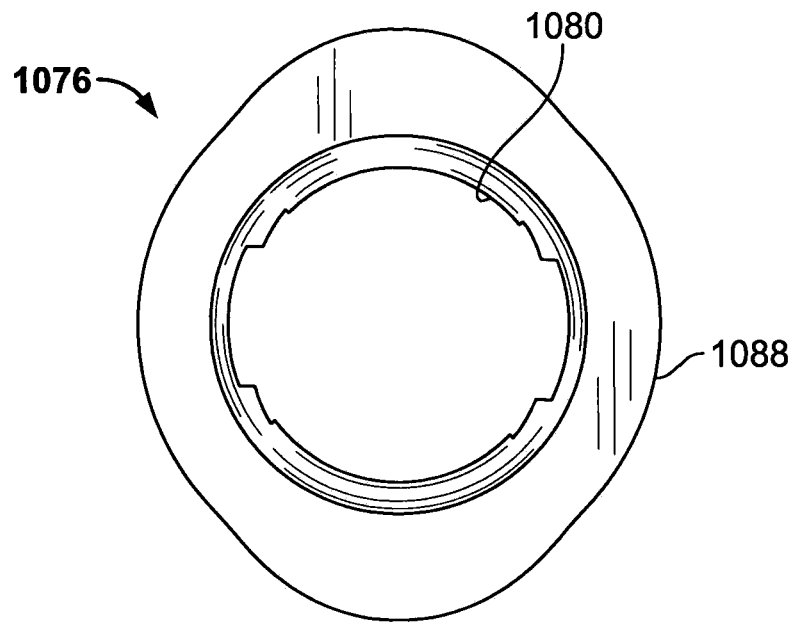
FIG. 45C is an end view of the first component of FIG. 45B.
Figure 45D:
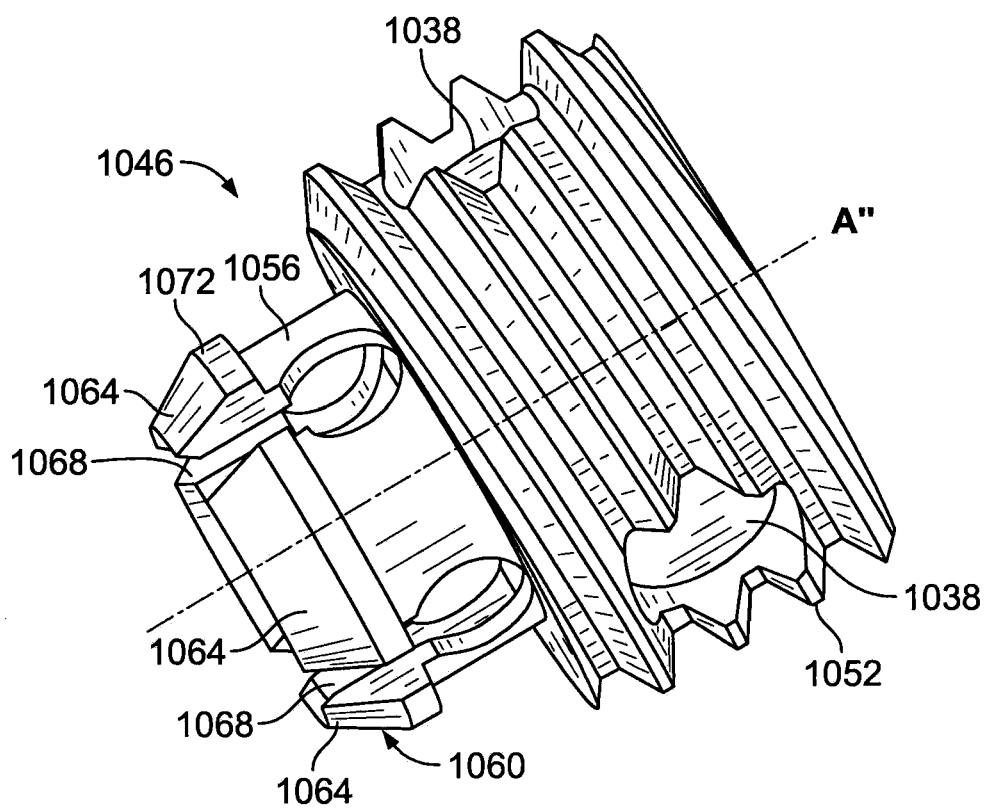
FIGS. 45D and 45E are perspective views of a second component of the compression device of FIG. 45.
Figure 45E:
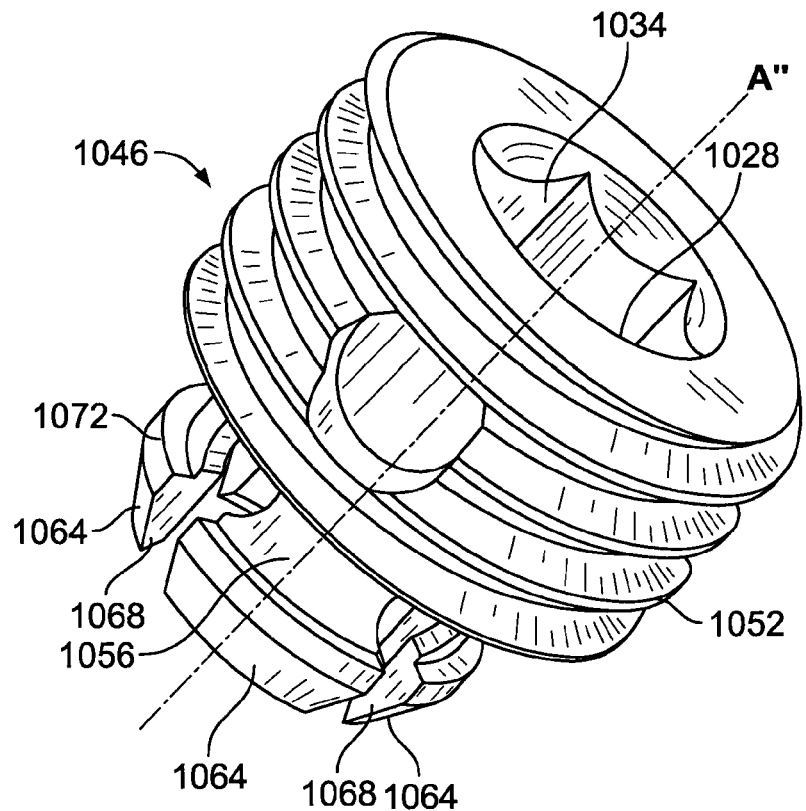
Figure 45F:
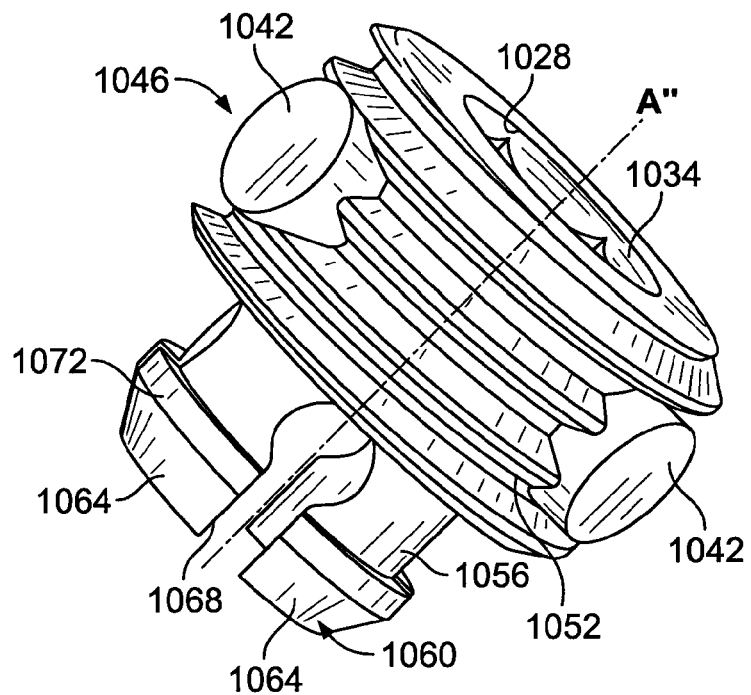
FIG. 45F is a perspective view of a second component of the compression device of FIG. 45.
Figure 45G:
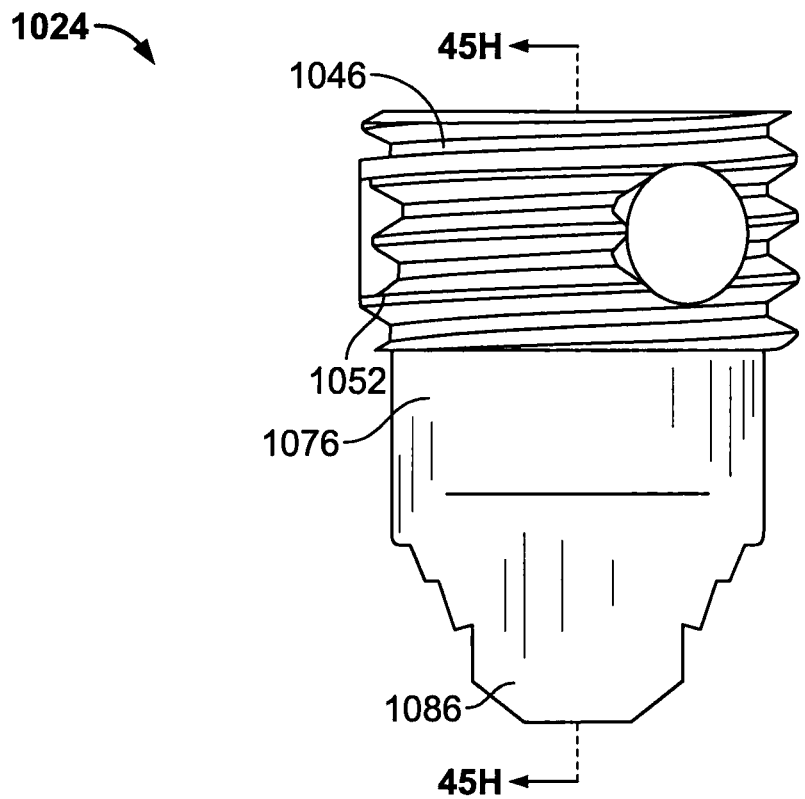
FIG. 45G is an elevated side view of the compression device of FIG. 45.
Figure 45H:
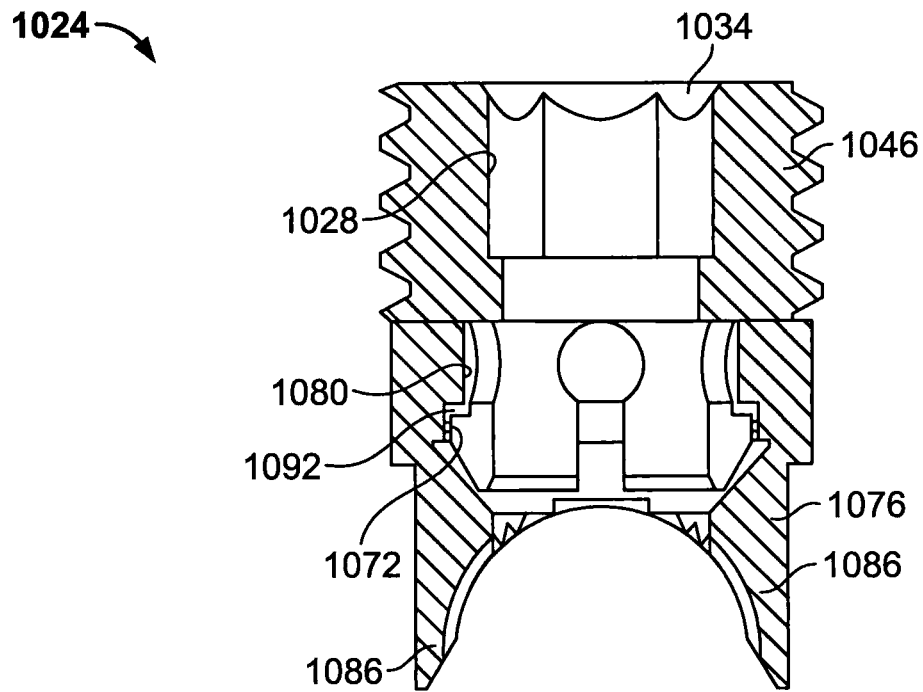
FIG. 45H is a sectional view of the compression device of FIG. 45G taken along line 45H-45H.

Referring to FIGS. 44-44G, the locking device 1030 can include first and second internally cannulated components 1050, 1078, which can be coupled to one another by a snap-fit arrangement or other type of connection. Similarly, and referring to FIGS. 45-45H, the compression device 1024 can include first and second internally cannulated components 1046, 1048, which can be coupled to one another by a snap-fit arrangement or other type of connection. Each of the first components 1046, 1050 can include a threaded portion with external threads 1052, 1054, respectively, for threadably engaging corresponding internally threaded portions 1010, 1012 of the longitudinal bore 1006 of the IM implant 1002, as shown in FIG. 39.

Referring to FIGS. 39, 43, 47A and 47B, the IM implant 1002 can have a distal portion 1004 and a proximal portion 1008. The distal portion 1004 generally extends over the length shown in FIG. 39, which corresponds to the Detail D of FIG. 38. The distal portion 1004 of the IM implant 1002 can define an elongated through-slot 1014, a first through-aperture 1016 and a second through-aperture 1018. The slot 1014 can be elongated in the direction of the longitudinal axis A, and can cross transversely the longitudinal bore 1006 of the IM implant 1002 along an axis B, which is substantially perpendicular to the longitudinal axis A. The first aperture 1016 can also cross transversely the longitudinal bore 1006 of the IM implant along an axis B1. The axes B and B1 can be substantially parallel or have different orientations depending on the application. The second aperture 1018 can also cross transversely the longitudinal bore 1006 of the IM implant 1002 along an axis B2 which can be substantially orthogonal to axes A and B1.

For an ankle arthrodesis procedure, the slot 1014 can be oriented and located for receiving a fixation fastener 1108 in a talar position (talar or compression fixation fastener 1110), as illustrated in FIG. 43 in reference to an exemplary ankle arthrodesis procedure. Similarly, the first aperture 1016 of the IM implant 1002 can be oriented and positioned for receiving a fixation fastener 1108 (calcaneal or locking fixation fastener 1112) along the lateral-medial direction corresponding to the axis B1 in the calcaneal position. The second aperture 1018 can be oriented and positioned for receiving a fixation fastener 1108 (calcaneal or locking fixation fastener 1114) along the anterior-posterior direction corresponding to the axis B2 in the calcaneal position. It will be appreciated that the proximal portion 1008 of the IM implant 1002 can also include various slots and openings for receiving other or additional fixation fasteners 1108. The fixation fasteners 1108 can include portion with threading 1116.

Referring to FIGS. 44-44C, and 45-45B, the second components 1076 and 1078 of the compression and locking devices 1024, 1030 include corresponding openings for accommodating various fixation fasteners 1108 for the talar and calcaneal positions, as discussed above.

Specifically, the second component 1078 of the locking device 1030 can include a longitudinal bore 1096 along a longitudinal axis A' and a through-aperture or bore 1098 transversely intersecting the longitudinal bore 1096 along an axis B2'. The second component 1078 of the locking device 1030 can also include an end opening 1100 extending along an axis B1' and defined between two opposing end extensions 1102 of the second component 1078 of the locking device 1030. When the locking device 1030 is received within the longitudinal bore 1006 of the IM implant 1002, axes A', B1' and B2' align with the corresponding axes A, B1, and B2 of the IM implant 1002. Accordingly, the first and second apertures 1016, 1018 of the IM implant 1002 substantially align with the end opening 1100 and transverse aperture 1098 respectively of the locking device 1030.

To maintain proper orientation between the locking device 1030 and the IM implant 1002 for accommodating the fixation fasteners 1108, the second component 1078 can be keyed to the IM implant 1002. Referring to FIGS. 46A and 47A, the portion of the longitudinal bore 1006 of the IM implant 1002 that receives the second component 1078 of the locking device 1030, along section 47A-47A of FIG. 46A, for example, can be shaped to have an inner wall having a closed periphery 1020 in the form of a non-circular, elongated curve, such as an ellipse or oval or other elongated shape, as shown in FIG. 47A. The second component 1078 of the locking device 1030 can have an outer periphery 1104 of a shape substantially matching the shape of the periphery 1020 of the corresponding portion of the longitudinal bore 1006 of the IM implant 1002, such that the locking device 1030 can be received into the longitudinal bore 1006 of the IM implant 1002 in a keyed manner and maintain an orientation that aligns the corresponding openings of the locking device 1030 and the IM implant 1002, as discussed above. Further, inner surface portions of the end opening 1100 and transverse aperture 1098 of the second components 1078 of the locking device 1030 can include threads or ridges or other similar formations 1106 for engaging and meshing with the threading 1116 of the corresponding fixation fasteners 1108.

Referring to FIGS. 45, 45B, 45C, 46B and 47B, the second component 1076 of the compression device 1024 can include a longitudinal bore 1080 along a longitudinal axis A", and an end opening 1084 extending about an axis B' and defined between two opposing end extensions 1086 of the second component 1076 of the compression device 1024. When the compression device 1024 is received within the longitudinal bore 1006 of the IM implant 1002, axes A" and B' align with the corresponding axes A and B of the IM implant 1002. Accordingly, the slot 1014 of the IM implant 1002 substantially aligns with the end opening 1084 of the compression device 1024. Further, an inner surface portion of the end opening 1084 can include threads or ridges or other similar formations 1090 for engaging and meshing with the threading 1116 of the corresponding fixation fasteners 1108.

To maintain proper orientation between the compression device 1024 and the IM implant 1002 for accommodating a corresponding fixation fastener 1110 through the slot 1014, the second component 1076 can be keyed to the IM implant 1002. Referring to FIGS. 46B and 47B, the portion of the longitudinal bore 1006 of the IM implant 1002 that receives the second component 1076 of the compression device 1024, along section 47B-47B of FIG. 46B, for example, can be shaped to have an inner wall having a closed periphery 1022 in the form of a non-circular curve, as shown in FIG. 47A. The second component 1076 of the compression device 1024 can have an outer periphery 1088 of a shape substantially matching the shape of the periphery 1022 of a corresponding portion of the longitudinal bore 1006 of the IM implant 1002, such that the compression device 1024 can be received into the longitudinal bore 1006 of the IM implant 1002 in a keyed manner and maintain an orientation that aligns the end opening 1084 of the compression device 1024 and the slot 1014 of the IM implant 1002, as discussed above.

The periphery 1022 that receives the second component 1076 of the compression device 1024 can be sized and shaped to fit into the periphery 1020 that receives the second component 1078 of the locking device 1030, such that the second component 1076 of the compression device 1024 can pass through the periphery 1020 of the portion of the longitudinal bore 1006 of the IM implant 1002 that will hold the second component 1078 of the locking device 1030.

Referring to FIGS. 44D, 44E, 45D and 45E, the first components 1050, 1046 of the locking and compression devices 1030, 1024 can include generally similar features, and are also described in detail in co-pending U.S. patent application Ser. No. 11/627,575 filed on Jan. 26, 2007, the disclosure of which is incorporated by reference herein. It will be appreciated, however, that the size and shape of these components or portions thereof can be different. The first components 1046, 1050 allow the surgeon to engage/disengage the corresponding compression and locking devices 1024, 1030 in situ within the IM implant 1002, and with the IM implant 1002 implanted, because the first components 1046, 1050 can be threadably engaged with the inner threaded portions 1010, 1012 of the IM implant 1002, as shown in FIG. 39.

Each of the first components 1046, 1050, can include a longitudinal bore 1028, 1032 along corresponding longitudinal axes A" and A', an unthreaded cylindrical portion 1056, 1058, and a distal flexible or resilient portion 1060, 1062, respectively. Each resilient portion 1060, 1062 can be defined by a plurality of legs 1064, 1066 extending from the unthreaded portion 1056, 1058 and separated by slots 1068, 1070, respectively. Each resilient portion 1060, 1062 can also define a step or flange 1072, 1074 that can be retained into a groove 1092, 1094 of the corresponding second component 1076, 1078, for example, when the resilient portion 1060, 1062 is snap-fitted into the longitudinal bore 1080, 1082 of the corresponding second component 1076, 1078, as shown in FIGS. 45G-45H, and 44F-44G, respectively.

Figures 40, 41:
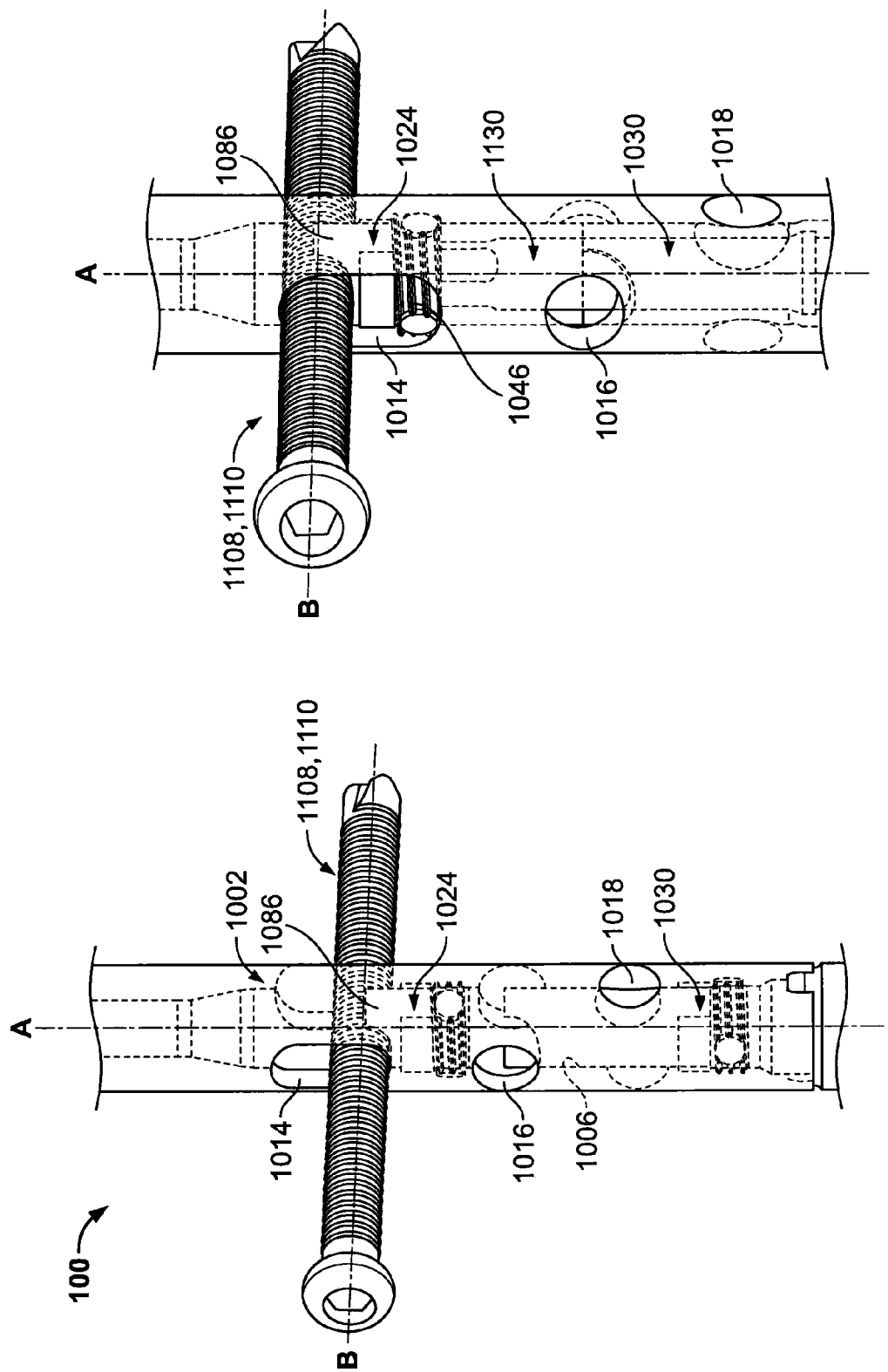
FIG. 40 is a perspective view of a detail of an intramedullary fixation device according to the present teachings, the fixation device shown with a compression device in a disengaged position relative to a fixation fastener.
FIG. 41 is a perspective view of a detail of the fixation device of FIG. 40, the fixation device shown with the compression device in an engaged position relative to the fixation fastener.

Each first component 1046, 1050 of the respective compression and locking devices 1024, 1030 can also include a driver engagement formation 1034, 1036 in a proximal portion of the corresponding longitudinal bore 1028, 1032 for engaging a corresponding compression or locking driver 1130. A compression driver 1130 for engaging the compressing device 1024 is illustrated in FIG. 41. The compression driver 1130 can be, for example, a hex wrench specifically sized to pass through the locking device 1030 to reach the compression device 1024. In one aspect, the driver 1130 can be flexible.

Each of the first components 1046, 1050 can also include holes or other openings 1038, 1040 that interrupt the external threads 1052, 1054. The openings 1038, 1040 can be plugged with thread locks 1042, 1044 for preventing further engaging or disengaging movement between the first components 1046, 1050 and the IM implant 1002, thereby securing the position of the corresponding second components 1076, 1078 relative to the IM implant 1002 and the fixation fasteners 1108. The thread locks 1042, 1044 can be made of polyethylene, for example. In one aspect, the first component 1046, 1050 can be made of polyethylene. See, for example, FIG. 45F.

An exemplary procedure in relation to ankle arthrodesis is illustrated in FIGS. 39-43. FIG. 39 shows the exemplary fixation device 100 with the locking device 1030 and the compression device 1024 pre-assembled into the longitudinal bore 1006 of the IM implant 1002. Referring to FIG. 40, a talar fixation fastener 1110 can be inserted through the longitudinal slot 1014 of the IM implant 1002 along the axis B. Referring to FIG. 41, a compression driver 1130, sized or adapted for the compression device 1024, can be inserted through the IM implant 1002 and through the locking device 1030 and engage the driver engagement formation 1034 of the first component 1046 of the compression device 1024. Rotating the driver 1130 can move the talar fixation fastener 1110 along the slot 1014 from a proximal end to a distal end of the slot 1014 in the direction of axis A until the talar fixation fastener 1110 is held in compression between the end extensions 1086 of the compression device 1024. An amount of internal apposition or compression of about 7 mm can be for example, achieved.

Figure 42:
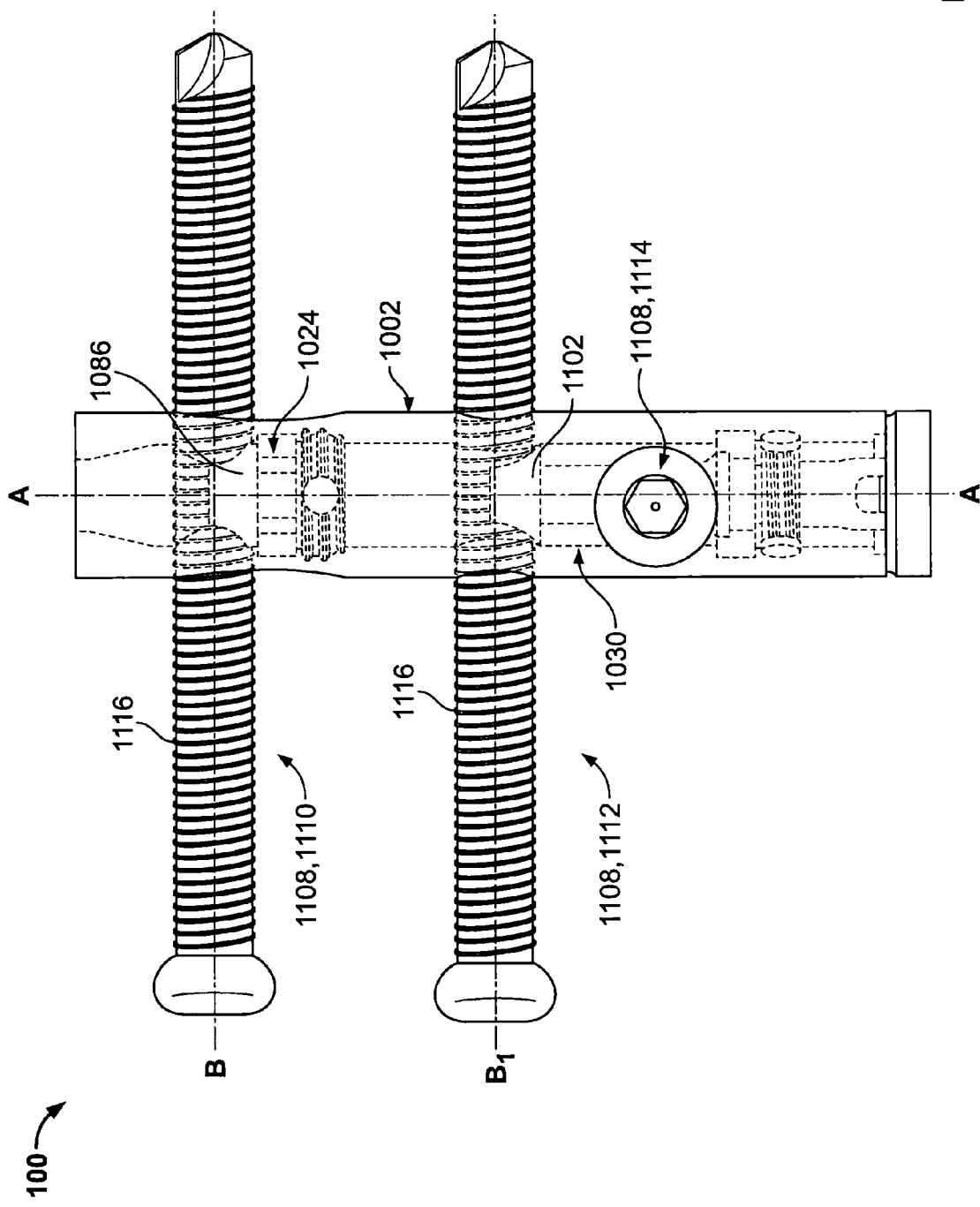
FIG. 42 is a perspective view of a detail of an intramedullary fixation device according to the present teachings, the fixation device shown with a compression device in a engaged position relative to a first fixation fastener, and with a locking device engaging a second fixation fastener.

Referring to FIG. 42, after tibio-talar compression is achieved as described above, the calcaneal fixation fasteners 1112, 1114 can be inserted through the first and second apertures 1016, 1018 of the IM implant 1002 and the corresponding apertures 1100, 1098 of the locking device 1030, respectively. A driver adapted or sized for the locking device 1030 can be used to engage the driver engagement formation 1036 of the first component 1050 of the locking device 1030 to lockingly couple the calcaneal fixation fasteners 1112, 1114 in the IM implant 1002. Additionally, talo-calcaneal compression can still be performed using the externally mounted compression nut 1124, as discussed above.

The present teachings provide a versatile intramedullary fixation device that can be used for fracture reduction and/or arthrodesis applications. It will be appreciated that the use of two independent of each other compression and locking devices 1024, 1030, each of which is preassembled in the longitudinal bore 1006 of the IM implant 1002, affords the surgeon the ability to perform in-board or in situ compression independently from the locking cortical fixation screws or other fasteners to the IM implant 1002.

As it will be appreciated from the above description and drawings, the present teachings provide a securing device for intramedullary implant fixation that can be used telescopically to lock the intramedullary implant with more than one bone fasteners in interlocking or reconstructive procedures for the femur and tibia. Further, active compression of a fracture site can be obtained with the same securing device. Although a few representative applications have been described in detail, it will be understood that the present teachings can be applied to other intramedullary fixation procedures and that features and elements of the fixation device described in connection with one embodiment or procedure can be selectively combined with and/or replace features described in connection with another embodiment or procedure.

Referring to FIGS. 48-51, an exemplary elongated intramedullary (IM) implant 2000 is shown. In the following, the same reference numerals will be used to denote the same or similar components as those in FIGS. 7-9B, and only the differences will be discussed in great detail herein. The IM implant 2000 can include a variable angle positioning member or collet 2002. The collet 2002 can cooperate with a fixation device 2004 to enable bone fasteners 104 inserted through the fixation device 2004 to be positioned at a variable angle relative to the IM implant 2000.

Figure 48:
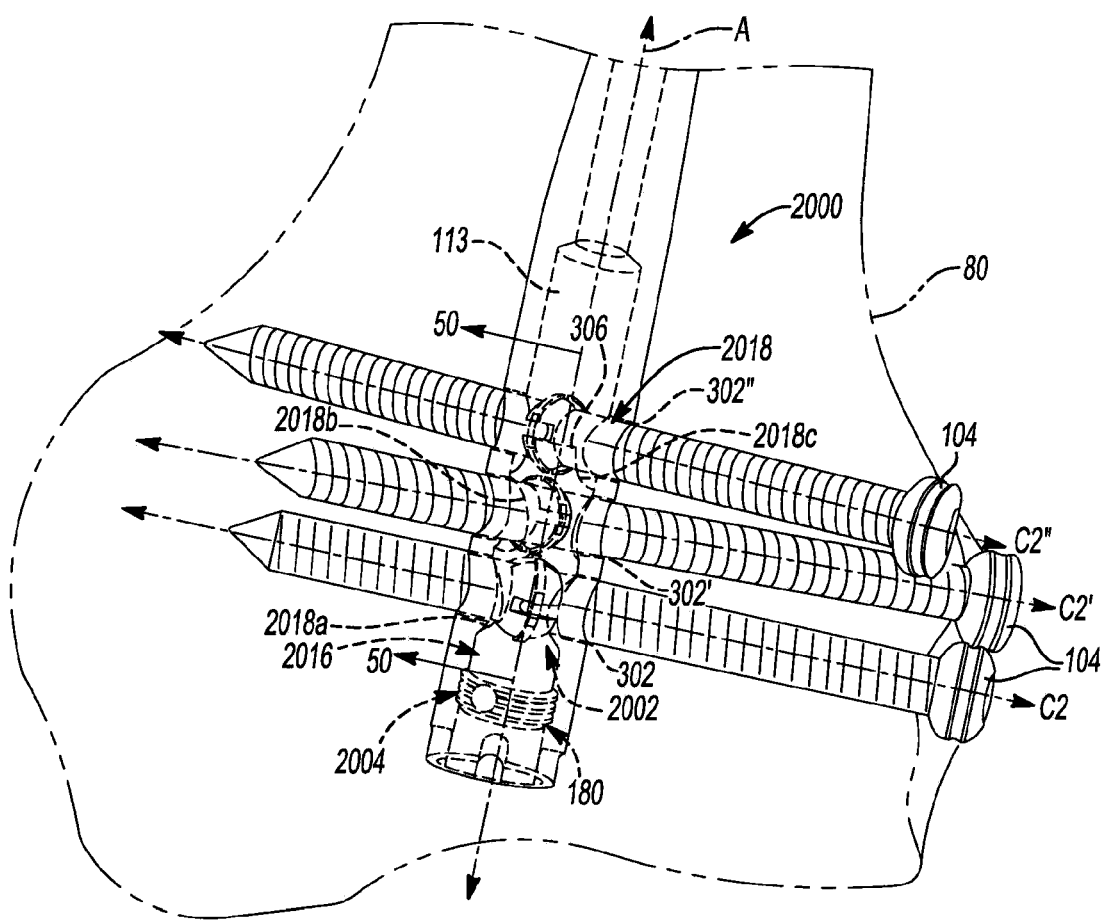
FIG. 48 is an environmental view of an exemplary intramedullary implant including a fixation device having a variable angle positioning member according to the present teachings for use in a retrograde femoral procedure.

In this regard, with reference to FIG. 48, the IM implant 2000 can include the shaft 110, which can have a proximal portion 2006. The IM implant 2000 can be positioned within an intramedullary canal of a long bone, such as the femur 80. The IM implant 2000 can be formed of a suitable biocompatible material, such as a biocompatible metal or metal alloy. The proximal portion 2006 of the IM implant 2000 can include the longitudinal bore 113, which can define the longitudinal axis A. The longitudinal bore 113 can receive the fixation device 2004. The proximal inner surface 111 of the proximal longitudinal bore 113 can be of elliptical or other non-circular shape, having different major and minor diameters such that the cross-section has an elongated shape.

The proximal portion 2006 of the IM implant 2000 can also include at least one fastener bore 302. The at least one fastener bore 302 can extend along an axis generally transverse to the longitudinal axis A of the IM implant 2000. In one example, the IM implant 2000 can include the first fastener bore 302, the second fastener bore 302' and the third fastener bore 302". The first fastener bore 302, the second fastener bore 302' and the third fastener bore 302" can be circumferentially offset relative to the longitudinal axis A, or can be aligned along the longitudinal axis A.

The fixation device 2004 can be received within the longitudinal bore 113 of the IM implant 2000. As the fixation device 2004 can be similar to the fixation device 100 described with reference to FIGS. 7-9B, only the differences between the fixation device 100 and the fixation device 2004 will be discussed in great detail herein, and the same reference numerals will be used to denote the same or similar components. The fixation device 2004 can include a movable member 2016 and the locking member 180. The movable member 2016 can include at least one guiding bore 2018. In this example, with reference to FIG. 49, the movable member 2016 can include a first guiding bore 2018a, a second guiding bore 2018b and a third guiding bore 2018c. The first guiding bore 2018a, second guiding bore 2018b and third guiding bore 2018c can be orientated along the first, second and third axes C2, C2', C2". The first guiding bore 2018a and the second guiding bore 2018b can be formed with closed perimeters. The third guiding bore 2018c can have an open perimeter that defines a pair of opposing legs 2019.

One or more of the first guiding bore 2018a, second guiding bore 2018b and third guiding bore 2018c can be aligned or circumferentially offset relative to one another or relative to the longitudinal axis A, and can be parallel or non-parallel to the longitudinal axis A so that the first guiding bore 2018a, second guiding bore 2018b and third guiding bore 2018c can be substantially coaxially aligned with the first fastener bore 302, the second fastener bore 302' and the third fastener bore 302". In addition, one or more of the first guiding bore 2018a, second guiding bore 2018b and third guiding bore 2018c can include a collet retaining feature or collet groove 2020. The collet groove 2020 can cooperate with the collet 2002 to retain the collet 2002 within the fixation device 2004 at a desired orientation. In one example, the collet groove 2020 can be formed about at least a portion of the perimeter or circumference of the first guiding bore 2018a, second guiding bore 2018b and third guiding bore 2018c. Alternatively, the collet groove 2020 can be formed substantially about the circumference of the first guiding bore 2018a and second guiding bore 2018b.

Generally, the collet groove 2020 can be formed about enough of the circumference of the first guiding bore 2018a, second guiding bore 2018b and third guiding bore 2018c to ensure the collet 2002 is retained within the fixation device 2004 at an orientation that enables the bone fastener 104 to pass through the fixation device 2004 (FIG. 48). It should be noted that the use of a collet groove 2020 is merely exemplary as any suitable technique could be employed to ensure the proper orientation of the collet 2002 within the IM implant 2000, such as a slot, a notch, a keyed portion, a set screw, etc. In one example, the collet groove 2020 can be formed along opposing sides of the first guiding bore 2018a, second guiding bore 2018b and third guiding bore 2018c to enable the collet 2002 to be retained within, but also movable relative to the first guiding bore 2018a, second guiding bore 2018b and third guiding bore 2018c. Although the collet groove 2020 is described and illustrated herein as being formed on opposing sides of the first guiding bore 2018a, second guiding bore 2018b and third guiding bore 2018c, the collet groove 2020 could be formed on only one side of the first guiding bore 2018a, second guiding bore 2018b and third guiding bore 2018c, if desired. The collet groove 2020 can have a slight concavity, if desired, to assist in retaining the collet 2002 within the collet groove 2020. The collet groove 2020 can be configured to enable the collet 2002 to move relative to the respective one of the first guiding bore 2018a, second guiding bore 2018b and third guiding bore 2018c.

In this regard, the collet 2002 can pivot or angulate relative to the respective one of the first guiding bore 2018a, second guiding bore 2018b and third guiding bore 2018c. In addition, the collet groove 2020 can receive the collet 2002 so that the collet 2002 can also rotate within the first guiding bore 2018a, second guiding bore 2018b and third guiding bore 2018c. The movement of the collet 2002 within the first guiding bore 2018a, second guiding bore 2018b and third guiding bore 2018c can enable flexibility in the placement of the bone fastener 104 through the IM implant 2000.

With reference to FIG. 50, the collet 2002 can have a central axis EE. The collet 2002 can move relative to the axis C2, C2', C2" of the respective one of the first guiding bore 2018a, second guiding bore 2018b and third guiding bore 2018c. In one example, the collet 2002 can move so that the central axis EE is offset from the respective axis C2, C2', C2". The central axis EE can be offset from the respective axis C2, C2', C2" at an angle of about 5 to about 20 degrees in any direction, which can result in a cone of movement M for the collet 2002 within the respective first guiding bore 2018a, second guiding bore 2018b and third guiding bore 2018c. The cone of movement M of the collet 2002 relative to the axis C2, C2', C2" can allow the bone fastener 104 to be positioned into the anatomy free-hand or without the use of a targeting instrument, if desired. Generally, the collet 2002 can be positioned within the fixation device 2004 so that the collet 2002 does not translate within the first guiding bore 2018a, second guiding bore 2018b and third guiding bore 2018c.

Generally, the collet 2002 can be received within each of the first guiding bore 2018a, second guiding bore 2018b and third guiding bore 2018c. The collet 2002 can enable the bone fastener 104 to be positioned within the anatomy at a variable angle relative to the respective axis C2, C2', C2". The collet 2002 can be composed of any suitable biocompatible material, such as a biocompatible metal, metal alloy or polymer. For example, the collet 2002 could be composed of polyetheretherketone (PEEK) or titanium alloy.

With reference to FIG. 51, the collet 2002 can be generally annular, and can include at least one slot 2022, at least one rib 2024 and a central bore 2025. The central bore 2025 can receive the bone fastener 104 therethrough. The at least one slot 2022 can enable the collet 2002 to be compressed to couple the bone fastener 104 to the IM implant 2000, as will be discussed in greater detail herein. In one example, the collet 2002 can include four slots 2022a-d. In this example, two of the slots 2022a, 2022c can extend from a first end 2026 to be adjacent to a second end 2028 of the collet 2002. The slots 2022b, 2022d can extend from the second end 2028 to be adjacent the first end 2026. The slots 2022b, 2022c can be generally opposite each other about the perimeter or circumference of the collet 2002, and the slots 2022a, 2022d can be generally opposite each other about the perimeter or circumference of the collet 2002. The first end 2026 can be circumferentially open at the locations of the slots 2022a, 2022c and the second end 2028 can be circumferentially open at the locations of the slots 2022b, 2022d. It should be noted that this configuration of the slots 2022 is merely exemplary, as only one slot 2022 could be employed, or a slot 2022 could extend through the collet 2002 from the first end 2026 to the second end 2028, if desired. Generally, the slots 2022a-d can be substantially evenly spaced about the circumference of the collet 2002, however, the slots 2022a-d could be positioned at any desired location relative to each other about the collet 2002.

The at least one rib 2024 can be formed along the perimeter or circumference of the collet 2002 on an exterior surface 2030 of the collet 2002. In one example, the at least one rib 2024 can include four ribs 2024a-d. Each rib 2024a-d can be formed between a respective pair of slots 2022a, 2022b; 2022b, 2022c; 2022c, 2022d; 2022d, 2022a. The ribs 2024a-d can be formed to cooperate with the collet groove 2020 to movably couple the collet 2002 to the fixation device 2004. Generally, the ribs 2024a-d can couple the collet 2002 to the fixation device 2004 such that the collet 2002 can move, pivot or rotate within the respective one of the first guiding bore 2018a, second guiding bore 2018b and third guiding bore 2018c. It should be noted that the number of ribs 2024 is merely exemplary, as only one rib 2024 could be used, if desired. Further, the shape of the ribs 2024 is merely exemplary, as each rib 2024a-d could have a unique thickness or shape to control the motion of the collet 2002 within the respective one of the first guiding bore 2018a, second guiding bore 2018b and third guiding bore 2018c.

In order to employ the collet 2002 with the fixation device 2004, the movable member 2016 and locking member 180 can be assembled within the IM implant 2000. Then, the collet 2002 can be positioned within each of the first guiding bore 2018a, second guiding bore 2018b and third guiding bore 2018c so that the respective ones of the ribs 2024a-d are retained within the respective collet grooves 2020.

With the collets 2002 coupled to the fixation device 2004, the IM implant 2000 can be inserted into a prepared portion of the anatomy. In this example, the IM implant 2000 can be used in a retrograde interlocking femoral fixation procedure and can be inserted into the distal portion of the femur 80 in a retrograde direction. Once positioned within the intramedullary canal of the femur 80, bone fasteners 104 can be inserted through the anatomy into each of the first fastener bore 302, second fastener bore 302' and third fastener bore 302". The collet 2002 can enable the bone fasteners 104 to be inserted about 5 to about 20 degrees offset from the axis C2, C2', C2" of the first guiding bore 2018a, second guiding bore 2018b and third guiding bore 2018c, which can enable the bone fasteners 104 to be inserted without the use of a targeting instrument, if desired.

With the bone fasteners 104 inserted through the first guiding bore 2018a, second guiding bore 2018b and third guiding bore 2018c of the movable member 160, the locking member 180 can be rotated to advance the movable member 160 within the IM implant 2000, as discussed previously herein. The movement or advancement of the movable member 160 within the longitudinal bore 113 can apply a force to the first end 2026 of the collets 2002, which can deform the collets 2002. The deformation of the collets 2002 can couple or lock the bone fasteners 104 to the IM implant 2000.

Figure 52:
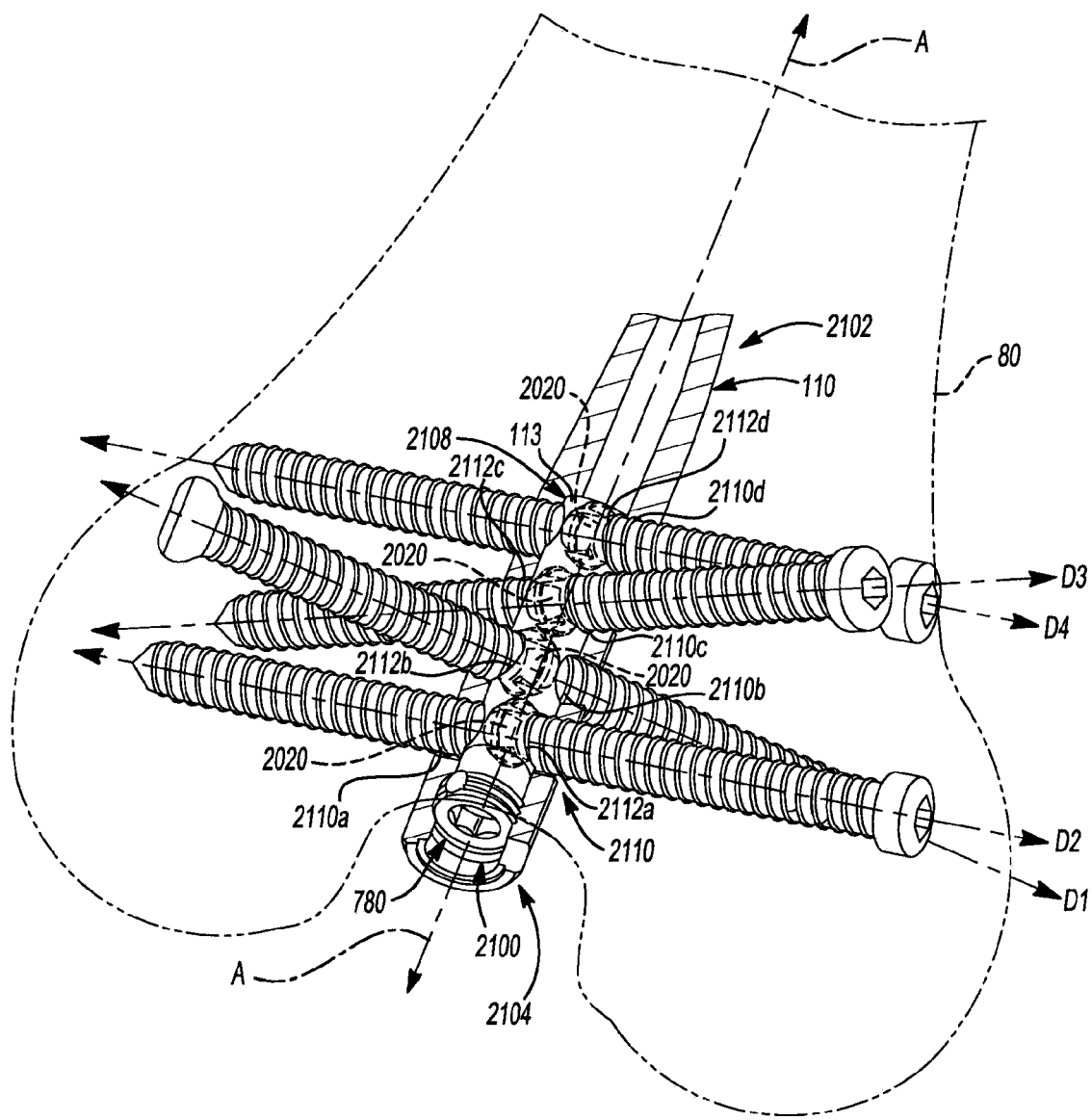
FIG. 52 is an environmental view of another exemplary intramedullary implant including a fixation device having the variable angle positioning member according to the present teachings.

In another example, with reference to FIG. 52, the collet 2002 can be employed with an exemplary fixation device 2100. The fixation device 2100 can be assembled within an exemplary IM implant 2102. As the fixation device 2100 and IM implant 2102 can be similar to the securing device 900 and IM implant 102 discussed with regard to FIGS. 33A-37, the same reference numerals will be used to denote the same or similar components and only the differences will be discussed in great detail herein. In this example, the collet 2002 can cooperate with the fixation device 2100 to enable bone fasteners 104 inserted through the fixation device 2100 to be positioned at a variable angle relative to the IM implant 2102.

The IM implant 2102 can include the shaft 110, which can have a proximal portion 2104. The IM implant 2102 can be positioned within an intramedullary canal of a long bone, such as the femur 80. The IM implant 2102 can be formed of a suitable biocompatible material, such as a biocompatible metal or metal alloy. The proximal portion 2104 of the IM implant 2102 can include the longitudinal bore 113, which can be defined about the longitudinal axis A. The longitudinal bore 113 can receive the fixation device 2100.

The proximal portion 2006 of the IM implant 2102 can also include at least one fastener bore 2110. The at least one fastener bore 2110 can extend along an axis generally transverse to the longitudinal axis A of the IM implant 2102. In one example, the IM implant 2102 can include the first fastener bore 2110a, the second fastener bore 2110b, the third fastener bore 2110c and a fourth fastener bore 2110d. The first fastener bore 2110a, second fastener bore 2110b, third fastener bore 2110c and fourth fastener bore 2110d can be circumferentially offset relative to the longitudinal axis A, or can be aligned along the longitudinal axis A.

The fixation device 2100 can be received within the longitudinal bore 113 of the IM implant 2102. The fixation device 2100 can include a movable member 2108 and the locking member 780. The movable member 2108 can include at least one guiding bore 2112. In this example, the movable member 2108 can include a first guiding bore 2112a, a second guiding bore 2112b, a third guiding bore 2112c and a fourth guiding bore 2112d. The first guiding bore 2112a, the second guiding bore 2112b, the third guiding bore 2112c and the fourth guiding bore 2112d can be orientated along the first, second, third and fourth axes D1, D2, D3, D4. The first guiding bore 2112a, the second guiding bore 2112b and the third guiding bore 2112c can be formed with closed perimeters. The fourth guiding bore 2112d can have an open perimeter that defines the pair of opposing legs.

One or more of the first guiding bore 2112a, the second guiding bore 2112b, the third guiding bore 2112c and the fourth guiding bore 2112d can be aligned or circumferentially offset relative to one another or relative to the longitudinal axis A, and can be parallel or non-parallel to the longitudinal axis A so that the first guiding bore 2112a, the second guiding bore 2112b, the third guiding bore 2112c and the fourth guiding bore 2112d are substantially coaxially aligned with the first fastener bore 2110a, second fastener bore 2110b, third fastener bore 2110c and fourth fastener bore 2110d. Thus, each bone fastener 104 received through the respective one of the first guiding bore 2112a, the second guiding bore 2112b, the third guiding bore 2112c and the fourth guiding bore 2112d can be orientated at a different angle relative to the other bone fasteners 104. In addition, one or more of the first guiding bore 2112a, the second guiding bore 2112b, the third guiding bore 2112c and the fourth guiding bore 2112d can include the collet retaining feature or collet groove 2020. The collet groove 2020 can cooperate with the collet 2002 to retain the collet 2002 within the fixation device 2100 at a desired orientation. In one example, the collet groove 2020 can be formed about at least a portion of the perimeter or circumference of the first guiding bore 2112a, the second guiding bore 2112b, the third guiding bore 2112c and the fourth guiding bore 2112d. Alternatively, the collet groove 2020 can be formed substantially about the circumference of the first guiding bore 2108a, the second guiding bore 2108b and the third guiding bore 2108c.

Generally, the collet groove 2020 can be formed about enough of the circumference of the first guiding bore 2112a, the second guiding bore 2112b, the third guiding bore 2112c and the fourth guiding bore 2112d to ensure the collet 2002 is retained within the fixation device 2100 at an orientation that enables the bone fastener 104 to pass through the fixation device 2100. It should be noted that the use of a collet groove 2020 is merely exemplary as any suitable technique could be employed to ensure the proper orientation of the collet 2002 within the IM implant 2102, such as a slot, a notch, a keyed portion, a set screw, etc.

In one example, the collet groove 2020 can be formed along the portion of the circumference of the first guiding bore 2112a, the second guiding bore 2112b, the third guiding bore 2112c and the fourth guiding bore 2112d so that the collet 2002 can pivot or angulate relative to the respective one of the first guiding bore 2112a, the second guiding bore 2112b, the third guiding bore 2112c and the fourth guiding bore 2112d. In addition, the collet groove 2020 can receive the collet 2002 so that the collet 2002 can also rotate within the first guiding bore 2112a, the second guiding bore 2112b, the third guiding bore 2112c and the fourth guiding bore 2112d. The movement of the collet 2002 within the first guiding bore 2112a, the second guiding bore 2112b, the third guiding bore 2112c and the fourth guiding bore 2112d can enable flexibility in the placement of the bone fastener 104 through the IM implant 2102. Generally, as discussed with regard to FIGS. 48-51, the collet groove 2020 can be formed so that the collet 2002 can have about a 5 degree to about a 20 degree cone of movement within the respective one of the first guiding bore 2112a, the second guiding bore 2112b, the third guiding bore 2112c and the fourth guiding bore 2112d. The about 5 degree to about 20 degree cone of movement of the collet 2002 relative to the axis D1, D2, D3, D4 can allow the bone fastener 104 to be positioned into the anatomy free-hand or without the use of a targeting apparatus, if desired. Generally, the collet 2002 can be positioned within the fixation device 2100 so that the collet 2002 does not translate within the first guiding bore 2112a, the second guiding bore 2112b, the third guiding bore 2112c and the fourth guiding bore 2112d.

In order to employ the collet 2002 with the exemplary fixation device 2100, the moveable member 2108 and locking member 780 can be assembled within the IM implant 2102. Then, a collet 2002 can be positioned within each of the first guiding bore 2112a, the second guiding bore 2112b, the third guiding bore 2112c and the fourth guiding bore 2112d so that the ribs 2024a-d are retained within the collet groove 2020.

With the collets 2002 coupled to the IM implant 2102, the IM implant 2102 can be inserted into a prepared portion of the anatomy. In this example, the IM implant 2102 can be used in a retrograde interlocking femoral fixation procedure and can be inserted into the distal portion of the femur 80 in a retrograde direction. Once positioned within the intramedullary canal of the femur 80, bone fasteners 104 can be inserted through the anatomy into each of the first guiding bore 2112a, the second guiding bore 2112b, the third guiding bore 2112c and the fourth guiding bore 2112d. The collet 2002 can enable the bone fasteners 104 to be inserted about 5 to about 20 degrees offset from the axis D1, D2, D3, D4 of the first guiding bore 2112a, the second guiding bore 2112b, the third guiding bore 2112c and the fourth guiding bore 2112d, which can enable the bone fasteners 104 to be inserted without the use of a targeting instrument, if desired.

With the bone fasteners 104 inserted through the first guiding bore 2112a, the second guiding bore 2112b, the third guiding bore 2112c and the fourth guiding bore 2112d of the movable member 2108, the locking member 780 can be rotated to advance the movable member 2108 within the IM implant 2102, as discussed previously herein. The movement or advancement of the movable member 2108 within the longitudinal bore 113 can apply a force to the first end 2026 of the collets 2002, which can deform the collets 2002. The deformation of the collets 2002 can couple or lock the bone fasteners 104 to the IM implant 2102.

Figure 53:
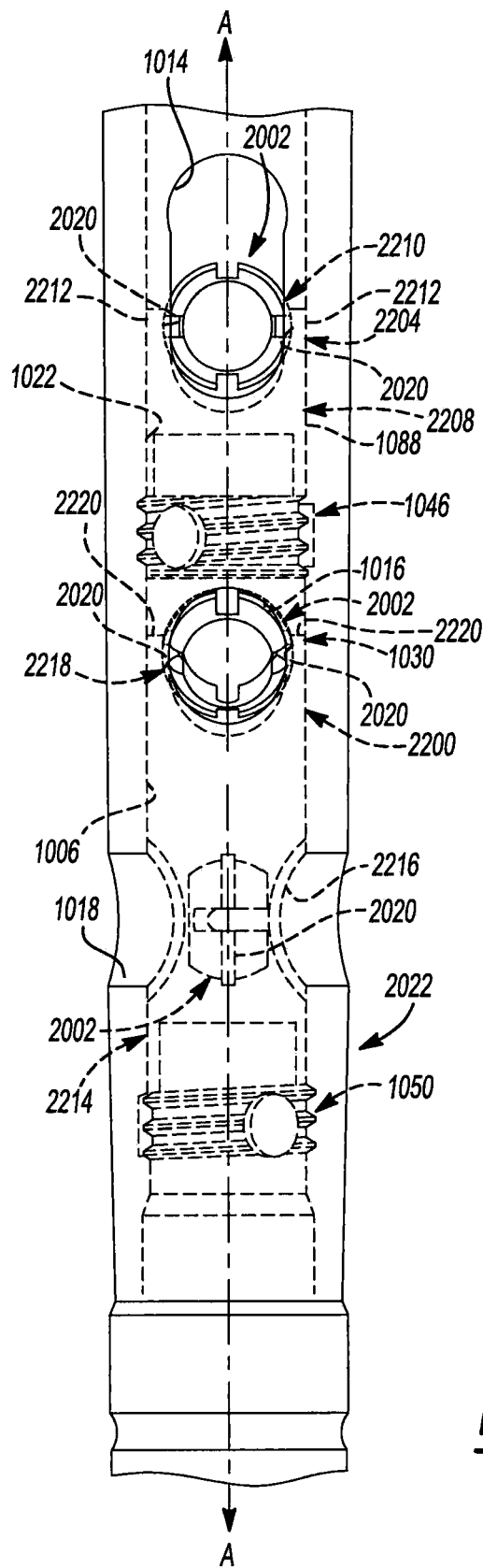
FIG. 53 is a detail view of another exemplary intramedullary implant including a fixation device having the variable angle positioning member according to the present teachings.

In another example, with reference to FIG. 53, the collet 2002 can be employed with an exemplary fixation device 2200, which can be assembled within the IM implant 1002. In the following, the same reference numerals will be used to denote the same or similar components as those in FIGS. 38-47B, and only the differences will be discussed in great detail herein. The IM implant 1002 can include the fixation device 2200, which can receive the variable angle positioning member or collet 2002. In this example, the collet 2002 can cooperate with the fixation device 2200 to enable fasteners 1112, 1114 inserted through the fixation device 2200 to be positioned at a variable angle relative to the IM implant 1002. The IM implant 2202 can include the longitudinal bore 1006, which can define the longitudinal axis A. The longitudinal bore 1006 can receive the fixation device 2200, which can include a compression device 2204 and a locking device 2206.

The compression device 2204 can include the first cannulated component 1046 and a second internally cannulated component 2208, which can be coupled to one another by a snap-fit arrangement or other type of connection. The second component 2208 of the compression device 2204 can include a guiding bore or an end opening 2210. The end opening 2210 can be defined between two opposing end extensions 2212 of the second component 2208 of the compression device 2204. The slot 1014 of the IM implant 2202 can be substantially aligned with the end opening 2210 of the compression device 2204 when the compression device 2204 is positioned within the longitudinal bore 1006 of the IM implant 1002. The second component 2208 can have the outer periphery 1088 of a shape substantially matching the shape of the periphery 1022 of a corresponding portion of the longitudinal bore 1006 of the IM implant 2102, as discussed previously herein.

The collet groove 2020 can be formed along one or more of the opposing end extensions 2212 of the second component 2208 of the compression device 2204 for retaining the collet 2002 within the compression device 2204. Generally, the collet groove 2020 can be formed in the end extensions 2212 so that the collet 2002 is retained within the end opening 2210, but can also be movable relative to the end opening 2210. In this regard, the collet groove 2020 can be formed so that the collet 2002 can pivot or angulate relative to the end opening 2210. In addition, the collet groove 2020 can receive the collet 2002 so that the collet 2002 can also rotate within the end opening 2210. Generally, as discussed with regard to FIGS. 48-51, the collet groove 2020 can be formed so that the collet 2002 can have the cone of movement M within the end opening 2210. The cone of movement M of the collet 2002 can allow the bone fastener 1110 to be positioned into the anatomy free-hand or without the use of the targeting instrument 1118, if desired. Generally, the collet 2002 can be positioned within the fixation device 2200 so that the collet 2002 does not translate within the end opening 2210.

The locking device 2206 can include the first internally cannulated component 1050 and a second internally cannulated component 2214. The second component 2214 of the locking device 2206 can include the longitudinal bore 342 and a guiding bore, through-aperture or bore 2216 transversely intersecting the longitudinal bore 342. The second component 2214 of the locking device 2206 can also include a guiding bore or an end opening 2218 defined between two opposing end extensions 2220 of the second component 2214 of the locking device 2206. The first and second apertures 1016, 1018 of the IM implant 2202 can be substantially aligned with the end opening 2218 and transverse aperture 2216 respectively of the locking device 2206 when the locking device 2206 is positioned within the longitudinal bore 1006 of the IM implant 1002. The second component 2214 can be keyed to the IM implant 2202, as discussed previously herein.

One or more of the transverse aperture 2216 and the end opening 2218 can include the collet groove 2020. In one example, the collet groove 2020 can be formed along at least a portion of the perimeter or circumference of the transverse aperture 2216. The collet groove 2020 can also be formed along one or more of the opposing end extensions 2220 of the second component 2214 of the locking device 2206. Generally, the collet groove 2020 can be formed along the transverse aperture 2216 and end opening 2218 of the locking device 2206 so that the collet 2002 is retained within the respective one of the transverse aperture 2216 and end opening 2218, but can also be movable relative to the transverse aperture 2216 and end opening 2218.

In this regard, the collet groove 2020 can be formed so that the collet 2002 can pivot or angulate relative to the end opening 2210. In addition, the collet groove 2020 can receive the collet 2002 so that the collet 2002 can also rotate within the transverse aperture 2216 and end opening 2218. Generally, as discussed with regard to FIGS. 48-51, the collet groove 2020 can be formed so that the collet 2002 can have the cone of movement M within the transverse aperture 2216 and end opening 2218. The cone of movement M of the collet 2002 can allow the bone fastener 104 to be positioned into the anatomy free-hand or without the use of the targeting instrument 1118, if desired. Generally, the collet 2002 can be positioned within the locking device 2206 so that the collet 2002 does not translate within the transverse aperture 2216 or end opening 2218.

In order to employ the collet 2002 with the exemplary fixation device 2200, the compression device 2204 and locking device 2206 can be assembled within the IM implant 2102. Then, collets 2002 can be positioned within each of the end opening 2210, transverse aperture 2216 and end opening 2218 so that the respective ones of the ribs 2024a-d are retained within the collet groove 2020.

With the collets 2002 coupled to the fixation device 2200, the IM implant 2202 can be inserted into a prepared portion of the anatomy. In this example, the IM implant 2202 can be used in an ankle arthrodesis procedure. Once the IM implant 2202 is positioned within the anatomy, the fixation fastener 1110 can be positioned through the collet 2002 in the end opening 2210 of the compression device 2204. Then, the compression driver 1024 can pass through the respective slot 2022a-d of the collet 2002 and can rotate the first component 1046 to move the second component 2208 within the IM implant 2202. The movement of the second component 2208 can move the fixation fastener 1110 along the slot 1014 until the fixation fastener 1110 and collet 2002 are held in compression between the end extensions 2212 of the end opening 2210.

Next, the fixation fasteners 1112, 1114 can be inserted through the anatomy into each of the transverse aperture 2216 and end opening 2218 of the locking device 2206. A suitable driver can engage the first component 1050 of the locking device 2206 to move the locking device 2206 within the longitudinal bore 1006 to apply a force to the collets 2002. The application of the force to the collets 2002 can deform the collets 2002. The deformation of the collets 2002 can couple or lock the fixation fasteners 1112, 1114 to the IM implant 2202.

Figure 54:
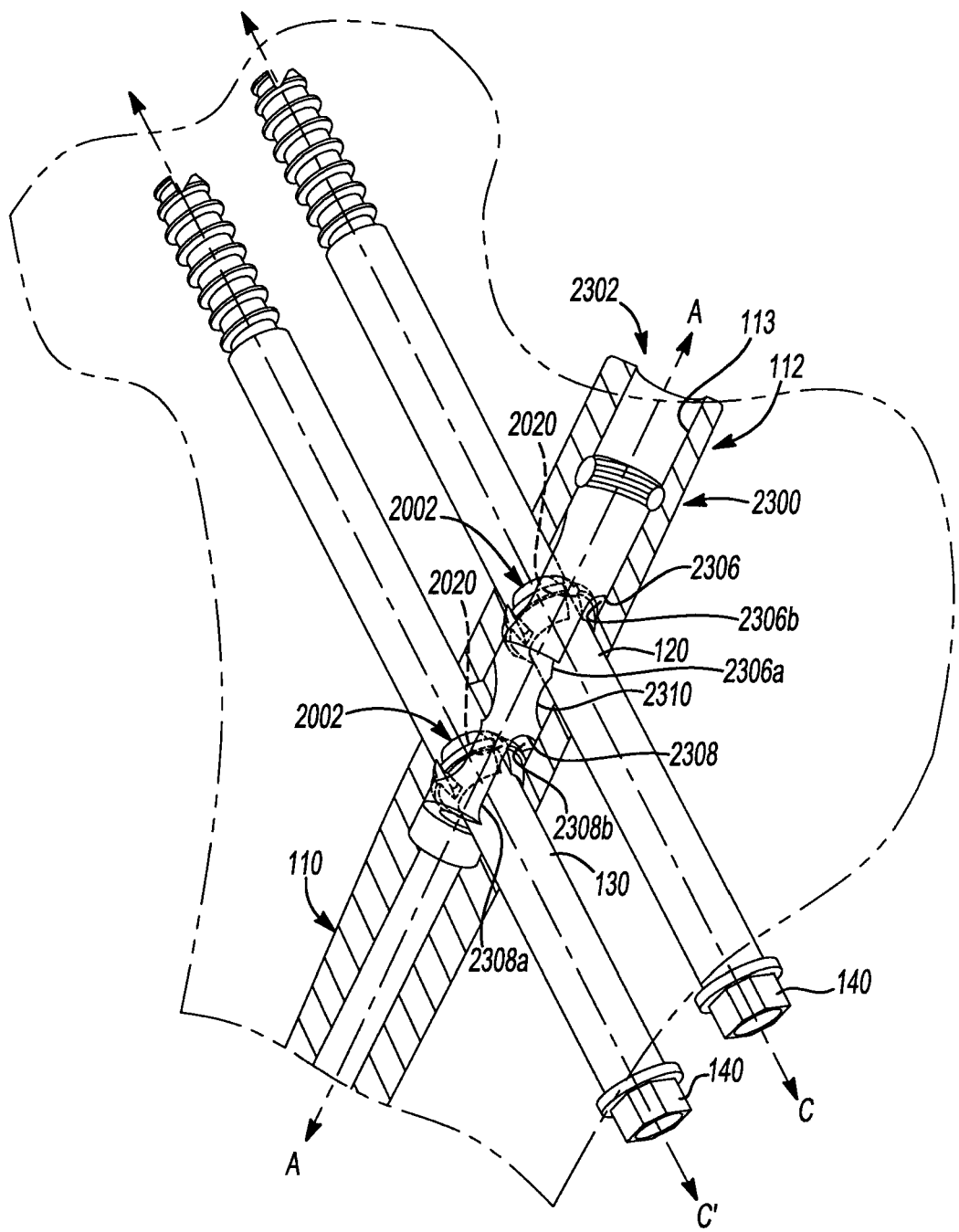
FIG. 54 is an environmental view of another exemplary intramedullary implant including a fixation device having the variable angle positioning member according to the present teachings.

In another example, with reference to FIG. 54, the collet 2002 can be employed with an exemplary fixation device 2300. The fixation device 2300 can be assembled within an IM implant 2302. In the following, the same reference numerals will be used to denote the same or similar components as those in FIGS. 20A-22, and only the differences will be discussed in great detail herein. The IM implant 2302 can include the fixation device 2300, which can receive the variable angle positioning member or collet 2002. In this example, the collet 2002 can cooperate with the fixation device 2300 to enable reconstructive fasteners 140 inserted through the fixation device 2300 to be positioned at a variable angle relative to the IM implant 2302.

As the IM implant 2302 can be similar to the IM implant 102 discussed with regard to FIGS. 1-6C, the IM implant 2302 will not be discussed in great detail herein, and the same reference numerals will be used to denote the same or similar components. Briefly, however, the IM implant 2302 can include the shaft 110 having proximal portion 112. The proximal portion 112 can include the longitudinal bore 113 formed along the longitudinal axis A, which can receive the fixation device 2300. The proximal portion 112 can include the first and second fastener bores 120, 130. The first and second fastener bores 120, 130 can be formed along the axes C, C', which can be transverse to the longitudinal axis A.

The fixation device 2300 can be received within the longitudinal bore 113 of the IM implant 2302. As the fixation device 2300 can be similar to the securing device 700 discussed with regard to FIGS. 20A-22, the same reference numerals will be used to denote the same or similar components. The fixation device 2300 can include a movable member 2304 and a locking member 780. The movable member 2304 can include a first guiding bore 2306, a second guiding bore 2308 and a third guiding bore 2310. The first guiding bore 2306 and the second guiding bore 2308 can each include opposing side walls 2306a, 2306; 2308a, 2308b. At least one of the opposing side walls 2306a, 2306b, 2308a, 2308b can include the collet groove 2020. The collet grooves 2020 can enable collets 2002 to be retained and moveable relative to each of the first guiding bores 2306 and second guiding bores 2308.

In one example, collet grooves 2020 can be formed on at least one of the side walls 2306a, 2306b, 2308a, 2308b of the first guiding bore 2306 and second guiding bore 2308. The collet grooves 2020 can be formed so that the collets 2002 can pivot or angulate relative to the first guiding bore 2306 and second guiding bore 2308. In addition, the collet grooves 2020 can receive the collets 2002 so that the collets 2002 can also rotate within the first guiding bore 2306 and second guiding bore 2308. Generally, as discussed with regard to FIGS. 48-51, the collet grooves 2020 can be formed so that the collets 2002 can have the cone of movement M within the first guiding bore 2306 and second guiding bore 2308. The cone of movement M of the collet 2002 can allow the reconstructive fastener 140 to be positioned into the anatomy freehand or without the use of the targeting instrument, if desired. Generally, the collets 2002 can be positioned within the collet grooves 2020 so that the collets 2002 does not translate within the first guiding bore 2306 and second guiding bore 2308.

In order to employ the collets 2002 with the exemplary fixation device 2300, the fixation device 2300 can be assembled within the longitudinal bore 113 of the IM implant 2302. Then, collets 2002 can be positioned within each of the first guiding bore 2306 and second guiding bore 2308 so that the respective ones of the ribs 2024a-d are retained within the collet grooves 2020.

With the collets 2002 coupled to the fixation device 2300, the IM implant 2302 can be inserted into a prepared portion of the anatomy. In this example, the IM implant 2302 can be used in a piriformis procedure. Once the IM implant 2302 is positioned within the anatomy, the bone fasteners 140 can be positioned through the collets 2002 in the first guiding bore 2306 and second guiding bore 2308. Then, the movable member 2304 can be moved within the longitudinal bore 113. The movement of the movable member 2304 within the longitudinal bore 113 can compress the collet 2002 about the reconstructive fastener 140, thereby securing the reconstructive fasteners 140 to the IM implant 2302.

Thus, the collets 2002 can be used with a variety of fixation devices 2004, 2100, 2200, 2300 to enable bone fasteners 104, 1110 or reconstructive fasteners 140 to be positioned at a variable angle relative to an axis of the respective guiding bore 2018, 2112, 2210, 2216, 2218, 2306, 2308, 2310. The ability of the collets 2002 to move within the guide bores 2018, 2112, 2210, 2216, 2218, 2306, 2308, 2310 can enable the bone fastener 104, 1110 or reconstructive fasteners 140 to be positioned free-hand, or without the use of a targeting instrument, if desired. It should be noted that employing the collets 2002 with the fixation devices 2004, 2100, 2200, 2300 is merely exemplary, as the collets 2002 could be employed with any of the fixation devices 100 described and illustrated herein.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An orthopedic device comprising:
   an intramedullary implant defining a longitudinal bore along a longitudinal axis and at least one bore formed along an axis for receipt of a fastener;
   a fixation device receivable within the longitudinal bore, the fixation device having at least one guiding bore formed along a guiding axis transverse to the longitudinal axis;
   at least one collet received within the at least one guiding bore for positioning the fastener at a variable angle relative to the guiding axis of the fixation device and the axis of the intramedullary implant; and
   a locking member engageable with the longitudinal bore and configured for rotation and engagement with the fixation device,
   wherein the at least one guiding bore includes a collet retaining feature formed in at least a portion of the circumference of the at least one guiding bore that laterally extends in a direction normal to the guiding axis and couples the at least one collet to the at least one guiding bore for receipt of the fastener, and
   wherein rotation of the locking member, when engaged with the longitudinal bore and the fixation device, advances the fixation device in the longitudinal bore in a proximal/distal direction, and advancement of the fixation device applies a force to the at least one collet to deform the at least one collet for coupling the fastener to the intramedullary implant.

2. The orthopedic device of claim 1, wherein the at least one collet includes at least one rib and the collet retaining feature comprises a groove that receives the at least one rib to movably couple the at least one collet to the fixation device.

3. The orthopedic device of claim 1, wherein the at least one guiding bore is defined by opposing side walls, and at least one of the opposing side walls defines a collet retaining feature that couples the at least one collet to the at least one guiding bore.

4. The orthopedic device of claim 1, wherein the at least one collet is movable relative to the at least one guiding bore.

5. The orthopedic device of claim 4, wherein the at least one collet is movable about 5 degrees to about 20 degrees about the guiding axis.

6. The orthopedic device of claim 1, wherein the at least one collet is deformable.

7. The orthopedic device of claim 6, wherein the collet is annular having a central bore for receipt of the fastener and at least one slot.

8. An orthopedic device comprising:
   a fixation device having a longitudinal axis and defining at least a first guiding bore along a first guiding axis transverse to the longitudinal axis and second guiding bore along a second guiding axis transverse to the longitudinal axis, the first guiding bore and the second guiding bore each including a retaining feature formed along a portion of each of the first guiding bore and the second guiding bore that laterally extends in a direction normal to the respective first and second guiding axes and;
   a collet coupled to the retaining feature of each of the first guiding bore and the second guiding bore so that each collet is movable relative to each of the first guiding bore and the second guiding bore for positioning a fastener at a variable angle relative to the respective one of the first guiding axis and second guiding axis;
   an intramedullary implant defining a first implant bore, a second implant bore and a longitudinal bore that receives the fixation device, the first implant bore substantially coaxially aligned with the first guiding bore and the second implant bore substantially coaxially aligned with the second guiding bore when the fixation device is in a first position for receipt of a first bone fastener through the first implant bore and first guiding bore and a second bone fastener through the second implant bore and second guiding bore; and
   a locking member coupled to the fixation device and configured for rotation, the locking member at least partially received within the longitudinal bore of the intramedullary implant, wherein rotation of the locking member advances the fixation device in the longitudinal bore from the first position to a second position for coupling the first and second bone fasteners to the intramedullary implant.

9. The orthopedic device of Claim 8, wherein the collet is deformable, and the movement of the fixation device from the first position to the second position deforms the collet.

10. The orthopedic device of claim 8, wherein the collet is annular and includes a rib formed about at least a portion of the circumference of the collet, the collet defining a central bore.

11. The orthopedic device of claim 10, wherein the retaining feature comprises a groove that receives the rib of the collet to movably couple the collet to the fixation device.

12. The orthopedic device of claim 8, wherein at least one of the first guiding bore and the second guiding bore is defined by opposing side walls, and at least one of the opposing side walls defines the retaining feature.

13. An orthopedic device comprising:
   an intramedullary implant defining a longitudinal bore along a longitudinal axis and at least one bore formed along an axis transverse to the longitudinal axis for receipt of a fastener;
   a movable fixation device receivable within the longitudinal bore, the fixation device having at least one guiding bore formed along a guiding axis transverse to the longitudinal axis, the at least one guiding bore including a retaining feature formed along at least a portion of the guiding bore that laterally extends in a direction normal to the respective first and second guiding axes, the at least one guiding bore coaxially aligned with the at least one bore in a first position; and at least one deformable collet having a rib coupled to the retaining feature of the at least one guiding bore for positioning the fastener at a variable angle relative to the guiding axis of the fixation device and the axis of the intramedullary nail; and a locking member engaged with the fixation device and configured for rotation, the locking member at least partially receivable within the longitudinal bore, wherein rotation of the locking member moves the fixation device from the first position to a second position within the longitudinal bore, and wherein movement of the fixation device from the first position to the second position within the longitudinal bore deforms the at least one collet to couple the fastener to the intramedullary implant.

14. The orthopedic device of claim 13, wherein the at least one collet is annular and the rib is formed about at least a portion of a circumference of the at least one collet.

15. The orthopedic device of claim 13, wherein the at least one collet is movable within the at least one guiding bore.

16. The orthopedic device of claim 15, wherein the at least one collet is movable about 5 degrees to about 20 degrees about the guiding axis.

* * * * *